(12) United States Patent
Karsenty et al.

(10) Patent No.: US 9,150,521 B2
(45) Date of Patent: Oct. 6, 2015

(54) METHODS OF PREVENTING AND TREATING DIABETES BY INHIBITING SEROTONIN SYNTHESIS

(71) Applicants: Gerard Karsenty, New York, NY (US); Grzegorz Sumara, New York, NY (US); Olga Sumara, New York, NY (US)

(72) Inventors: Gerard Karsenty, New York, NY (US); Grzegorz Sumara, New York, NY (US); Olga Sumara, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/375,722

(22) PCT Filed: Jan. 31, 2013

(86) PCT No.: PCT/US2013/024177
§ 371 (c)(1),
(2) Date: Jul. 30, 2014

(87) PCT Pub. No.: WO2013/116538
PCT Pub. Date: Aug. 8, 2013

(65) Prior Publication Data
US 2014/0378489 A1    Dec. 25, 2014

Related U.S. Application Data

(60) Provisional application No. 61/594,170, filed on Feb. 2, 2012.

(51) Int. Cl.
| | | |
|---|---|---|
| C07D 239/47 | (2006.01) | |
| A61K 45/06 | (2006.01) | |
| A61K 31/513 | (2006.01) | |
| A61K 31/505 | (2006.01) | |
| C12Q 1/26 | (2006.01) | |
| G01N 33/94 | (2006.01) | |

(52) U.S. Cl.
CPC ............ *C07D 239/47* (2013.01); *A61K 31/505* (2013.01); *A61K 31/513* (2013.01); *A61K 45/06* (2013.01); *C12Q 1/26* (2013.01); *G01N 33/942* (2013.01); *G01N 2333/90245* (2013.01); *G01N 2800/042* (2013.01); *G01N 2800/52* (2013.01)

(58) Field of Classification Search
USPC ........................................................ 514/272
See application file for complete search history.

(56) References Cited

U.S. PATENT DOCUMENTS

| | | |
|---|---|---|
| 2011/0281899 A1 | 11/2011 | Karsenty et al. |
| 2012/0004165 A1 | 1/2012 | Keil et al. |

FOREIGN PATENT DOCUMENTS

| | | |
|---|---|---|
| WO | 2011/053977 A1 | 5/2011 |
| WO | 2011/056916 A1 | 5/2011 |

*Primary Examiner* — Kristin Vajda
(74) *Attorney, Agent, or Firm* — Kenyon & Kenyon LLP

(57) ABSTRACT

The present invention provides methods and therapeutic agents for lowering serum or plasma serotonin levels in a patient in order to prevent or treat diabetes. In preferred embodiments, the patient is known to have, or to be at risk for, diabetes and the agents are TPH1 inhibitors.

13 Claims, 29 Drawing Sheets

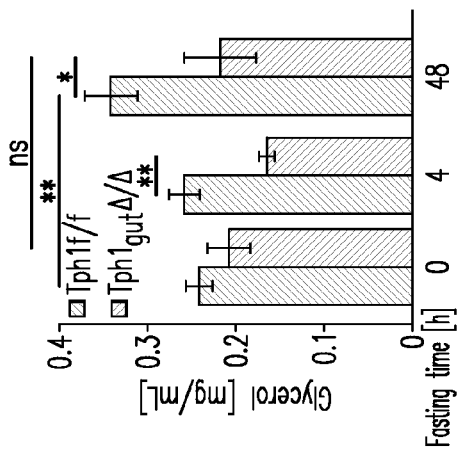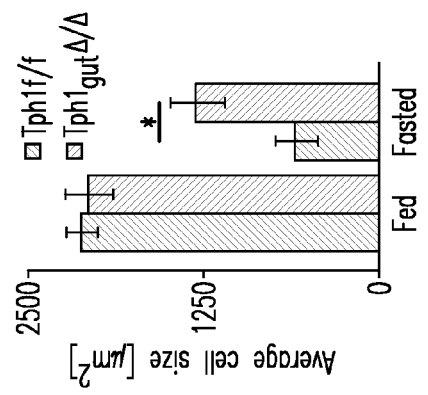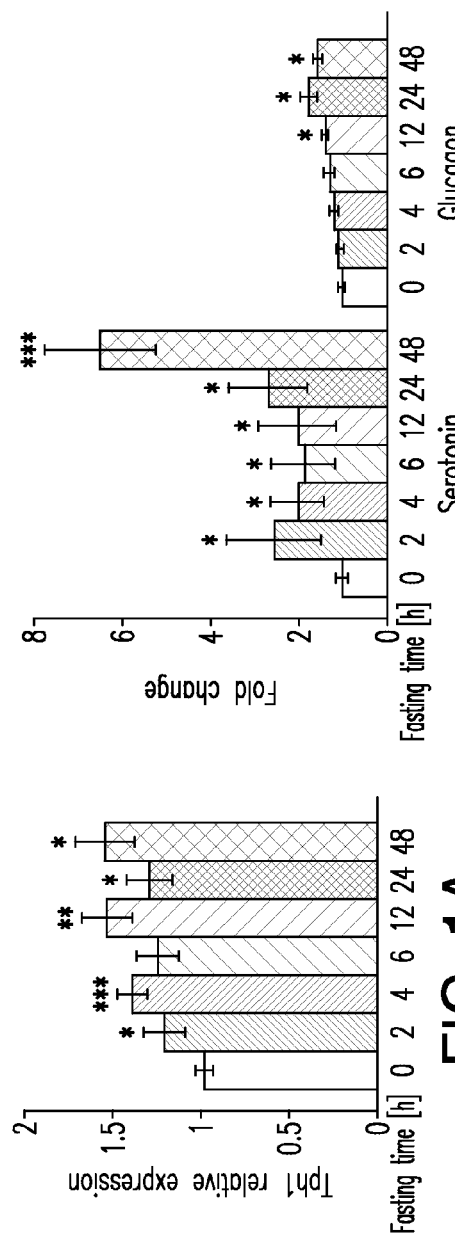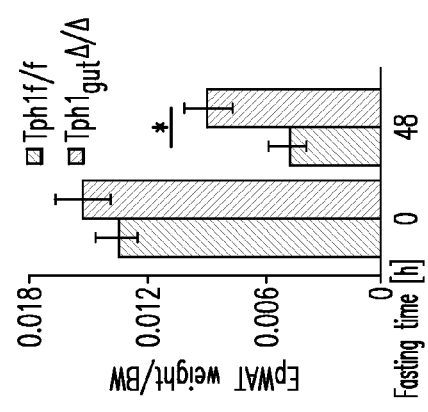
FIG. 1A  FIG. 1B  FIG. 1C
FIG. 1D  FIG. 1E  FIG. 1F

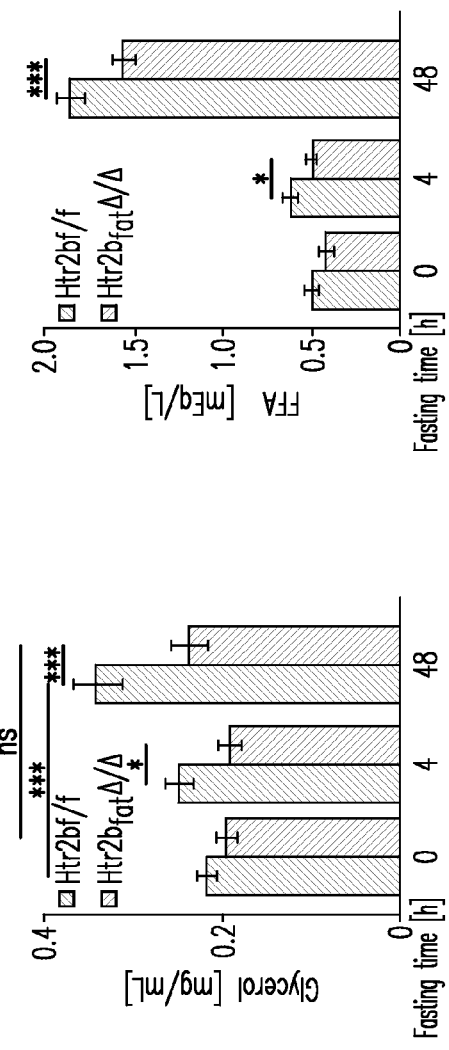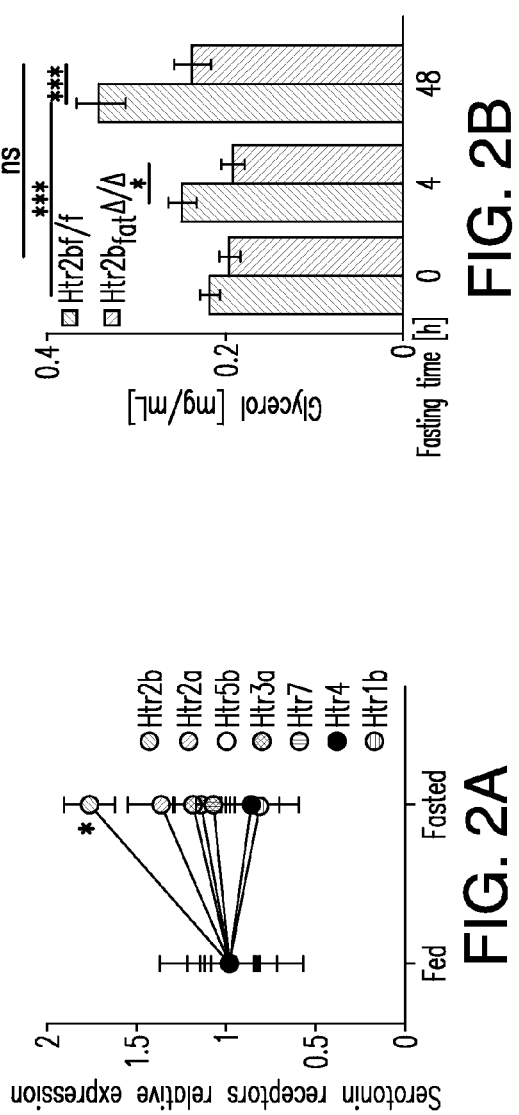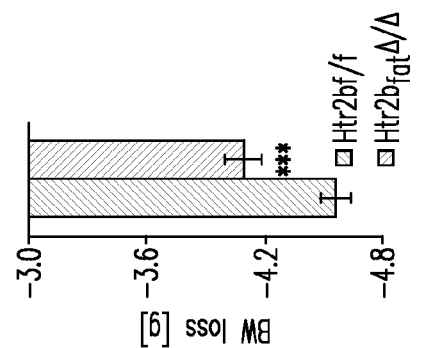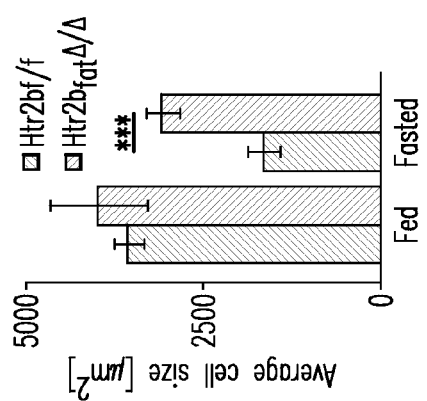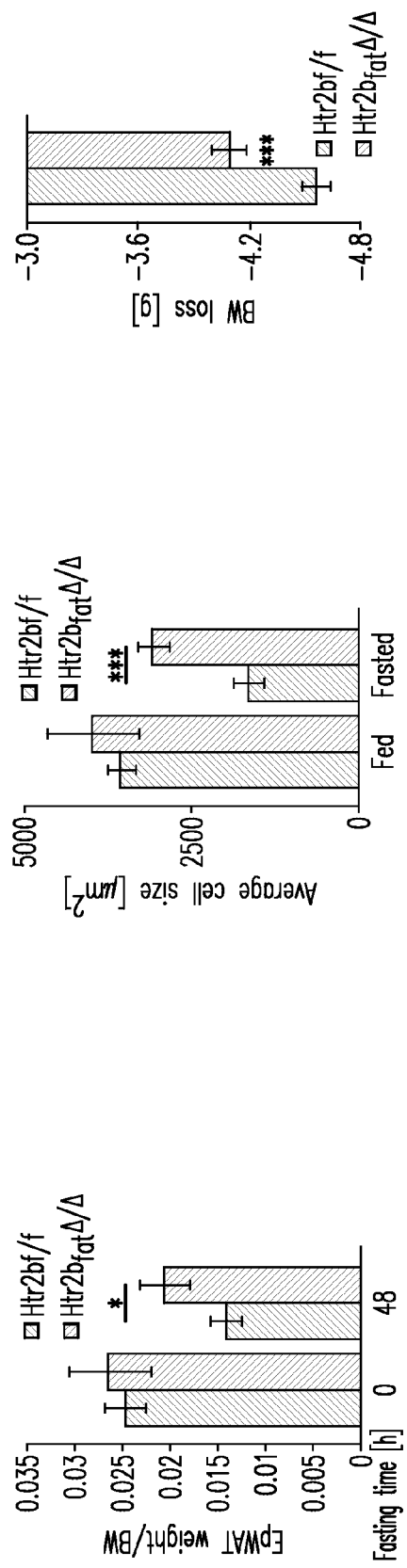

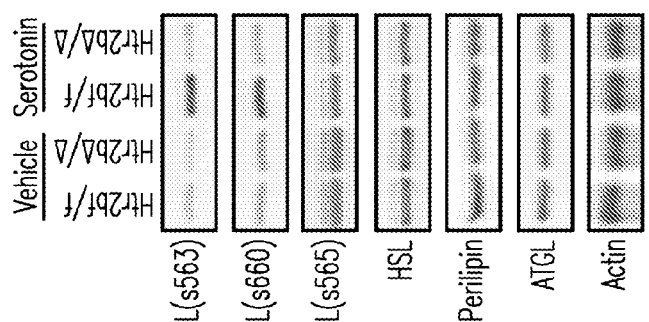
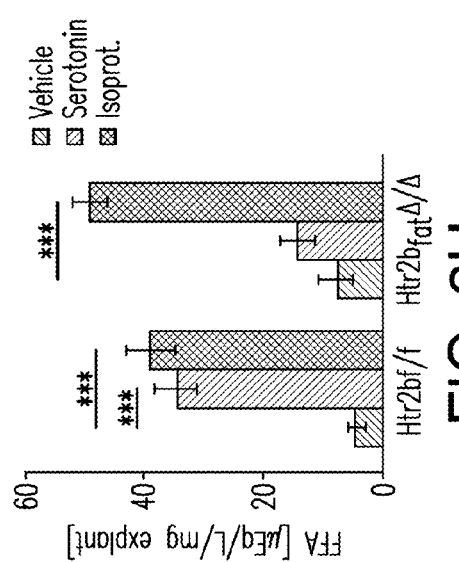
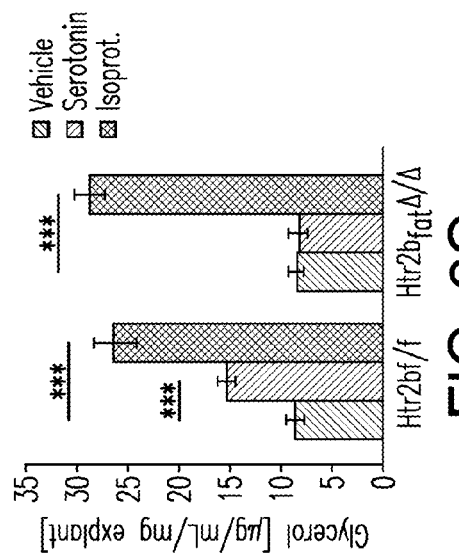

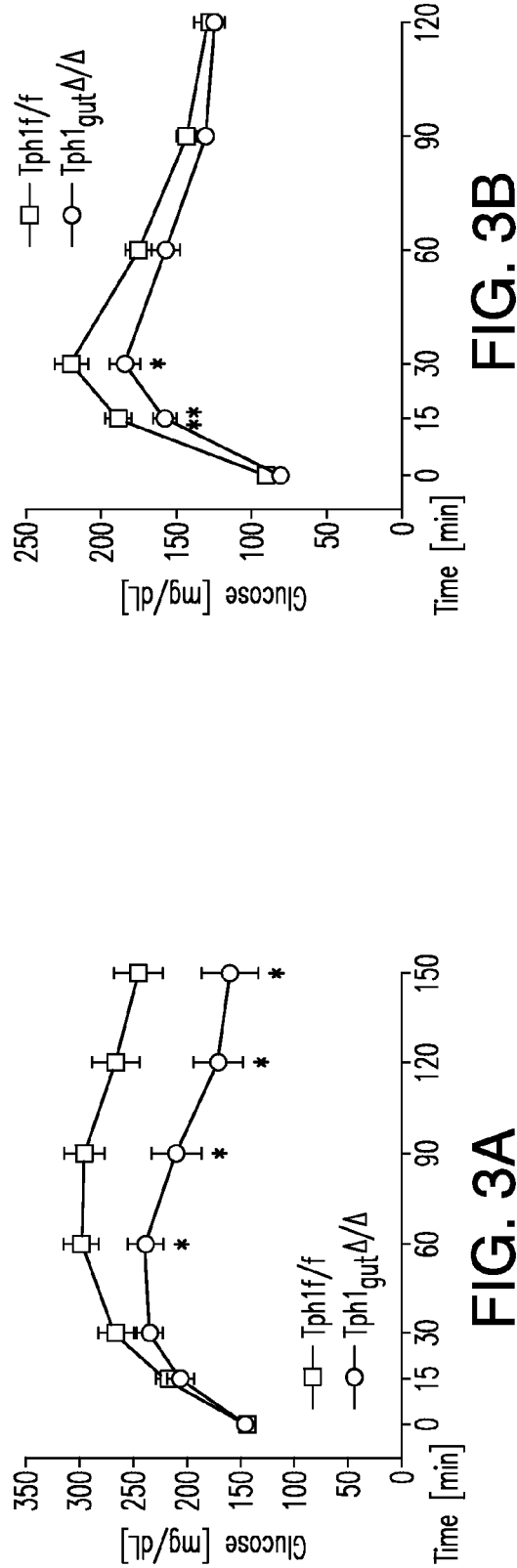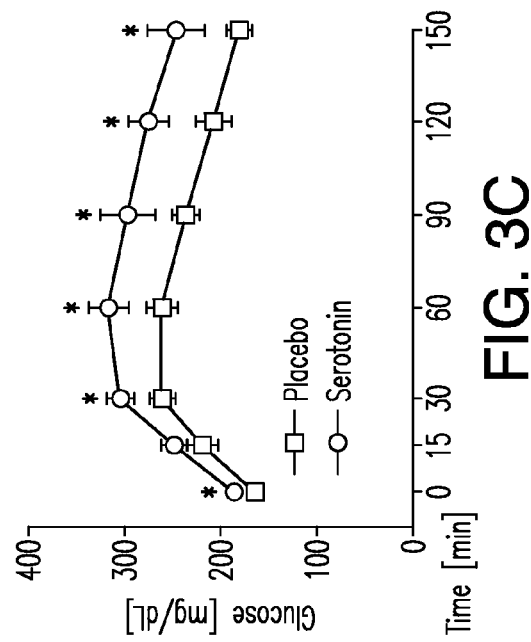
FIG. 3A
FIG. 3B
FIG. 3C

| | Body Weight [g] | Basal Glucose [mg/dL] | Clamp Glucose [mg/dL] | Glucose Infusion Rate [mg/kg/min] | Basal Hepatic Glucose Production [mg/kg/min] | Glucose Turnover [mg/kg/min] | Whole Body Glycolysis [mg/kg/min] | Fat Mass [g] | Lean Mass [g] | Glycogen Synthesis Rate [mg/kg/min] |
|---|---|---|---|---|---|---|---|---|---|---|
| Tph1f/f | 19+/-1 | 123+/-5 | 128+/-6 | 28.1+/-2.3 | 15.4+/-1.7 | 39.5+/-3.1 | 21.5+/-2 | 2.6+/-0.3 | 18.3+/-0.6 | 15.8+/-0.7 |
| Tph1 gutΔ/Δ | 19+/-0.4 | 129+/-7 | 127+/-4 | 34.7+/-2.3 | 14.9+/-1.1 | 38.1+/-2.3 | 18.9+/-1.9 | 2.7+/-0.2 | 18.1+/-0.5 | 18.2+/-0.8 |
| T-test | 0.95 | 0.52 | 0.93 | 0.05 | 0.7 | 0.72 | 0.38 | 0.59 | 0.83 | 0.06 |

FIG. 7A

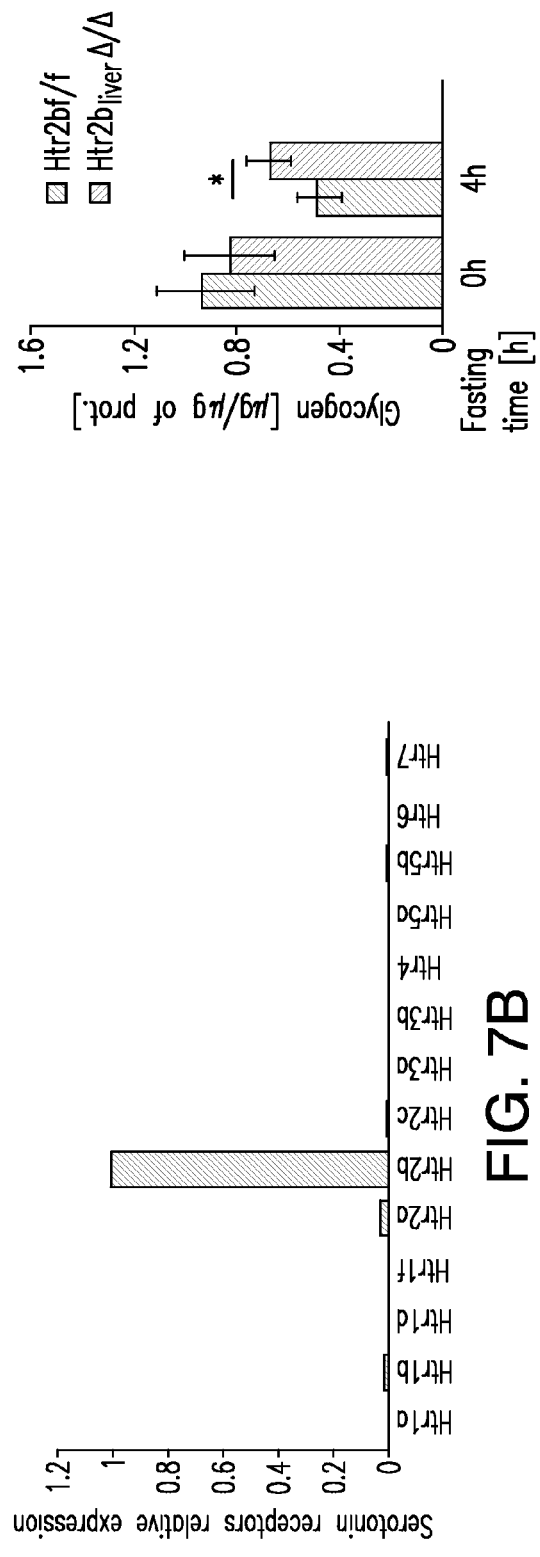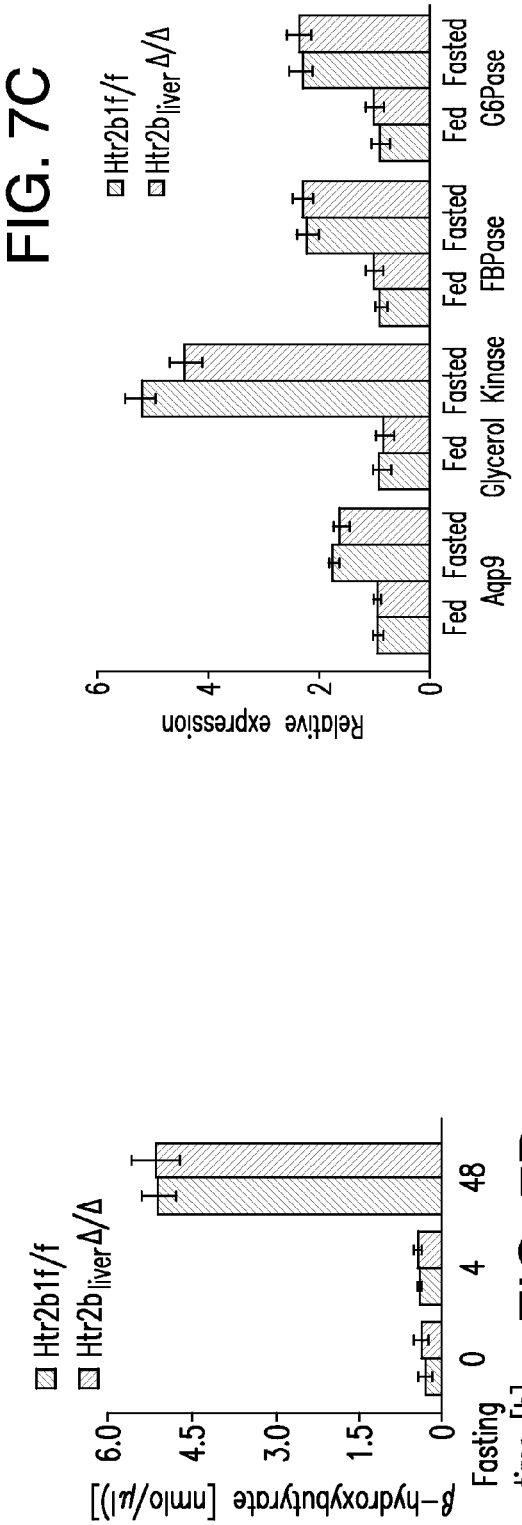
FIG. 7B
FIG. 7C
FIG. 7D
FIG. 7E

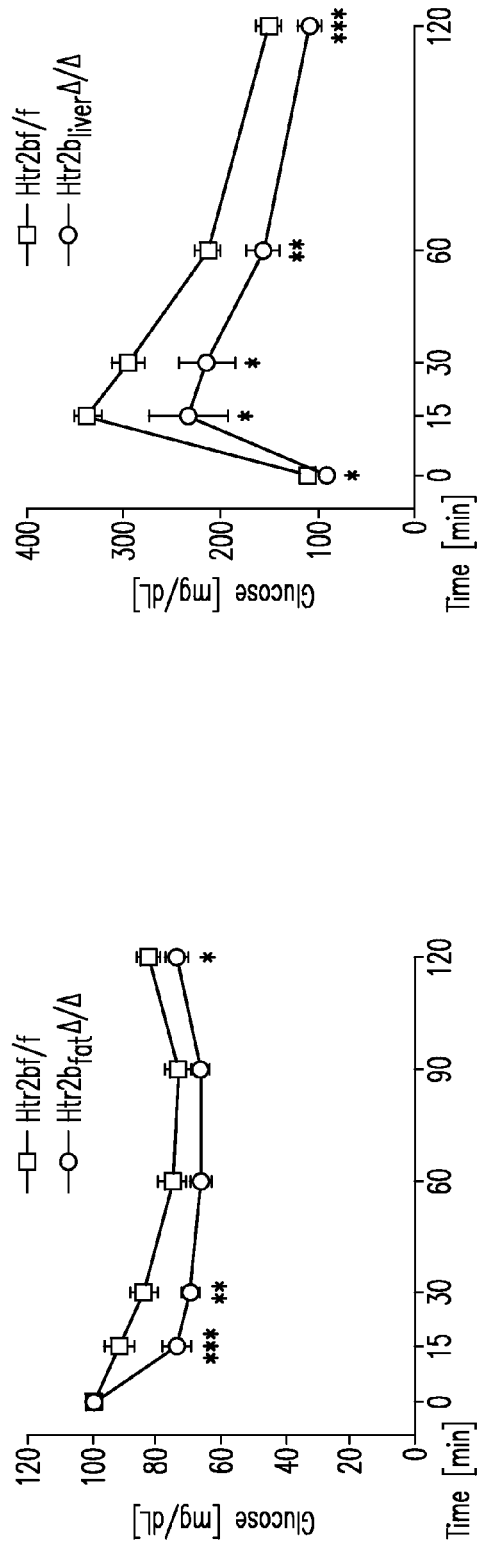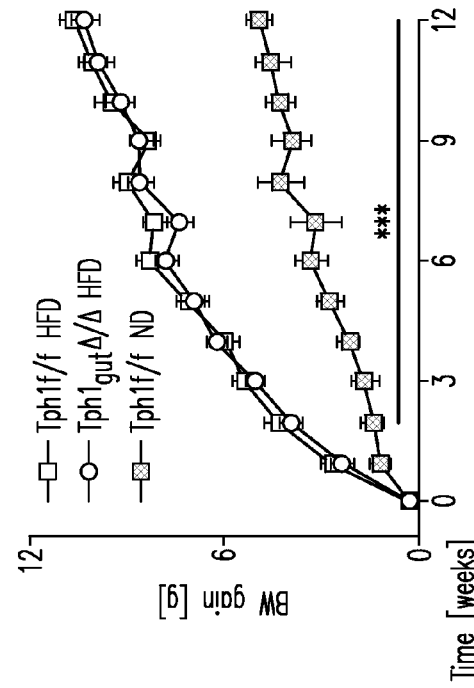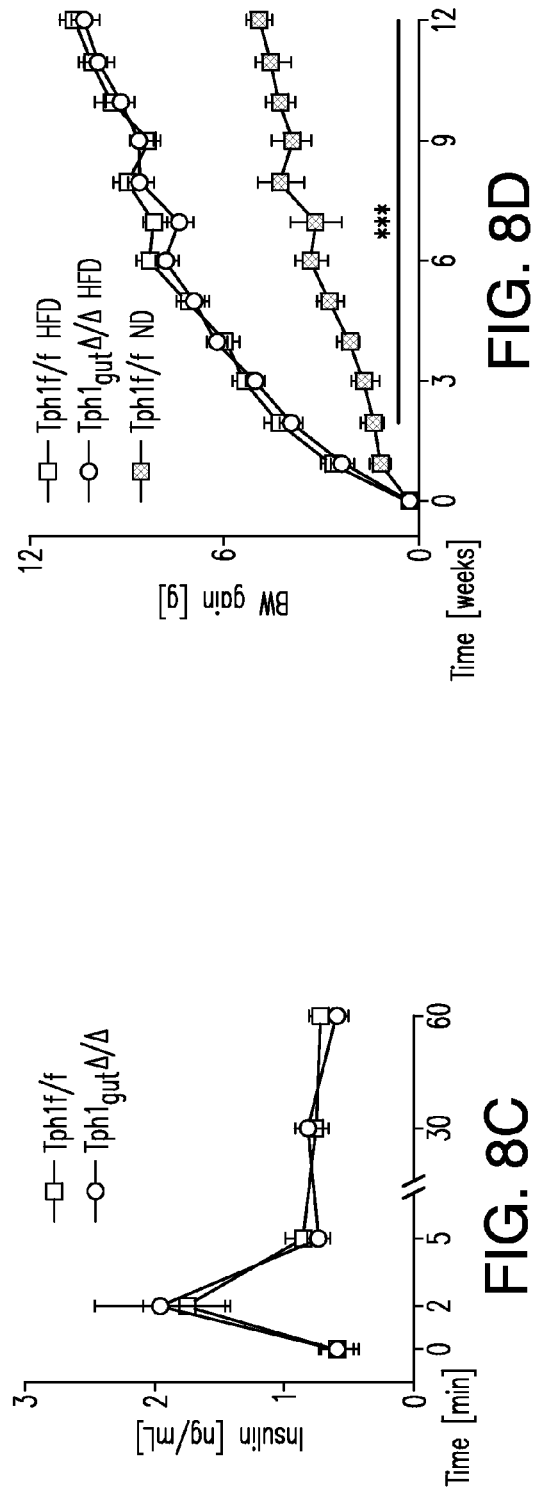
FIG. 8A
FIG. 8B
FIG. 8C
FIG. 8D

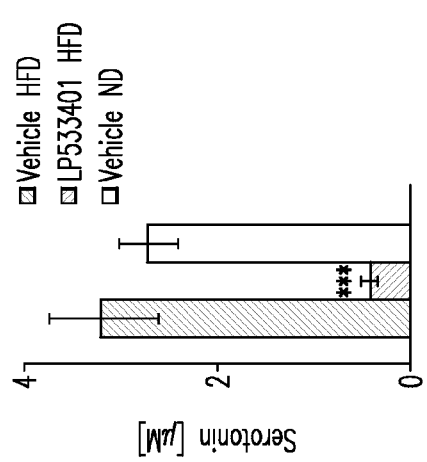
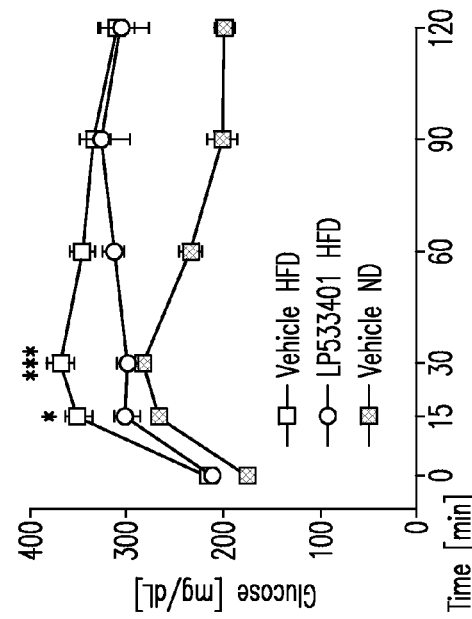
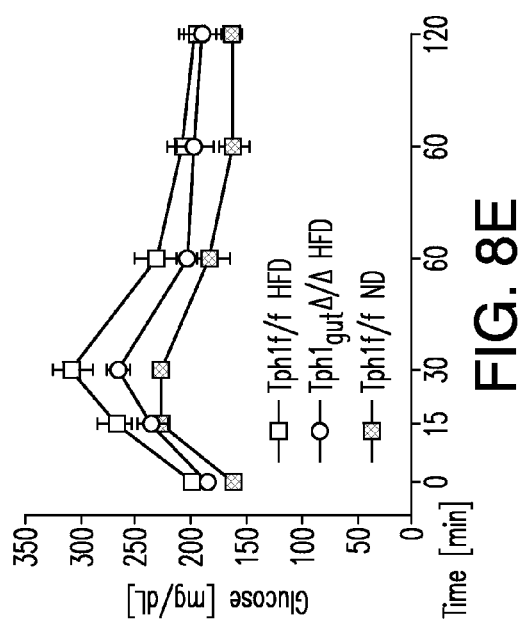
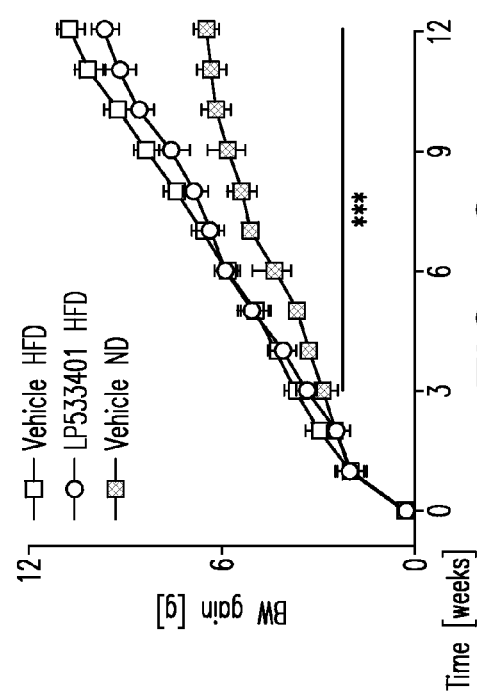

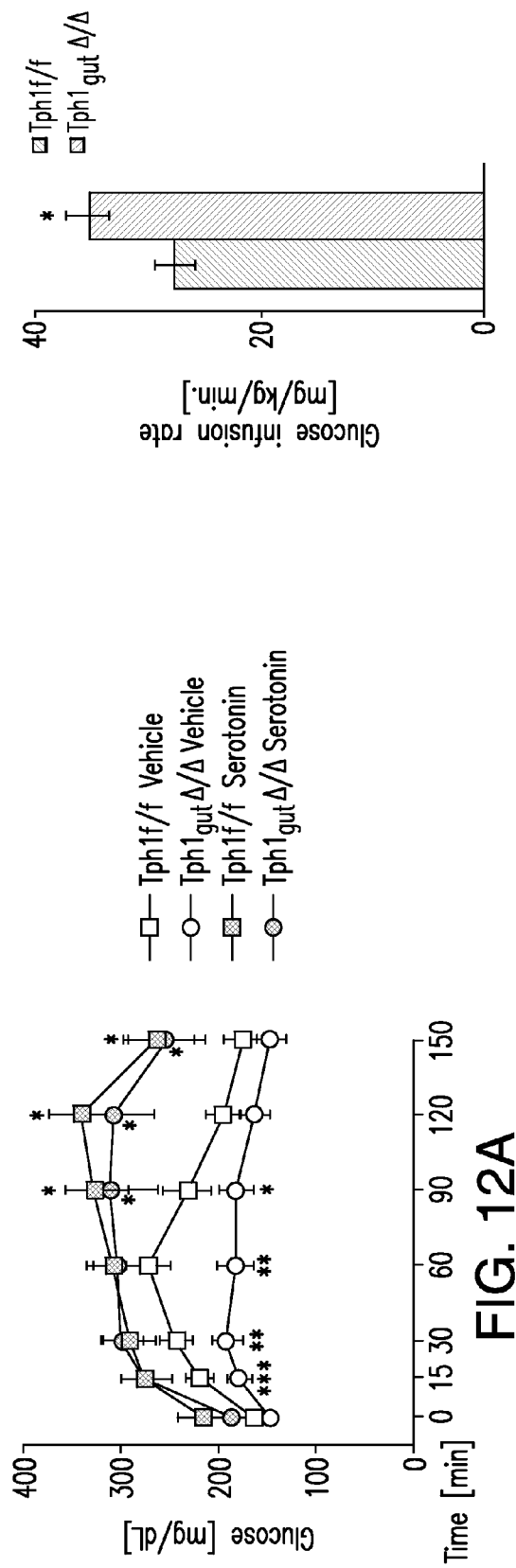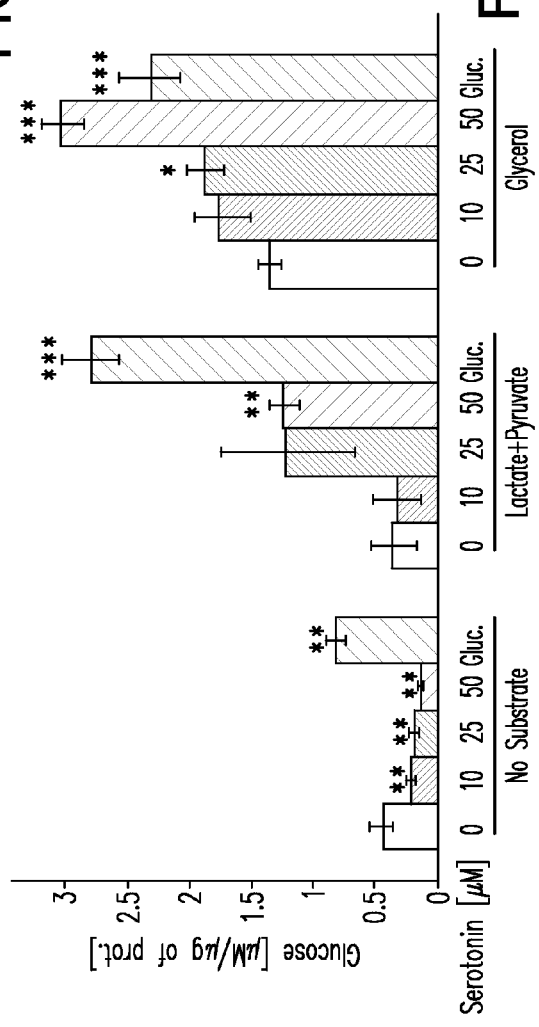

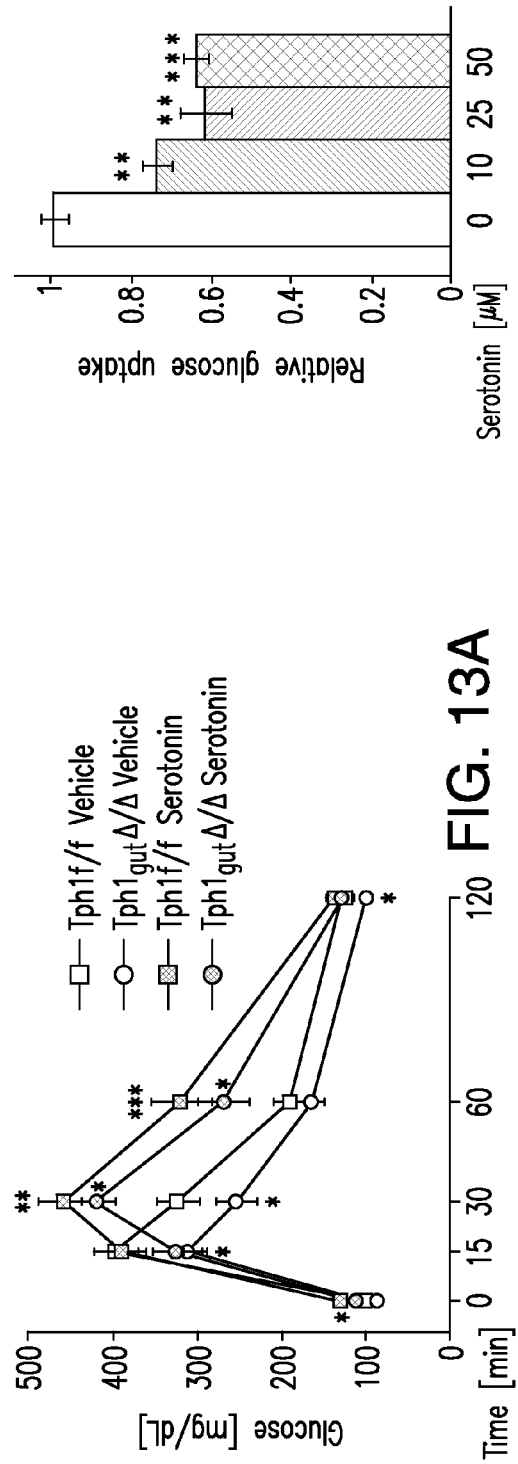
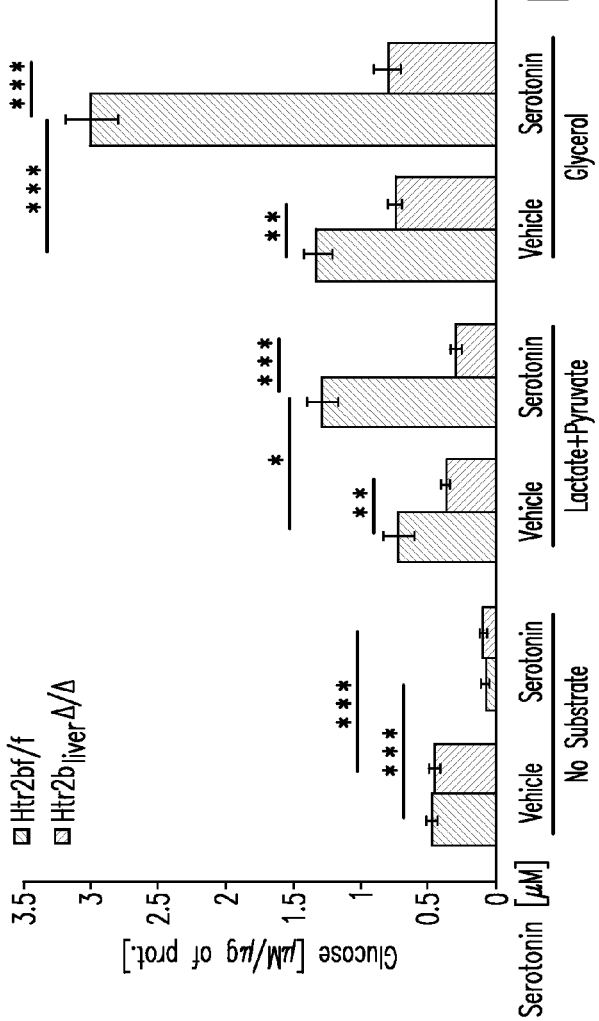
FIG. 13A
FIG. 13B
FIG. 13C

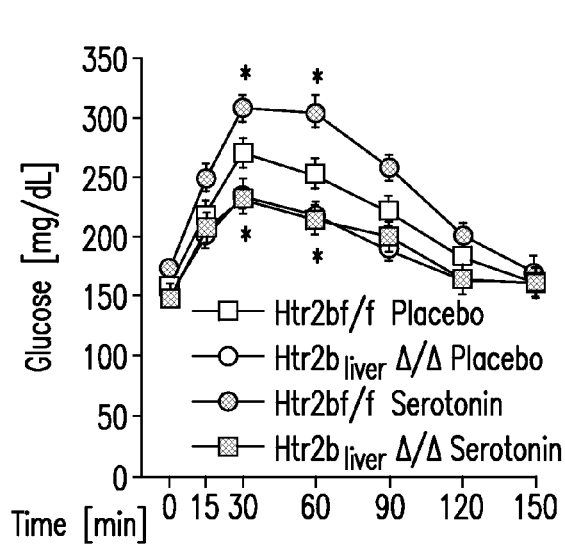
FIG. 14A
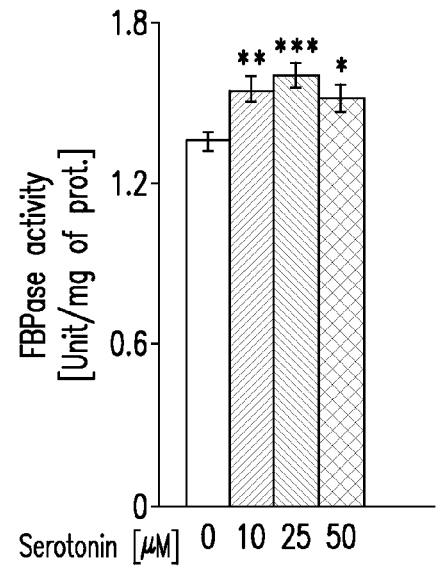
FIG. 14B
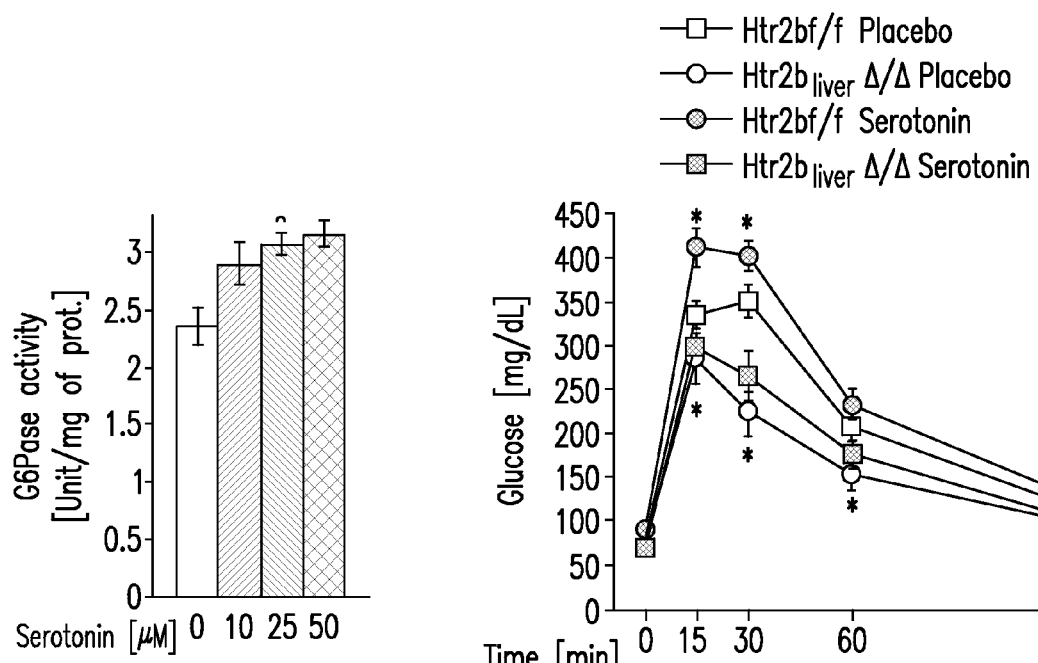
FIG. 14C
FIG. 14D

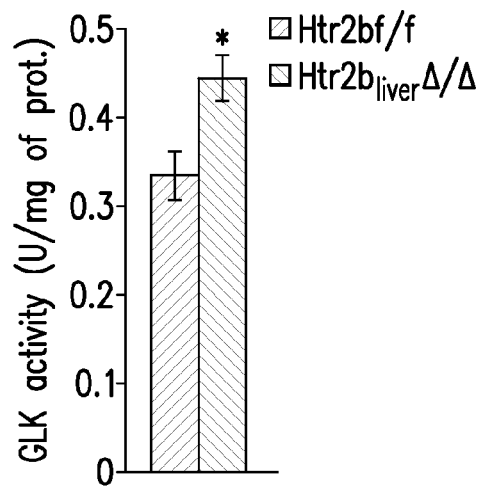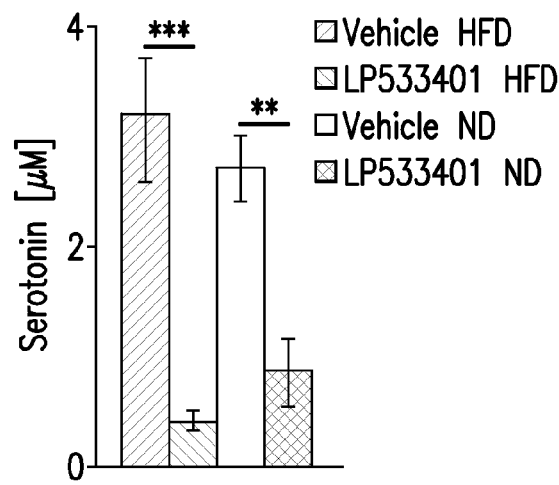
FIG. 16A  FIG. 16B
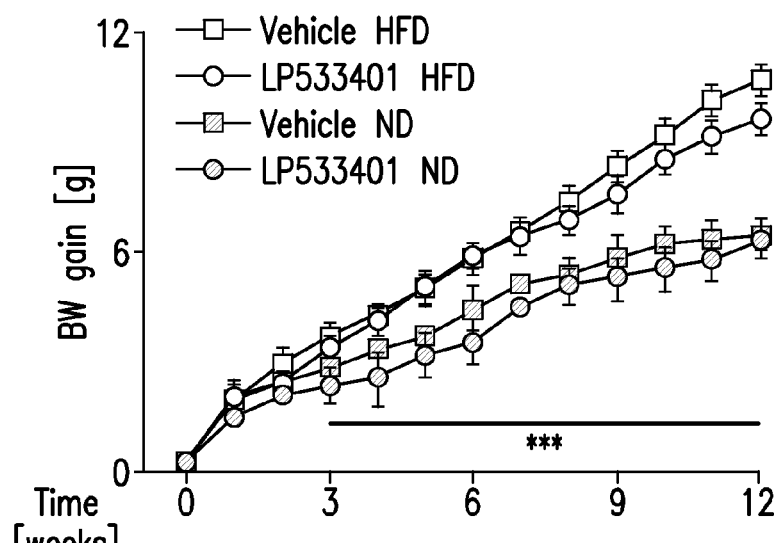
FIG. 16C

METHODS OF PREVENTING AND TREATING DIABETES BY INHIBITING SEROTONIN SYNTHESIS

CROSS-REFERENCE TO RELATED APPLICATIONS

This application claims priority from U.S. Provisional Patent Application Ser. No. 61/594,170, filed Feb. 2, 2012, the disclosures of which are incorporated herein by reference in their entirety.

STATEMENT OF GOVERNMENT INTEREST

The invention was made with Government support under NIH 2 RO1 DK 067936 awarded by the National Institutes of Health. The Government has certain rights in the invention.

FIELD OF THE INVENTION

The invention is in the field of the therapy of diabetes and provides methods for treating diabetes in mammals, particularly in humans.

BACKGROUND OF THE INVENTION

Diabetes mellitus (non-insulin-dependent, or Type II, diabetes) is a group of disorders characterized by high blood glucose levels (hyperglycemia) that generally involves an impaired insulin secretory response to glucose as well as insulin resistance. The mechanism of insulin action is impaired in diabetes, leading to less glucose transport into muscle and fat. The elevated blood glucose levels that result can lead to a variety of serious health problems.

Serotonin (5-hydroxytryptamine, 5-HT) is a biogenic amine that functions both as a neurotransmitter in the mammalian central nervous system and as a hormone in the periphery, where most of it is produced (Gershon et al., 1990, Neuropsychopharmacology, 3:385-395). Serotonin is generated through an enzymatic cascade in which L-tryptophan is converted into L-5-hydroxytryptophan by an enzyme called tryptophan hydroxylase (TPH). This intermediate product is then converted to serotonin by an aromatic L-amino acid decarboxylase. There are two TPH encoding genes, TPH1 and TPH2, which are 71% identical in amino acid sequence and about 90% similar in their catalytic domains. While TPH1 controls serotonin synthesis in the periphery, TPH2 is responsible for serotonin synthesis in the brain (Walther et al., 2003, Science 299:76). Given that serotonin cannot cross the blood-brain barrier, these two genes are therefore solely responsible for regulating the level of this molecule in the periphery and in the brain, respectively.

TPH1 is expressed almost exclusively in cells of the duodenum, and it is responsible for the synthesis of peripheral serotonin, which represents 95% of total serotonin (Gershon & Tack, 2007, Gastroenterology 132:397-414). TPH1 expression in any tissues other than duodenum is at least 100-1000 fold lower. Thus, TPH1 can be viewed as a duodenum-specific gene and peripheral serotonin production as a duodenum-specific process.

Besides its role as a neuromediator, and because of its abundance in the general circulation, serotonin has been implicated in a variety of developmental and physiological processes in peripheral tissues, including heart development, gastrointestinal movement, liver regeneration and mammary gland development (Lesurtel et al., 2006, Science, 312:104-107; Matsuda et al., 2004, Dev. Cell, 6:193-203; Nebigil et al., 2000, Proc. Natl. Acad. Sci. USA 97:9508-9513). To carry out its functions, serotonin can bind to at least 14 receptors, most of them being G-protein coupled receptors (GPCRs). One or several serotonin receptors are present in most cell types.

Mice genetically deficient for the TPH1 gene ("knockout mice") have been reported. In one case, the mice reportedly expressed normal amounts of serotonin in classical serotonergic brain regions, but largely lacked serotonin in the periphery. In another, the knockout mice exhibited abnormal cardiac activity, which was attributed to a lack of peripheral serotonin (Côté et al., 2003, Proc. Natl. Acad. Sci. USA 100:13525-13530).

International Patent Application No. PCT/US2009/038817, published as WO 2009/123978, the disclosure of which is incorporated herein in its entirety, is directed to methods of diagnosing, preventing, and treating bone mass diseases using therapeutic agents for lowering or increasing serum serotonin levels. International Patent Application No. PCT/US2009/064383, published as WO 2010/056992, the disclosure of which is incorporated herein in its entirety, is also directed to methods of diagnosing, preventing, and treating bone mass diseases using therapeutic agents for lowering or increasing serum serotonin levels.

LP-533401 is an inhibitor of TPH1 having the following structure:

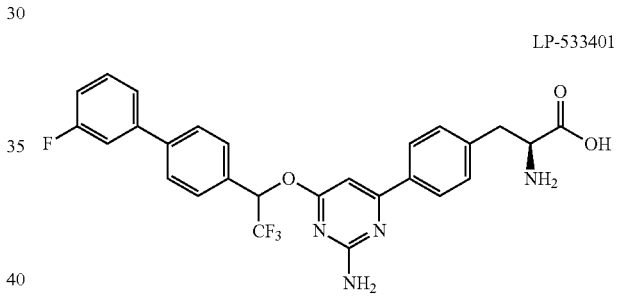

See, e.g., Liu et al., 2008, J. Pharmacol. Exp. Ther. 325: 47-55.

Other inhibitors of TPH1 are disclosed in International Patent Publications WO 09/123978; WO 10/056992; WO 08/073933; WO 09/002964; WO 09/002970; WO 09/009561; WO 09/014972; WO 09/029499; WO 09/042733; WO 09/048864; WO 10/065333; and WO 07/089335. Other disclosures of TPH1 inhibitors appear in U.S. Pat. No. 7,553,840 and U.S. Patent Application Publications Nos. US 2007/0191370; US 2008/0153852; US 2009/0005381; US 2009/0005382; US 2009/0029993; US 2009/0054308; US 2009/0062540; US 2009/0088447; and US 2009/0099206.

SUMMARY OF THE INVENTION

The present invention provides therapeutic agents that are inhibitors of tryptophan hydroxylase 1 (TPH1), the enzyme responsible for the first step of serotonin synthesis in enterochromaffin cells of the duodenum, for use in the treatment and/or prevention of diabetes. Also provided are pharmaceutical compositions comprising the therapeutic agents, for use in the treatment and/or prevention of diabetes.

It has been discovered that serum or plasma serotonin in mammals is involved in the control of blood glucose levels. Thus, in certain embodiments, the present invention provides a method of lowering blood glucose levels and thus treating or preventing diabetes in a patient known or suspected to be in need of such treatment or prevention comprising administering to the patient known or suspected to be in need of such treatment or prevention a therapeutically effective amount of a TPH1 inhibitor. In certain embodiments, the diabetes is Type II diabetes. In other embodiments, the diabetes is Type I diabetes.

Other methods disclosed herein are directed to diagnosing a person at risk of developing diabetes by determining if the person's blood glucose level is abnormally high compared to normal individuals, taking into account the age, gender, or other factors that affect blood glucose level (e.g. whether the person is in the fasting or fed state). Such a person at risk may be treated with therapeutic agents that decrease serum or plasma serotonin to prevent diabetes from developing, or to slow the development of diabetes. Those of skill in the art will understand that blood glucose levels may vary somewhat among individuals depending on certain factors and will be able to take those factors into account to determine whether a person has an abnormally high blood glucose level. Possible ranges which those skilled in the art may consider a person's blood glucose to be abnormally high may include blood glucose levels of greater than 90 mg/dl, greater than 100 mg/dl, greater than 110 mg/dl, greater than 120 mg/dl, greater than 130 mg/dl, greater than 140 mg/dl, or greater than 150 mg/dl.

Certain embodiments of the methods disclosed herein are directed to diagnosing a person at risk of developing diabetes by determining if the person's blood level of HbA1c is abnormally high compared to normal individuals, taking into account the age, gender, or other factors that affect HbA1c level. Such a person at risk may be treated with therapeutic agents that decrease serum or plasma serotonin to prevent diabetes from developing, or to slow the development of diabetes. Those of skill in the art will understand that blood HbA1c levels may vary somewhat among individuals depending on certain factors and will be able to take those factors into account to determine whether a person has an abnormally high blood HbA1c level. Possible ranges which those skilled in the art may consider a person's blood HbA1c to be abnormally high may include above 48 mM or above 6.0%.

In one aspect, the present invention provides a method of treating or preventing Type II diabetes in a patient known or suspected to be in need of such treatment or prevention comprising administering to the patient known or suspected to be in need of such treatment or prevention a therapeutically effective amount of a therapeutic agent that lowers the level of serum or plasma serotonin.

In one embodiment, the present invention provides a method of treating or preventing Type II diabetes in a patient known or suspected to be in need of such treatment or prevention comprising administering to the patient known or suspected to be in need of such treatment or prevention a therapeutically effective amount of a TPH1 inhibitor. In preferred embodiments, the therapeutic agent is a TPH1 inhibitor that does not cross the blood brain barrier. In other embodiments, the therapeutic agent is a TPH1 inhibitor that does not significantly inhibit TPH2.

In certain embodiments, the TPH1 inhibitor is selected from the following or from pharmaceutically acceptable salts and/or solvates thereof:

(1)

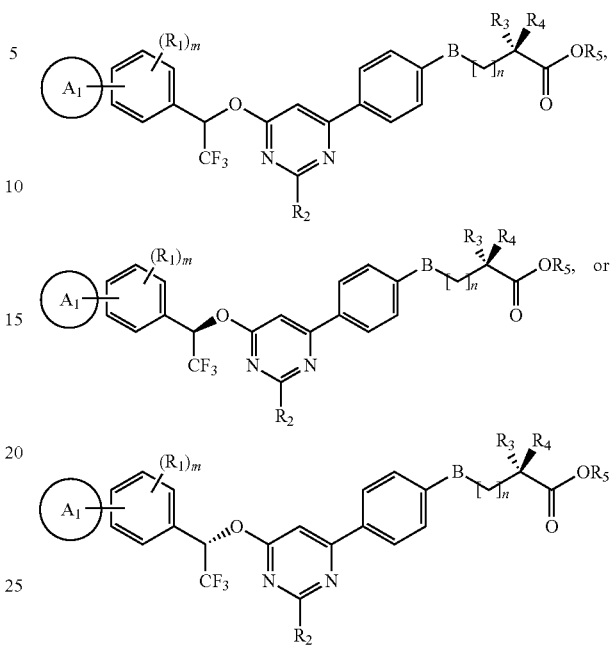

where $A_1$ is optionally substituted heterocycle or 3-fluorophenyl; B is O, N, or —$CH_2$—; each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is halogen, hydrogen, $C(O)R_A$, $OR_A$, $NR_BR_C$, $S(O_2)R_A$, or optionally substituted alkyl, alkyl-aryl or alkyl-heterocycle; either $R_3$ is $NHR_6$ and $R_4$ is hydrogen or, alternatively, $R_3$ and $R_4$ together form =O; $R_5$ is hydrogen or optionally substituted alkyl, alkyl-aryl, alkyl-heterocycle, aryl, or heterocycle; $R_6$ is hydrogen, $C(O)R_A$, $C(O)OR_A$, or optionally substituted alkyl, alkyl-aryl, alkyl-heterocycle, aryl, or heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; m is 0-4; and n is 0 or 1.

(2)

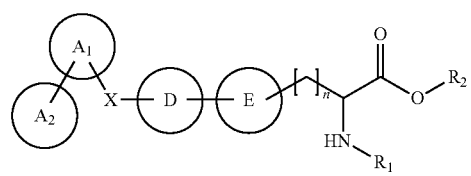

where each of $A_1$ and $A_2$ is independently a monocyclic optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; and n is 0-3.

Compounds encompassed by the formula immediately above include those wherein $A_1$ and/or $A_2$ is optionally substituted cycloalkyl (e.g., 6-membered and 5-membered). In some, $A_1$ and/or $A_2$ is optionally substituted aryl (e.g., phenyl or naphthyl). In others, $A_1$ and/or $A_2$ is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, $A_1$ and/or $A_2$ is aromatic. In others, $A_1$ and/or $A_2$ is not aromatic.

Particular compounds include those wherein D is optionally substituted aryl (e.g., phenyl or naphthyl). In others, D is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, D is aromatic. In others, D is not aromatic. In some, D is an optionally substituted bicyclic moiety (e.g., indole, iso-indole, pyrrolo-pyridine, or napthylene).

Particular compounds include those wherein E is optionally substituted aryl (e.g., phenyl or naphthyl). In others, E is optionally substituted heterocycle (e.g., 6-membered and 5-membered). Examples of 6-membered heterocycles include pyridine, pyridazine, pyrimidine, pyrazine, and triazine. Examples of 5-membered heterocycles include pyrrole, imidazole, triazole, thiazole, thiophene, and furan. In some compounds, E is aromatic. In others, E is not aromatic. In some, E is an optionally substituted bicyclic moiety (e.g., indole, iso-indole, pyrrolo-pyridine, or napthylene).

Particular compounds include those wherein $R_1$ is hydrogen or optionally substituted alkyl.

In some compounds, $R_2$ is hydrogen or optionally substituted alkyl.

In some compounds, n is 1 or 2.

In some compounds, X is a bond or S. In others, X is $-C(R_4)=$, $=C(R_4)-$, $-C(R_3R_4)-$, $-C(R_4)=C(R_4)-$, or $-C\equiv C-$, and, for example, $R_4$ is independently hydrogen or optionally substituted alkyl. In others, X is $-O-$, $-C(R_3R_4)O-$, or $-OC(R_3R_4)-$, and, for example, $R_3$ is hydrogen or optionally substituted alkyl, and $R_4$ is hydrogen or optionally substituted alkyl. In some, $R_3$ is hydrogen and $R_4$ is trifluoromethyl. In some compounds, X is $-S(O_2)-$, $-S(O_2)N(R_5)-$, $-N(R_5)S(O_2)-$, $-C(R_3R_4)S(O_2)-$, or $-S(O_2)C(R_3R_4)-$, and, for example, $R_3$ is hydrogen or optionally substituted alkyl, $R_4$ is hydrogen or optionally substituted alkyl, and $R_5$ is hydrogen or optionally substituted alkyl. In others, X is $-N(R_5)-$, $-N(R_5)C(O)N(R_5)-$, $-C(R_3R_4)N(R_5)-$, or $-N(R_5)C(R_3R_4)-$, and, for example, $R_3$ is hydrogen or optionally substituted alkyl, $R_4$ is hydrogen or optionally substituted alkyl, and each $R_5$ is independently hydrogen or optionally substituted alkyl.

(3)

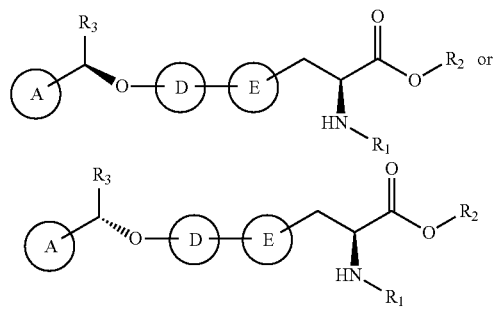

where A is optionally substituted cycloalkyl, aryl, or heterocycle; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; and $R_3$ is trifluoromethyl.

(4)

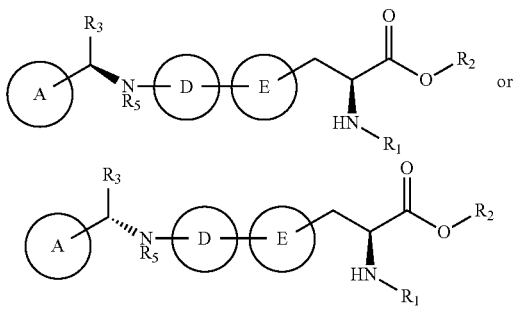

where A is optionally substituted cycloalkyl, aryl, or heterocycle; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen; and $R_5$ is optionally substituted alkyl or aryl.

(5)

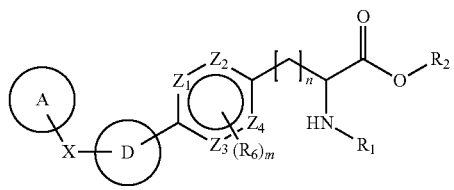

where A is optionally substituted cycloalkyl, aryl, or heterocycle; X is a bond (i.e., A is directly bound to D), $-O-$, $-S-$, $-C(O)-$, $-C(R_4)=$, $=C(R_4)-$, $-C(R_3R_4)-$, $-C(R_4)=C(R_4)-$, $-C\equiv C-$, $-N(R_5)-$, $-N(R_5)C(O)N(R_5)-$, $-C(R_3R_4)N(R_5)-$, $-N(R_5)C(R_3R_4)-$, $-ONC(R_3)-$, $-C(R_3)NO-$, $-C(R_3R_4)O-$, $-OC(R_3R_4)-$, $-S(O_2)-$, $-S(O_2)N(R_5)-$, $-N(R_5)S(O_2)-$, $-C(R_3R_4)S(O_2)-$, or $-S(O_2)C(R_3R_4)-$; D is optionally substituted aryl or heterocycle; each of $Z_1$, $Z_2$, $Z_3$, and $Z_4$ is independently N or $CR_6$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_6$ is independently hydrogen, cyano, halogen, $OR_7$, $NR_8R_9$, amino, hydroxyl, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; m is 1-4; and n is 1-3.

(6)

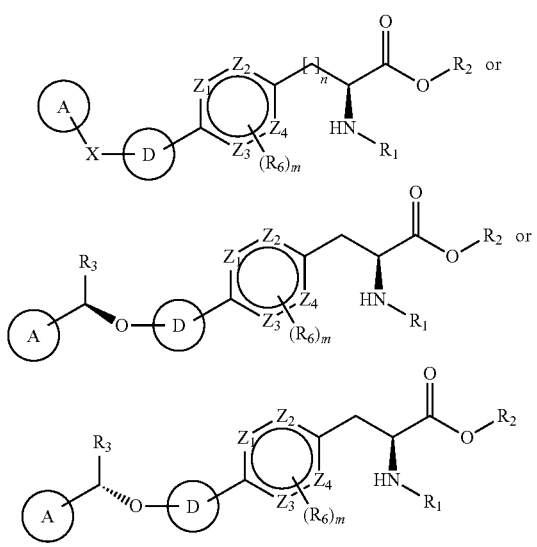

where A is optionally substituted cycloalkyl, aryl, or heterocycle; X is a bond (i.e., A is directly bound to D), —O—, —S—, —C(O)—, —C($R_4$)—, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; each of $Z_1$, $Z_2$, $Z_3$, and $Z_4$ is independently N or $CR_6$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is trifluoromethyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_6$ is independently hydrogen, cyano, halogen, $OR_7$, $NR_8R_9$, amino, hydroxyl, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; m is 1-4; and n is 1-3.

(7)

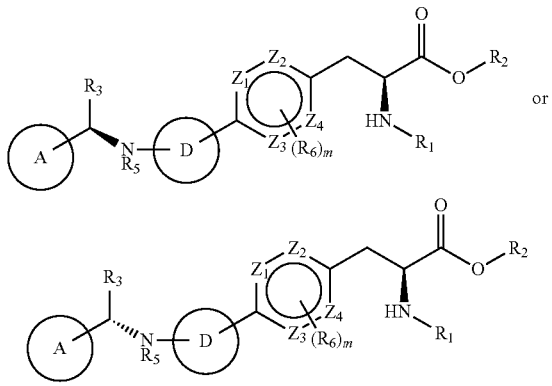

where A is optionally substituted cycloalkyl, aryl, or heterocycle; D is optionally substituted aryl or heterocycle; each of $Z_1$, $Z_2$, $Z_3$, and $Z_4$ is independently N or $CR_6$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen; $R_5$ is hydrogen or optionally substituted alkyl or aryl; each $R_6$ is independently hydrogen, cyano, halogen, $OR_7$, $NR_8R_9$, amino, hydroxyl, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; and m is 1-4.

Some compounds are such that all of $Z_1$, $Z_2$, $Z_3$, and $Z_4$ are N. In others, only three of $Z_1$, $Z_2$, $Z_3$, and $Z_4$ are N. In others, only two of $Z_1$, $Z_2$, $Z_3$, and $Z_4$ are N. In others, only one of $Z_1$, $Z_2$, $Z_3$, and $Z_4$ is N. In others, none of $Z_1$, $Z_2$, $Z_3$, and $Z_4$ are N.

(8)

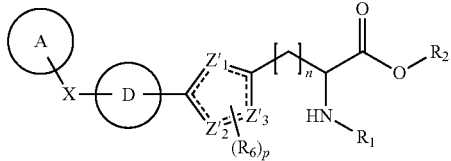

where A is optionally substituted cycloalkyl, aryl, or heterocycle; X is a bond (i.e., A is directly bound to D), —O—, —S—, —C(O)—, —C($R_4$)—, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; each of $Z'_1$, $Z'_2$, and $Z'_3$, is independently N, NH, S, O or $CR_6$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_6$ is independently amino, cyano, halogen, hydrogen, $OR_7$, $SR_7$, $NR_8R_9$, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; n is 1-3; and p is 1-3.

(9)

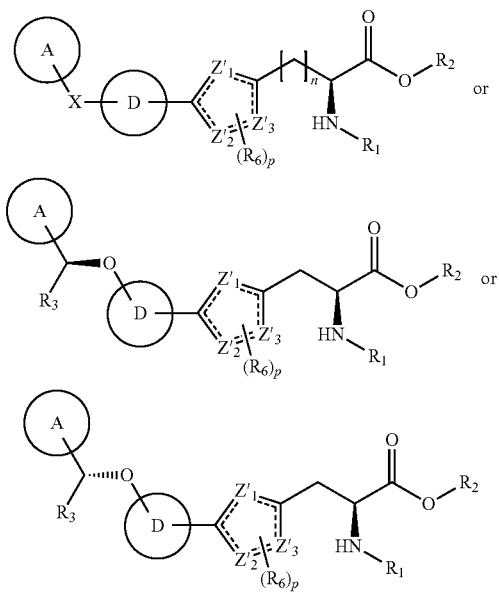

where A is optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, or —S($O_2$)C($R_3R_4$)—; D is optionally substituted aryl or heterocycle; each of $Z'_1$, $Z'_2$, and $Z'_3$, is independently N, NH, S, O or $CR_6$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl or aryl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_6$ is independently amino, cyano, halogen, hydrogen, $OR_7$, $SR_7$, $NR_8R_9$, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; n is 1-3; and p is 1-3.

(10)

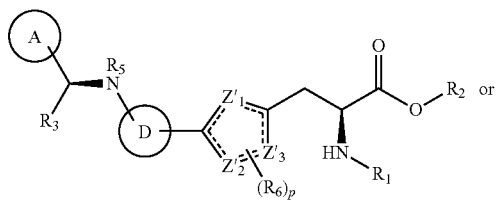

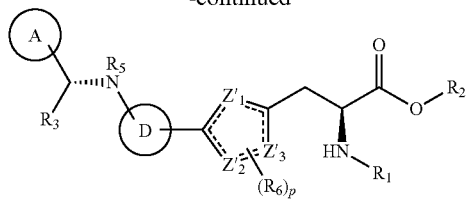

where A is optionally substituted cycloalkyl, aryl, or heterocycle; D is optionally substituted aryl or heterocycle; each of $Z'_1$, $Z'_2$, and $Z'_3$, is independently N, NH, S, O or $CR_6$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen; $R_5$ is hydrogen or optionally substituted alkyl or aryl; each $R_6$ is independently amino, cyano, halogen, hydrogen, $OR_7$, $SR_7$, $NR_8R_9$, or optionally substituted alkyl, alkyl-aryl or alkyl-heterocycle; each $R_7$ is independently hydrogen or optionally substituted alkyl, alkyl-aryl or alkyl-heterocycle; each $R_8$ is independently hydrogen or optionally substituted alkyl, alkyl-aryl or alkyl-heterocycle; each $R_9$ is independently hydrogen or optionally substituted alkyl, alkyl-aryl or alkyl-heterocycle; and p is 1-3.

Some compounds are such that all of $Z'_1$, $Z'_2$, and $Z'_3$ are N or NH. In others, only two of $Z'_1$, $Z'_2$, and $Z'_3$ are N or NH. In others, only one of $Z'_1$, $Z'_2$, and $Z'_3$ is N or NH. In others, none of $Z'_1$, $Z'_2$, and $Z'_3$ are N or NH.

(11)

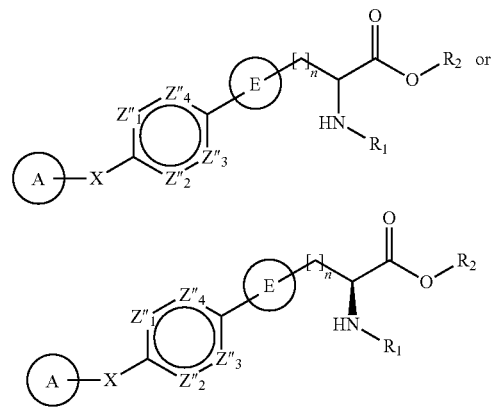

where A is optionally substituted cycloalkyl, aryl, or heterocycle; E is optionally substituted aryl or heterocycle; X is a bond, —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; each $R_{13}$ is independently hydrogen or optionally substituted alkyl, alkyl-aryl or alkyl-heterocycle; and n is 1-3.

(12)

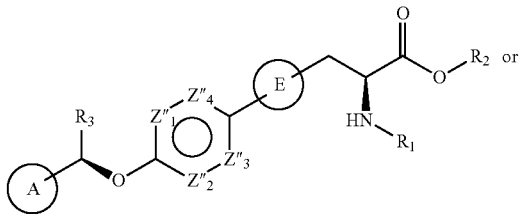

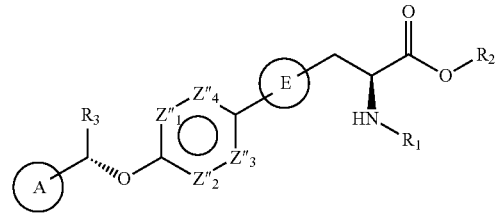

where A is optionally substituted cycloalkyl, aryl, or heterocycle; E is optionally substituted aryl or heterocycle; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is trifluoromethyl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; and each $R_{13}$ is independently hydrogen or optionally substituted alkyl, alkyl-aryl or alkyl-heterocycle.

(13)

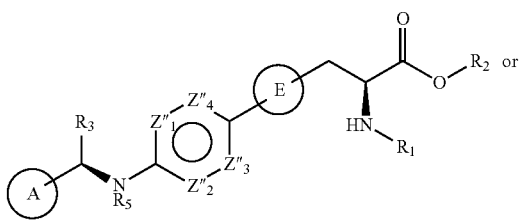

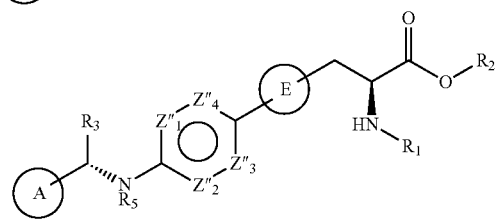

where A is optionally substituted cycloalkyl, aryl, or heterocycle; E is optionally substituted aryl or heterocycle; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen; $R_5$ is hydrogen or optionally substituted alkyl or aryl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; and each $R_{13}$ is independently hydrogen or optionally substituted alkyl, alkyl-aryl or alkyl-heterocycle.

Some compounds are such that all of $Z''_1$, $Z''_2$, $Z''_3$, and $Z''_4$ are N. In others, only three of $Z''_1$, $Z''_2$, $Z''_3$, and $Z''_4$ are N. In others, only two of $Z''_1$, $Z''_2$, $Z''_3$, and $Z''$ are N. In others, only one of $Z''_1$, $Z''_2$, $Z''_3$, and $Z''$ is N. In others, none of $Z''_1$, $Z''_2$, $Z''_3$, and $Z''_4$ are N.

(14)

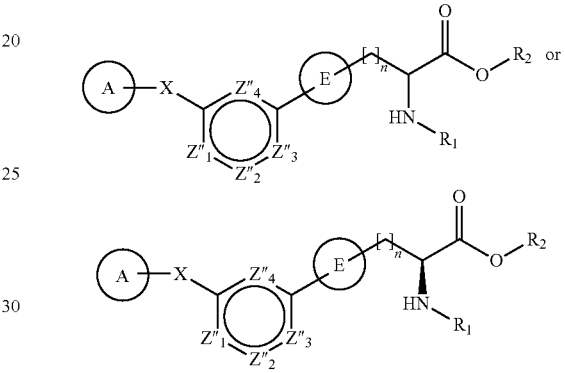

where A is optionally substituted cycloalkyl, aryl, or heterocycle; E is optionally substituted aryl or heterocycle; X is a bond, —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; each $R_{13}$ is independently hydrogen or optionally substituted alkyl, alkyl-aryl or alkyl-heterocycle; and n is 1-3.

(15)

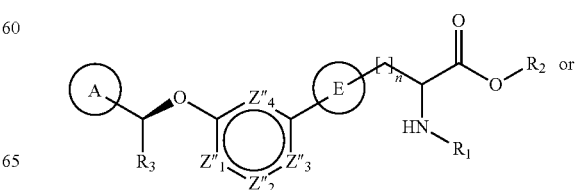

(17)

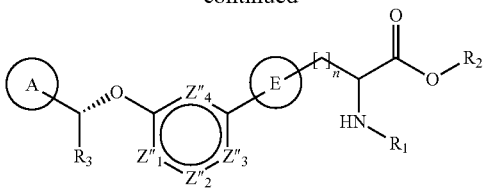

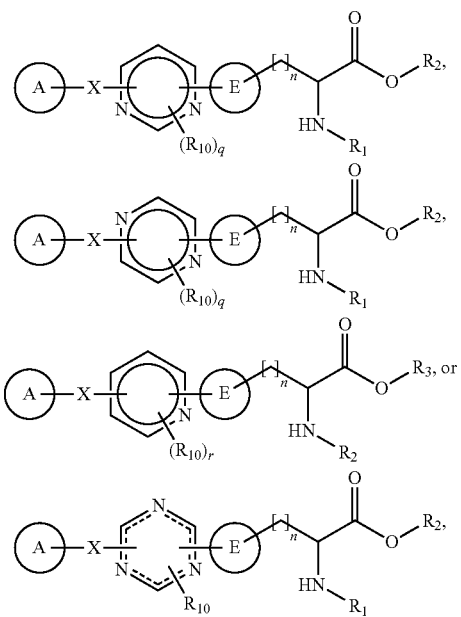

where A is optionally substituted cycloalkyl, aryl, or heterocycle; E is optionally substituted aryl or heterocycle; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is trifluoromethyl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; and each $R_{13}$ is independently hydrogen or optionally substituted alkyl, alkyl-aryl or alkyl-heterocycle.

(16)

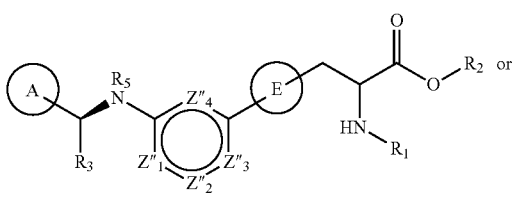

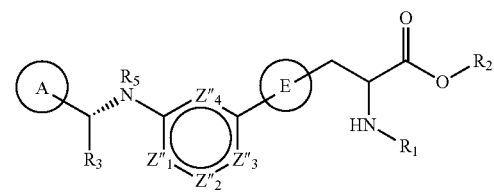

where A is optionally substituted cycloalkyl, aryl, or heterocycle; E is optionally substituted aryl or heterocycle; each of $Z''_1$, $Z''_2$, $Z''_3$, and $Z''_4$ is independently N or $CR_{10}$; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen; $R_5$ is hydrogen or optionally substituted alkyl or aryl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; and each $R_{13}$ is independently hydrogen or optionally substituted alkyl, alkyl-aryl or alkyl-heterocycle.

Some compounds are such that all of $Z''_1$, $Z''_2$, $Z''_3$, and $Z''_4$ are N. In others, only three of $Z''_1$, $Z''_2$, $Z''_3$, and $Z''_4$ are N. In others, only two of $Z''_1$, $Z''_2$, $Z''_3$, and $Z''_4$ are N. In others, only one of $Z''_1$, $Z''_2$, $Z''_3$, and $Z''_4$ is N. In others, none of $Z''_1$, $Z''_2$, $Z''_3$, and $Z''_4$ are N.

where A is optionally substituted cycloalkyl, aryl, or heterocycle; E is optionally substituted aryl or heterocycle; X is a bond, —O—, —S—, —C(O)—, —$C(R_4)$=, =$C(R_4)$—, —$C(R_3R_4)$—, —$C(R_4)$=$C(R_4)$—, —C≡C—, —$N(R_5)$—, —$N(R_5)C(O)N(R_5)$—, —$C(R_3R_4)N(R_5)$—, —$N(R_5)C(R_3R_4)$—, —$ONC(R_3)$—, —$C(R_3)NO$—, —$C(R_3R_4)O$—, —$OC(R_3R_4)$—, —$S(O_2)$—, —$S(O_2)N(R_5)$—, —$N(R_5)S(O_2)$—, —$C(R_3R_4)S(O_2)$—, or —$S(O_2)C(R_3R_4)$—; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; each $R_3$ is independently hydrogen, alkoxy, amino, cyano, halogen, hydroxyl, or optionally substituted alkyl; each $R_4$ is independently hydrogen, alkoxy, amino, cyano, halogen, hydroxyl, or optionally substituted alkyl or aryl; each $R_5$ is independently hydrogen or optionally substituted alkyl or aryl; each $R_{10}$ is independently amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; each $R_{12}$ is independently hydrogen or optionally substituted alkyl, alkyl-aryl or alkyl-heterocycle; each $R_{13}$ is independently hydrogen or optionally substituted alkyl, alkyl-aryl or alkyl-heterocycle; n is 1-3; q is 0-2; and r is 0-2.

(18)

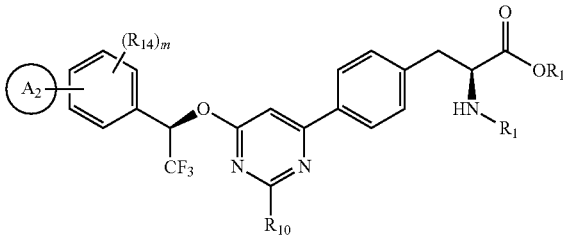

where $A_2$ is optionally substituted cycloalkyl, aryl, or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_{10}$ is amino, cyano, halogen, hydrogen, $OR_{11}$, $SR_{11}$, $NR_{12}R_{13}$, or optionally substituted alkyl, alkyl-aryl or alkyl-heterocycle; each $R_{11}$ is independently hydrogen or optionally substituted alkyl, alkyl-aryl or alkyl-heterocycle; $R_{12}$ is hydrogen or optionally substituted alkyl, alkyl-aryl or alkyl-heterocycle; $R_{13}$ is hydrogen or optionally substituted alkyl, alkyl-aryl or alkyl-heterocycle; each $R_{14}$ is independently amino, halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; and m is 1-4.

(19)

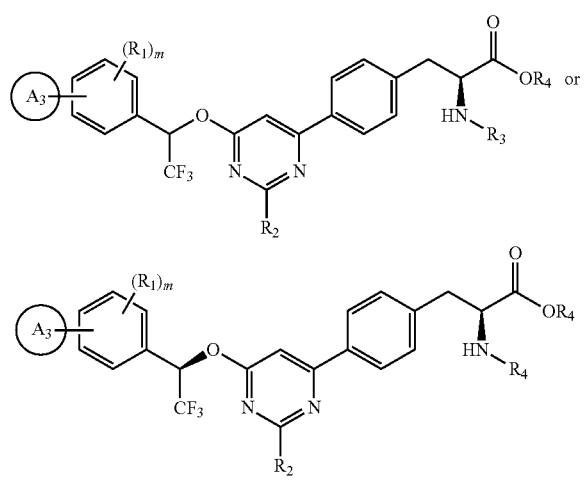

where $A_1$ is optionally substituted heterocycle; each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; and m is 1-4.

(20)

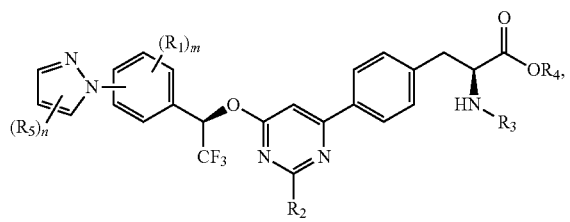

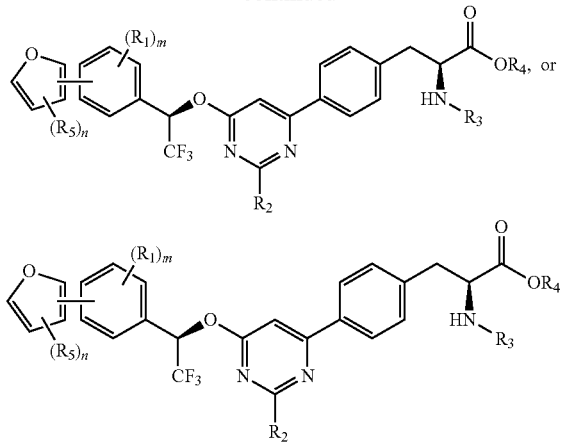

where each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_5$ is independently halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; m is 1-4; and n is 1-3.

(21)

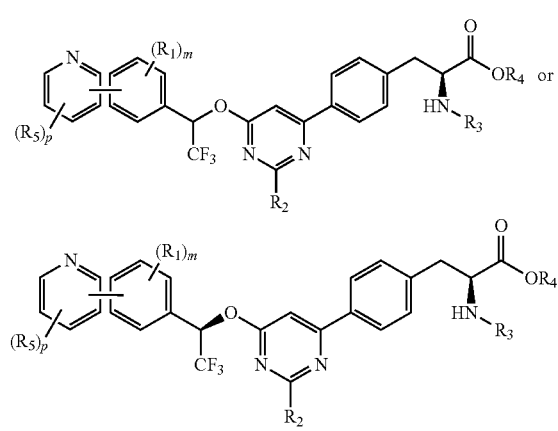

where each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_5$ is independently halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; m is 1-4; and p is 1-3.

(22)

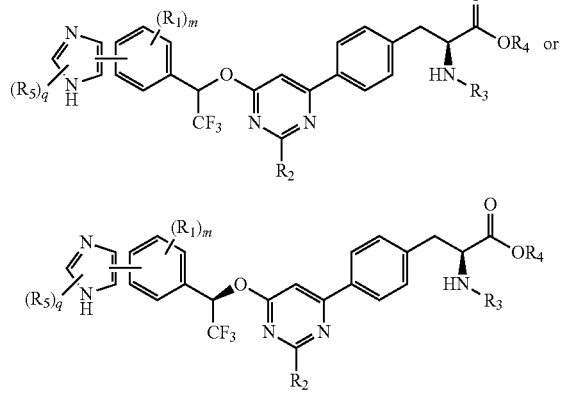

where each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_5$ is independently halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; m is 1-4; and q is 1-2.

(23)

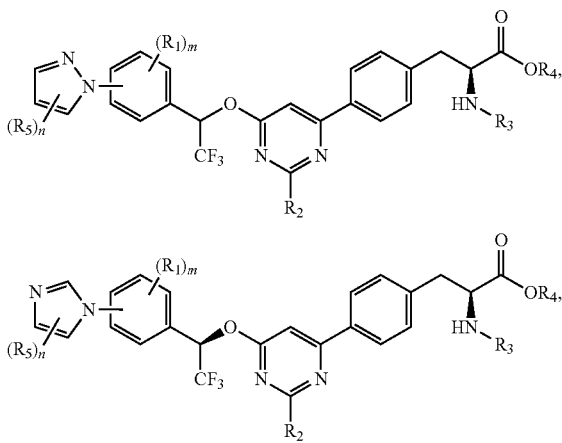

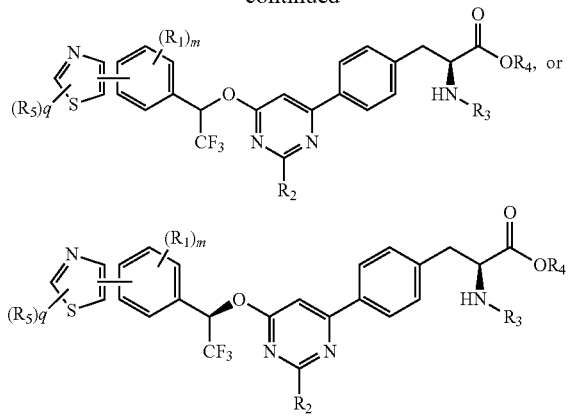

where each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_5$ is independently halogen, hydrogen, $C(O)R_A$, $OR_A$, $NR_BR_C$, $S(O_2)R_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; m is 1-4; n is 1-3; and q is 1-2.

In particular compounds above, $A_1$ is aromatic. In others, $A_1$ is not aromatic. In some, $A_1$ is optionally substituted with one or more of halogen or lower alkyl.

In some, $R_1$ is hydrogen or halogen.

In some, m is 1.

In some, $R_2$ is hydrogen or amino.

In some, $R_3$ is hydrogen or lower alkyl. In others, $R_3$ is $C(O)OR_A$ and $R_A$ is alkyl.

In some, $R_4$ is hydrogen or lower alkyl.

In some, $R_5$ is hydrogen or lower alkyl (e.g., methyl).

In some, n is 1.

In some, p is 1.

In some, q is 1.

(24)

(S)-2-Amino-3-(4-{2-amino-6-[2,2,2-trifluoro-1-(4-pyridin-4-yl-phenyl)-ethoxy]-pyrimidin-4-yl}-phenyl)-propionic acid

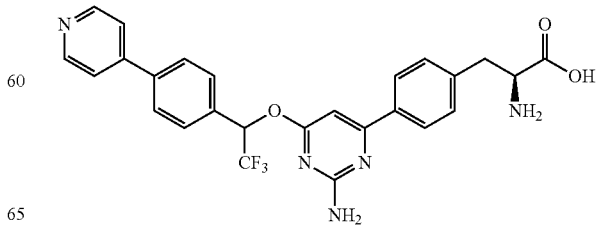

(25)
(S)-2-Amino-3-(4-{6-[2,2,2-trifluoro-1-(2-pyridin-4-yl-phenyl)-ethoxy]-pyrimidin-4-yl}-phenyl)-propionic acid

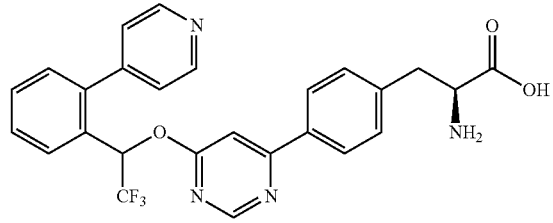 [SMILES: N[C@@H](Cc1ccc(-c2cc(OC(c3ccccc3-c3ccncc3)C(F)(F)F)ncn2)cc1)C(=O)O]

(26)
(S)-2-Amino-3-(4-{2-amino-6-[2,2,2-trifluoro-1-(2-(4-methylthiophen-3-yl)-phenyl]-ethoxy}-pyrimidin-4-yl)-phenyl]-propionic acid

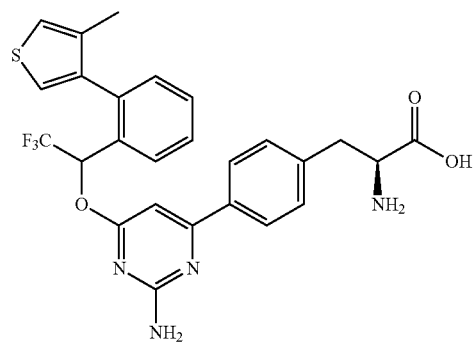 [SMILES: Cc1cscc1-c1ccccc1C(Oc1cc(-c2ccc(C[C@H](N)C(=O)O)cc2)nc(N)n1)C(F)(F)F]

(27)
(S)-2-Amino-3-(4-{2-amino-6-[2,2,2-trifluoro-1-(2-(5-methyl-thiophen-3-yl-)-phenyl]-ethoxy}-pyrimidin-4-yl)-phenyl]-propionic acid

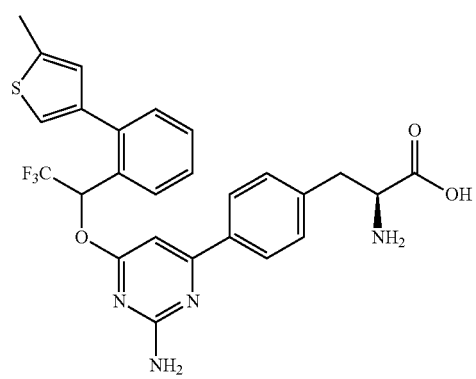 [SMILES: Cc1cc(-c2ccccc2C(Oc2cc(-c3ccc(C[C@H](N)C(=O)O)cc3)nc(N)n2)C(F)(F)F)cs1]

(28)
(S)-2-Amino-3-(4-{2-amino-6-[2,2,2-trifluoro-1-(4-furan-3-yl-phenyl)-ethoxy]-pyrimidin-4-yl}-phenyl)-propionic acid

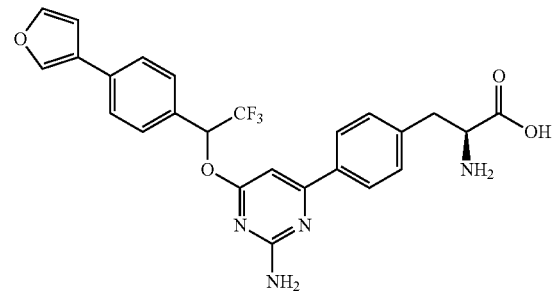 [SMILES: Nc1nc(OC(c2ccc(-c3ccoc3)cc2)C(F)(F)F)cc(-c2ccc(C[C@H](N)C(=O)O)cc2)n1]

(29)
(S)-2-Amino-3-[4-{2-amino-6-{1-[2-(5-dimethylaminomethyl-furan-2-yl)-phenyl]-2,2,2-trifluoro-ethoxy}-pyrimidin-4-yl)-phenyl]-propionic acid

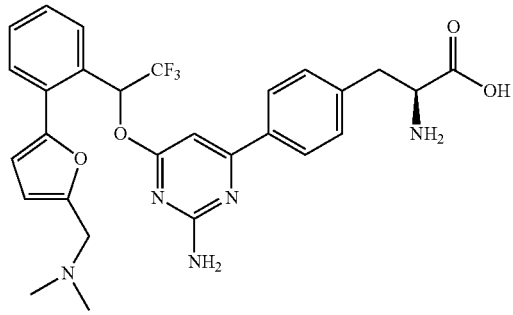 [SMILES: CN(C)Cc1ccc(-c2ccccc2C(Oc2cc(-c3ccc(C[C@H](N)C(=O)O)cc3)nc(N)n2)C(F)(F)F)o1]

(30)
(S)-2-Amino-3[4-(2-amino-6-{1-[2-(6-cyano-pyridin-3-yl)-phenyl]-2,2,2-tri-fluoro-ethoxy}-pyrimidin-4-yl)-phenyl]-propionic acid

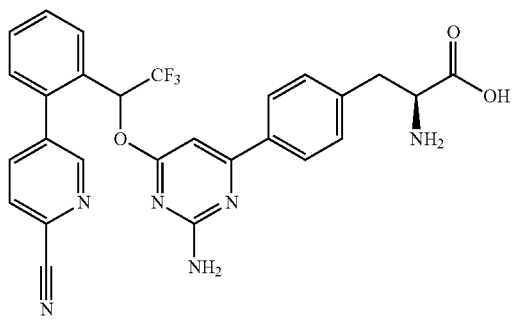 [SMILES: N#Cc1ccc(-c2ccccc2C(Oc2cc(-c3ccc(C[C@H](N)C(=O)O)cc3)nc(N)n2)C(F)(F)F)cn1]

(31)
(S)-2-Amino-3-(4-{2-amino-6-[2,2,2-trifluoro-1-(2-imidazol-1-yl-phenyl)-ethoxy]-pyrimidin-4-yl}-phenyl)-propionic acid

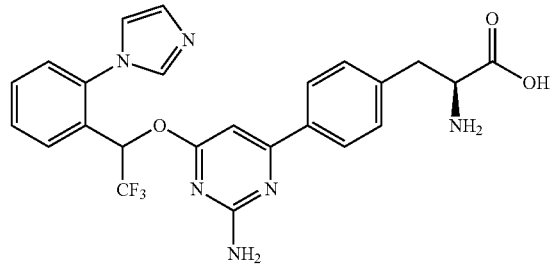 [SMILES: Nc1nc(OC(c2ccccc2-n2ccnc2)C(F)(F)F)cc(-c2ccc(C[C@H](N)C(=O)O)cc2)n1]

(32)
(S)-2-Amino-3-(4-{6-[2,2,2-trifluoro-1-(2-pyrazol-1-yl-phenyl)-ethoxy]-pyrimidin-4-yl}-phenyl)-propionic acid

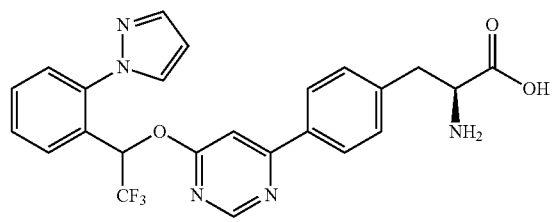 [SMILES: N[C@@H](Cc1ccc(-c2cc(OC(c3ccccc3-n3cccn3)C(F)(F)F)ncn2)cc1)C(=O)O]

(33)
(S)-2-amino-3-[4-(2-amino-6-{2,2,2-trifluoro-1-[2-(3-trifluoromethyl-pyrazol-1-yl)-phenyl]-ethoxy}-pyrimidin-4-yl)-phenyl]-propionic acid

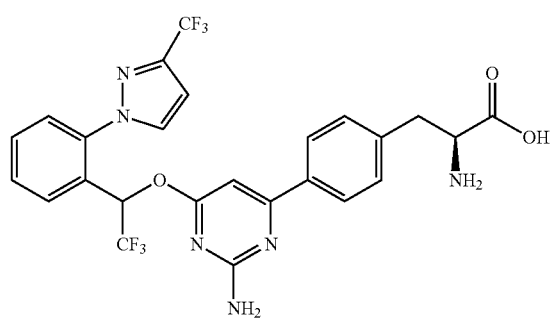 [SMILES: Nc1nc(OC(c2ccccc2-n2ccc(C(F)(F)F)n2)C(F)(F)F)cc(-c2ccc(C[C@H](N)C(=O)O)cc2)n1]

(34)
(S)-2-Amino-3-[4-(2-amino-6-{1-[2-(3,5-dimethyl-pyrazol-1-yl)-phenyl]-2,2,2-trifluoro-ethoxy}-pyrimidin-4-yl)-phenyl]-propionic acid

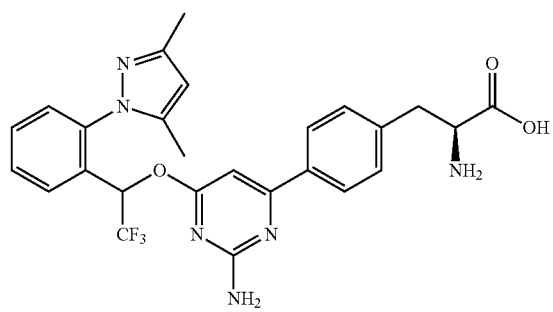 [SMILES: Cc1cc(C)n(-c2ccccc2C(Oc2cc(-c3ccc(C[C@H](N)C(=O)O)cc3)nc(N)n2)C(F)(F)F)n1]

(35)
(S)-2-Amino-3-[4-(2-amino-6-{2,2,2-trifluoro-1-[2-(3-phenyl-pyrazol-1-yl)-phenyl]-ethoxy}-pyrimidin-4-yl)-phenyl]-propionic acid

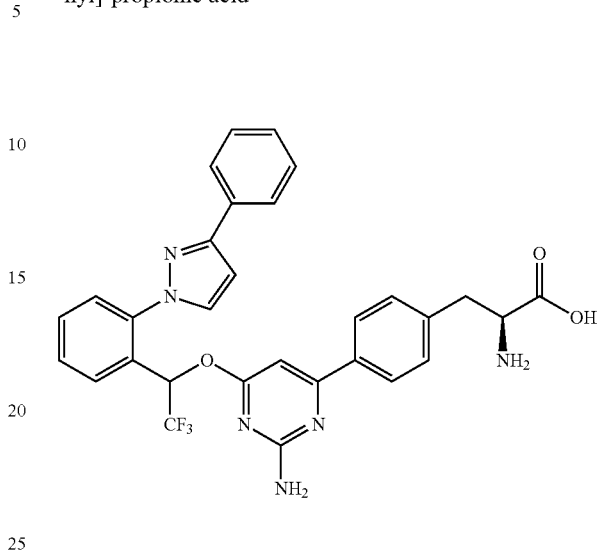

(36)
(S)-2-Amino-3-[4-(2-amino-6-{2,2,2-trifluoro-1-[5-methoxy-2-(4-methyl-pyrazol-1-yl)-phenyl]-ethoxy}-pyrimidin-4-yl)-phenyl]-propionic acid

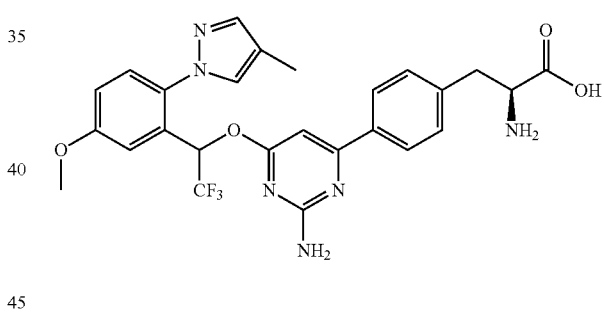

(37)
(S)-2-amino-3-[4-(2-amino-6-{(R)-2,2,2-trifluoro-1-[2-(3-methyl-pyrazol-1-yl)-phenyl]-ethoxy}-pyrimidin-4-yl)-phenyl]-propionic acid

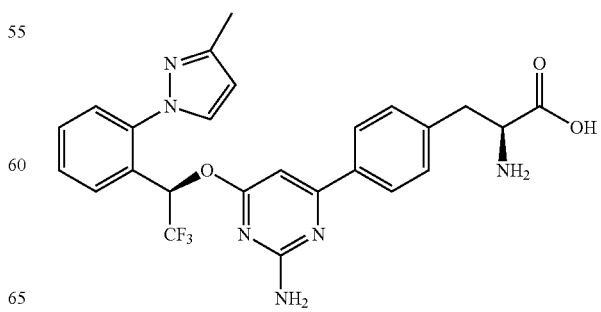

(38)
(S)-2-amino-3-[4-(2-amino-6-{1-[4-chloro-2-(3-methyl-pyrazol-1-yl)-phenyl-]-2,2,2-trifluoro-ethoxy}-pyrimidin-4-yl)-phenyl]-propionic acid

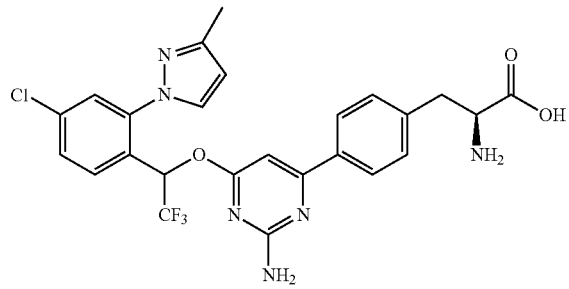 [SMILES: Cc1ccn(-c2cc(Cl)ccc2C(Oc2cc(-c3ccc(C[C@H](N)C(=O)O)cc3)nc(N)n2)C(F)(F)F)n1]

(39)
(S)-2-Amino-3-[4-(2-amino-6-{R-1-[4-chloro-2-(3-methyl-pyrazol-1-yl)-phenyl]-2,2,2-trifluoro-ethoxy}-pyrimidin-4-yl)-phenyl]-propionic acid ethyl ester

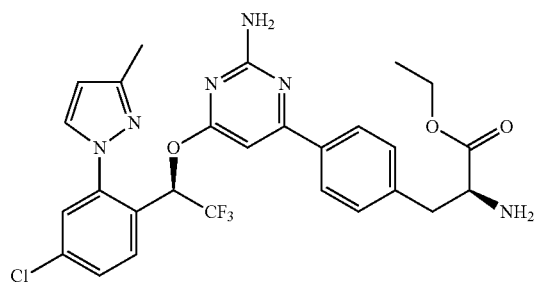 [SMILES: CCOC(=O)[C@@H](N)Cc1ccc(-c2cc(O[C@H](c3ccc(Cl)cc3-n3ccc(C)n3)C(F)(F)F)nc(N)n2)cc1]

(40)
(S)-2-amino-3-(4-(2-amino-6-((R)-1-(4-chloro-2-(3-methyl-1H-pyrazol-1-yl)-phenyl)-2,2,2-trifluoroethoxy)pyrimidin-4-yl)phenyl)propanoic acid

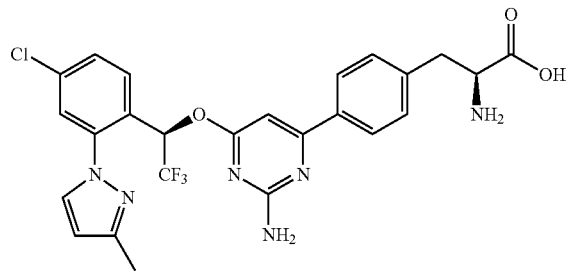 [SMILES: Cc1ccn(-c2cc(Cl)ccc2[C@@H](Oc2cc(-c3ccc(C[C@H](N)C(=O)O)cc3)nc(N)n2)C(F)(F)F)n1]

(41)
(S)-2-Amino-3-(4-{2-amino-6-[2,2,2-trifluoro-1-(2-thiazol-2-yl-phenyl)-ethoxy]-pyrimidin-4-yl}-phenyl)-propionic acid

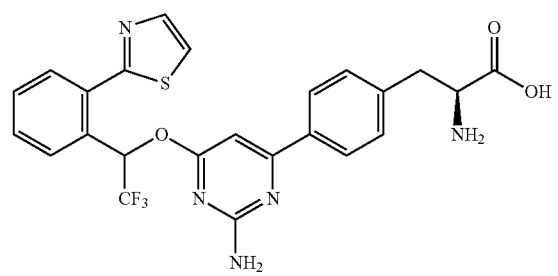 [SMILES: Nc1nc(OC(c2ccccc2-c2nccs2)C(F)(F)F)cc(-c2ccc(C[C@H](N)C(=O)O)cc2)n1]

(42)
(S)-2-Amino-3-[4-(2-amino-6-{2,2,2-trifluoro-1-[2-(pyridin-3-yloxy)-phenyl-1}-ethoxy]-pyrimidin-4-yl)-phenyl]-propionic acid

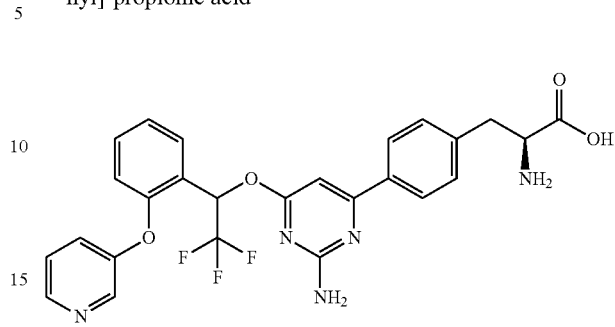

(43)
(S)-2-Amino-3-[4-(2-amino-6-{2,2,2-trifluoro-1-[4-(pyridin-3-yloxy)-phenyl]-ethoxy}-pyrimidin-4-yl)-phenyl]-propionic acid

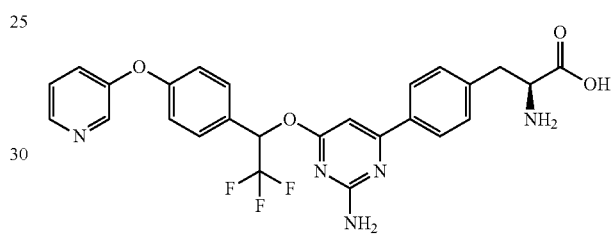

(44)
(S)-2-Amino-3-[4-(6-{2,2,2-trifluoro-1-[4-(pyridin-3-yloxy)-phenyl]-ethoxy}-pyrimidin-4-yl)-phenyl]-propionic acid

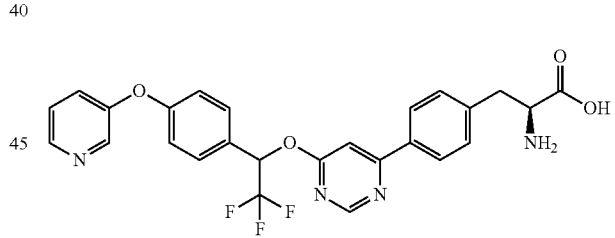

(45)
(S)-2-Amino-3-(4-{2-amino-6-[2,2,2-trifluoro-1-(4-thiophen-2-yl-phenyl)-ethoxy]-pyrimidin-4-yl}-phenyl)-propionic acid

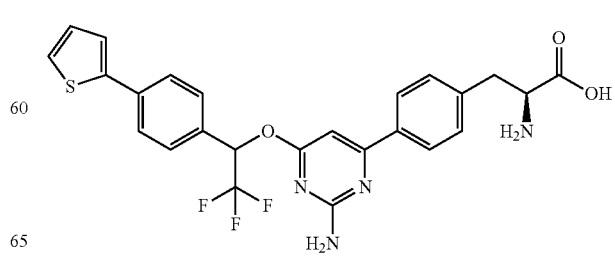

(46)
(S)-2-Amino-3-(4-{6-[2,2,2-trifluoro-1-(4-imidazol-1-yl-phenyl)-ethoxy]-pyrimidin-4-yl}-phenyl)-propionic acid

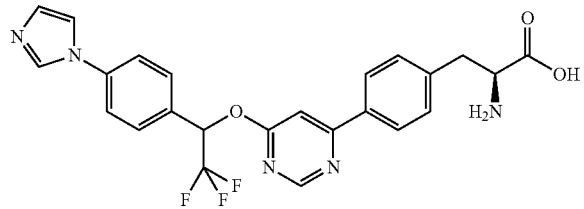 [SMILES: N[C@@H](Cc1ccc(-c2cc(OC(c3ccc(-n4ccnc4)cc3)C(F)(F)F)ncn2)cc1)C(=O)O]

(47)
(S)-2-Amino-3-(4-{2-amino-6-[2,2,2-trifluoro-1-(4-[1,2,4]triazol-1-yl-phenyl)-ethoxy]-pyrimidin-4-yl}-phenyl)-propionic acid

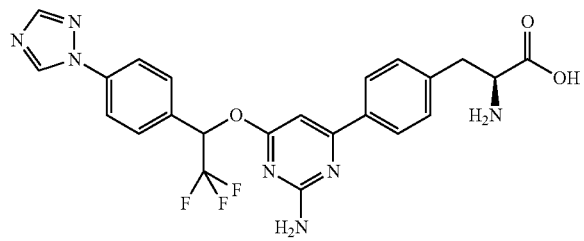 [SMILES: Nc1nc(OC(c2ccc(-n3cncn3)cc2)C(F)(F)F)cc(-c2ccc(C[C@H](N)C(=O)O)cc2)n1]

(48)
(S)-2-Amino-3-(4-{2-amino-6-[2,2,2-trifluoro-1-(4-fluoro-2-thiophen-3-yl-phenyl)ethoxy]-pyrimidin-4-yl}-phenyl)-propionic acid

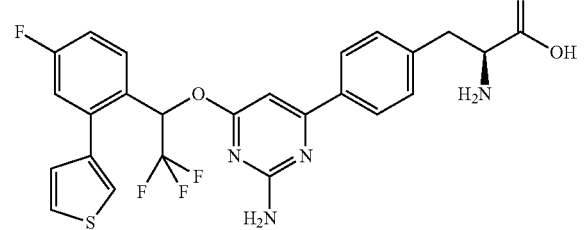

(49)
(S)-2-Amino-3-[4-(2-amino-6-{2,2,2-trifluoro-1-[4-fluoro-2-(4-methyl-thiophen-2-yl)-phenyl]-ethoxy}-pyrimidin-4-yl)-phenyl]-propionic acid

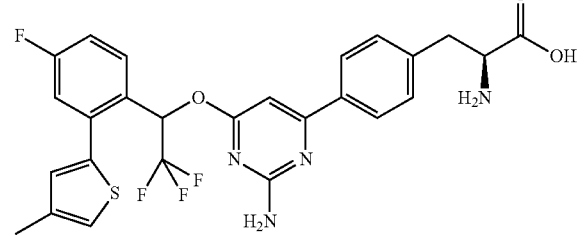

(50)
(S)-2-Amino-3-[4-(2-amino-6-{1-[2-(3,5-dimethyl-isoxazol-4-yl)-4-fluoro-phenyl]-2,2,2-trifluoro-ethoxy}-pyrimidin-4-yl)-phenyl]-propionic acid

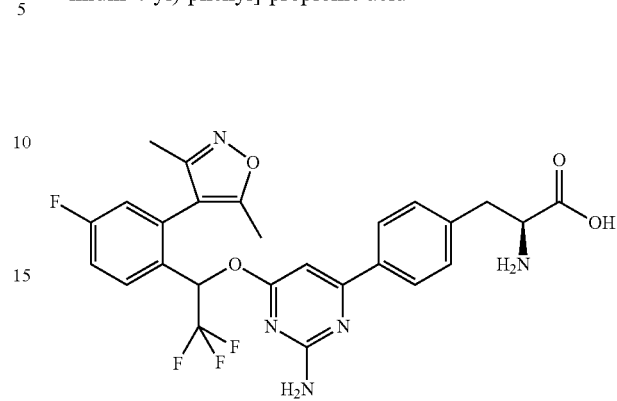

(51)
(S)-2-amino-3-[4-(2-amino-6-{2,2,2-trifluoro-1-[5-fluoro-2-(3-methyl-pyrazol-1-yl)-phenyl]-ethoxy}-pyrimidin-4-yl)-phenyl]-propionic acid

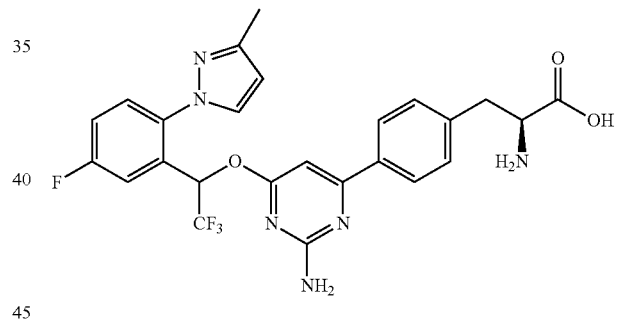

(52)
(S)-2-amino-3-[4-(2-amino-6{2,2,2-trifluoro-1-[5-chloro-2-(3-methyl-pyrazol-1-yl)-phenyl]-ethoxy}-pyrimidin-4-yl)-phenyl]-propionic acid

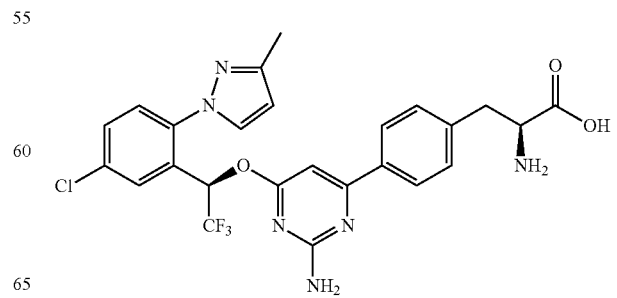

(53)
(S)-2-amino-3-[4-(2-amino-6-{2,2,2-trifluoro-1-[4-(2-oxo-pyrrolidin-1-yl)-phenyl]-ethoxy}-pyrimidin-4-yl)-phenyl]-propionic acid

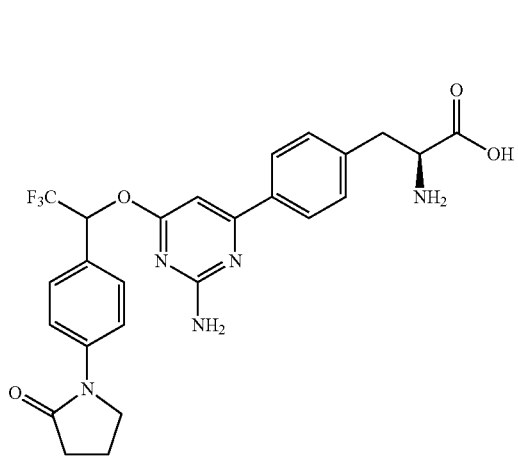 [SMILES: Nc1nc(OC(c2ccc(N3CCCC3=O)cc2)C(F)(F)F)cc(-c2ccc(C[C@H](N)C(=O)O)cc2)n1]

(54)
(S)-2-Amino-3-[4-(2-amino-6-{(R)-2,2,2-trifluoro-1-[5-fluoro-2-(3-methyl-pyrazol-1-yl)-phenyl]-ethoxy}-pyrimidin-4-yl)-phenyl]-propionic acid

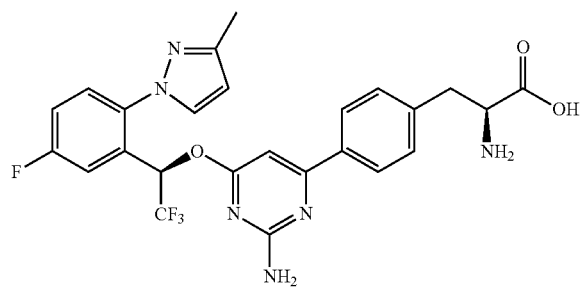 [SMILES: Cc1ccn(-c2ccc(F)cc2[C@@H](Oc2cc(-c3ccc(C[C@H](N)C(=O)O)cc3)nc(N)n2)C(F)(F)F)n1]

(55)
(S)-2-Amino-3-[4-(2-amino-6-{2,2,2-trifluoro-1-[4-(6-methoxy-pyridin-2-yl)-phenyl]-ethoxy}-pyrimidin-4-yl)-phenyl]-propionic acid

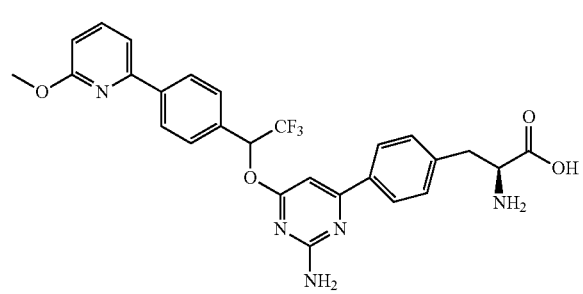 [SMILES: COc1cccc(-c2ccc(C(Oc3cc(-c4ccc(C[C@H](N)C(=O)O)cc4)nc(N)n3)C(F)(F)F)cc2)n1]

(56)
(S)-2-Amino-3-[4-(2-amino-6-{2,2,2-trifluoro-1-[2-fluoro-4-(5-methoxy-pyridin-3-yl)-phenyl]-ethoxy}-pyrimidin-4-yl)-phenyl]-propionic acid

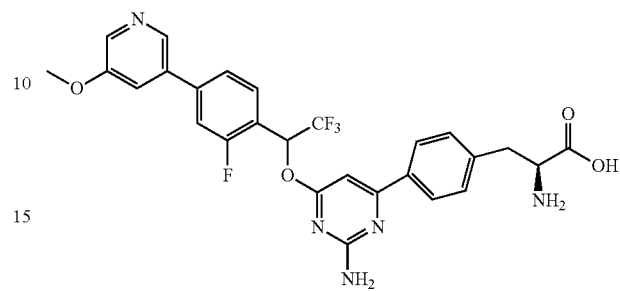

(57)
(S)-2-Amino-3-[4-(2-amino-6-{(S)-2,2,2-trifluoro-1-[4-(2-fluoro-pyridin-4-yl)-phenyl]-ethoxy}-pyrimidin-4-yl)-phenyl]-propionic acid

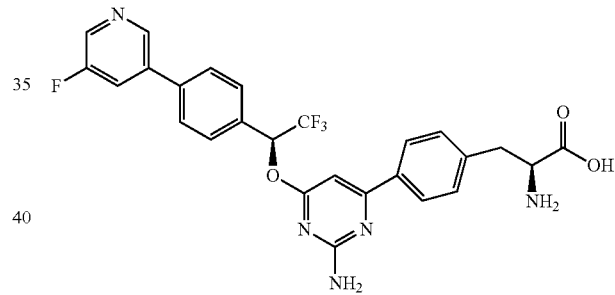

(58)
(S)-2-Amino-3-[4-(2-amino-6-{(S)-2,2,2-trifluoro-1-[4-(5-methoxy-pyridin-3-yl)-phenyl]-ethoxy}-pyrimidin-4-yl)-phenyl]-propionic acid

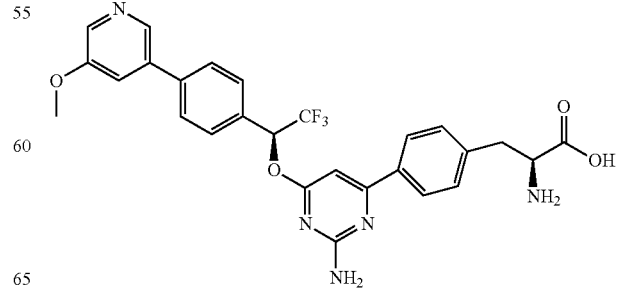

(59)
(S)-2-Amino-3-[4-(2-amino-6-{(S)-2,2,2-trifluoro-1-[4-(4-trifluoromethyl-pyridin-3-yl)-phenyl]-ethoxy}-pyrimidin-4-yl)-phenyl]-propionic acid

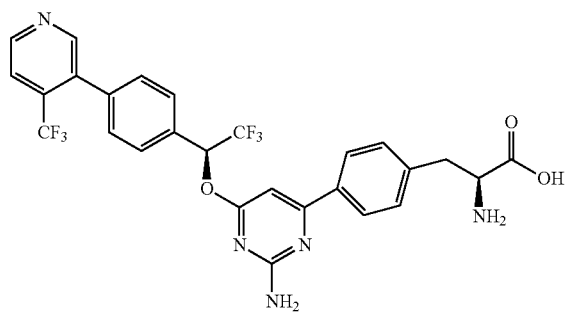 [SMILES: Nc1nc(O[C@@H](c2ccc(-c3cnccc3C(F)(F)F)cc2)C(F)(F)F)cc(-c2ccc(C[C@H](N)C(=O)O)cc2)n1]

(60)
(S)-2-Amino-3-(4-{2-amino-6-[(S)-2,2,2-trifluoro-1-(4-isoxazol-4-yl-phenyl-1)-ethoxy]-pyrimidin-4-yl}-phenyl)-propionic acid

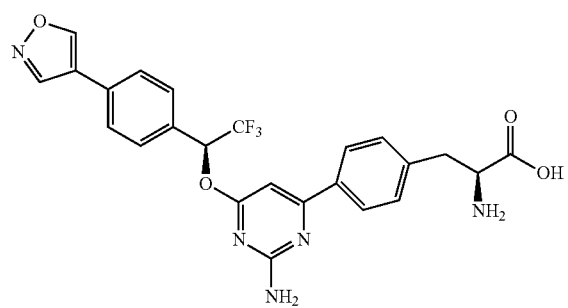 [SMILES: Nc1nc(O[C@@H](c2ccc(-c3cnoc3)cc2)C(F)(F)F)cc(-c2ccc(C[C@H](N)C(=O)O)cc2)n1]

(61)
(S)-2-Amino-3-(4-{2-amino-6-[2,2,2-trifluoro-1-(2-pyrimidin-5-yl-phenyl)-ethoxy]-pyrimidin-4-yl}-phenyl)-propionic acid

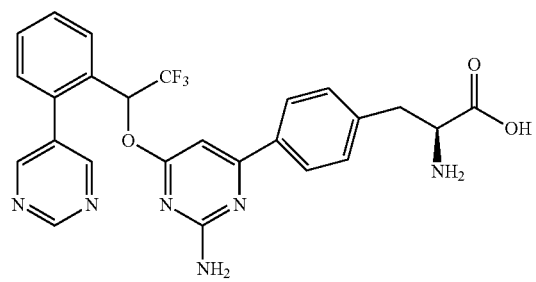 [SMILES: Nc1nc(OC(c2ccccc2-c2cncnc2)C(F)(F)F)cc(-c2ccc(C[C@H](N)C(=O)O)cc2)n1]

(62)
(S)-2-amino-3-(4-{2-amino-6-[2,2,2-trifluoro-1-(2-thiophen-3-yl-phenyl)-ethoxy]-pyrimidin-4-yl}-phenyl)-propionic acid

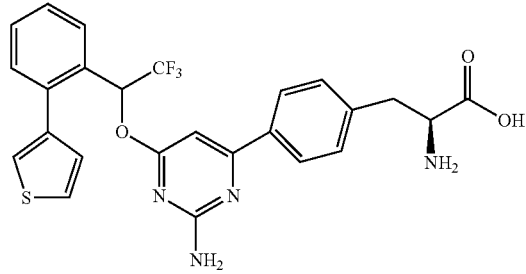 [SMILES: Nc1nc(OC(c2ccccc2-c2ccsc2)C(F)(F)F)cc(-c2ccc(C[C@H](N)C(=O)O)cc2)n1]

(63)
(S)-2-Amino-3-[4-(2-amino-6-{2,2,2-trifluoro-1-[2-(1-methyl-1H-pyrazol-4-yl)-phenyl]-ethoxy}-pyrimidin-4-yl)-phenyl]-propionic acid

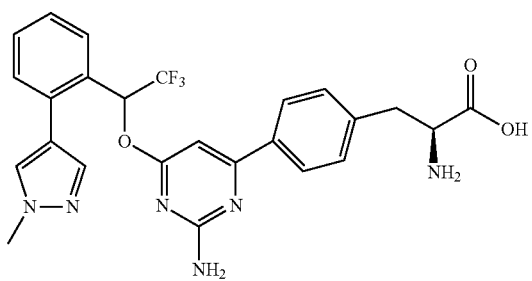 [SMILES: Cn1cc(-c2ccccc2C(Oc2cc(-c3ccc(C[C@H](N)C(=O)O)cc3)nc(N)n2)C(F)(F)F)cn1]

(64)
(S)-2-amino-3-(4-{6-[2,2,2-trifluoro-1-(2-furan-3-yl-phenyl)-ethoxy]-pyrimidin-4-yl}-phenyl)-propionic acid

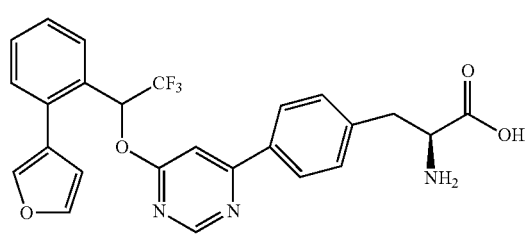 [SMILES: N[C@@H](Cc1ccc(-c2cc(OC(c3ccccc3-c3ccoc3)C(F)(F)F)ncn2)cc1)C(=O)O]

(65)
(S)-2-amino-3-(4-{6-[2,2,2-trifluoro-1-(2-furan-2-yl-phenyl)-ethoxy]-pyrimidin-4-yl}-phenyl)-propionic acid

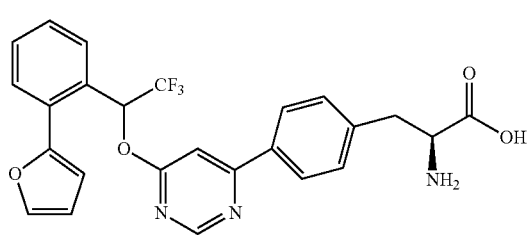 [SMILES: N[C@@H](Cc1ccc(-c2cc(OC(c3ccccc3-c3ccco3)C(F)(F)F)ncn2)cc1)C(=O)O]

(66) (2S)-2-amino-3-(4-(2-amino-6-(2,2,2-trifluoro-1-(4-(pyridin-3-yl)phenyl)ethoxy)pyrimidin-4-yl)phenyl)propanoic acid

(67) (2S)-2-amino-3-(4-(2-amino-6-(2,2,2-trifluoro-1-(2-(2-methylpyridin-4-yl)phenyl)ethoxy)pyrimidin-4-yl)phenyl) propanoic acid

(68) (2S)-2-amino-3-(4-(2-amino-6-(2,2,2-trifluoro-1-(2-(4-methylthiophen-3-yl)phenyl)ethoxy)pyrimidin-4-yl)phenyl) propanoic acid

(69) (2S)-3-(4-(6-(1-(2-(1H-pyrazol-1-yl)phenyl)-2,2,2-trifluoroethoxy)-2-aminopyrimidin-4-yl)phenyl)-2-aminopropanoic acid

(70) (2S)-2-amino-3-(4-(2-amino-6-(2,2,2-trifluoro-1-(4-(furan-2-yl)phenyl)ethoxy)pyrimidin-4-yl)phenyl)propanoic acid

(71) (2S)-2-amino-3-(4-(6-(2,2,2-trifluoro-1-(2-(pyridin-3-yloxy)phenyl)ethoxy)pyrimidin-4-yl)phenyl)propanoic acid

(72) (2S)-3-(4-(6-(1-(2-(1H-1,2,4-triazol-1-yl)phenyl)-2,2,2-trifluoroethoxy)-2-aminopyrimidin-4-yl)phenyl)-2-aminopropanoic acid

(73) (2S)-2-amino-3-(4-(2-amino-6-(2,2,2-trifluoro-1-(2-(furan-3-yl)phenyl)ethoxy)pyrimidin-4-yl)phenyl)propanoic acid

(74) (2S)-2-amino-3-(4-(2-amino-6-(2,2,2-trifluoro-1-(4-(furan-2-yl)-3-methoxyphenyl)ethoxy)pyrimidin-4-yl)phenyl) propanoic acid

(75) (2S)-2-amino-3-(4-(5-(2,2,2-trifluoro-1-(2-(furan-2-yl)phenyl)ethoxy)pyrazin-2-yl)phenyl)propanoic acid

(76) (2S)-3-(4-(5-(1-(2-(1H-pyrazol-1-yl)phenyl)-2,2,2-trifluoroethoxy)pyrazin-2-yl)phenyl)-2-aminopropanoic acid

(77) (2S)-2-amino-3-(4-(2-amino-6-(1-(4,5-dimethoxy-2-(1H-pyrazol-1-yl)phenyl)-2,2,2-trifluoroethoxy)pyrimidin-4-yl)phenyl)propanoic acid

(78) (2S)-2-amino-3-(4-(2-amino-6-(2,2,2-trifluoro-1-(2-(2-methyl-1H-imidazol-1-yl)phenyl)ethoxy)pyrimidin-4-yl) phenyl)propanoic acid

(79) (2S)-2-amino-3-(4-(2-amino-6-(2,2,2-trifluoro-1-(2-(5-methylthiophen-2-yl)phenyl)ethoxy)pyrimidin-4-yl)phenyl) propanoic acid

(80) (2S)-2-amino-3-(4-(2-amino-6-(1-(2-(5-(dimethylcarbamoyl)furan-2-yl)phenyl)-2,2,2-trifluoroethoxy)pyrimidin-4-yl)phenyl)propanoic acid

(81) (2S)-2-amino-3-(4-(2-amino-6-(2,2,2-trifluoro-1-(4-fluoro-2-(thiophen-2-yl)phenyl)ethoxy)pyrimidin-4-yl)phenyl) propanoic acid

(82) (2S)-2-amino-3-(4-(6-(2,2,2-trifluoro-1-(4-fluoro-2-(thiophen-3-yl)phenyl)ethoxy)pyrimidin-4-yl)phenyl) propanoic acid

(83) (2S)-2-amino-3-(4-(6-(2,2,2-trifluoro-1-(4-fluoro-2-(thiophen-3-yl)phenyl)ethoxy)pyrimidin-4-yl)phenyl) propanoic acid

(84) (2S)-2-amino-3-(4-(6-(2,2,2-trifluoro-1-(4-fluoro-2-(4-methylthiophen-2-yl)phenyl)ethoxy)pyrimidin-4-yl)phenyl) propanoic acid

(85) (S)-2-amino-3-(4-(2-amino-6-((R)-2,2,2-trifluoro-1-(4-(6-fluoropyridin-3-yl)phenyl)ethoxy)pyrimidin-4-yl)phenyl) propanoic acid

(86) (2S)-3-(4-(6-(1-(4-(1H-imidazol-1-yl)phenyl)-2,2,2-trifluoroethoxy)-2-aminopyrimidin-4-yl)phenyl)-2-aminopropanoic acid

(87) (2S)-2-amino-3-(4-(6-(2,2,2-trifluoro-1-(4-(thiophen-2-yl) phenyl)ethoxy)pyrimidin-4-yl)phenyl)propanoic acid

(88) (S)-2-amino-3-(4-(2-amino-6-((R)-2,2,2-trifluoro-1(4-(pyrimidin-5-yl)phenyl)ethoxy)pyrimidin-4-yl)phenyl)propanoic acid

(89) (2S)-2-amino-3-(4-(6-(1-(2-(3,5-dimethylisoxazol-4-yl)-4-fluorophenyl)-2,2,2-trifluoroethoxy)pyrimidin-4-yl)phenyl)propanoic acid

(90) (S)-2-amino-3-(4-(2-amino-6-((R)-2,2,2-trifluoro-1-(4-(2-methylpyridin-4-yl)phenyl)ethoxy)pyrimidin-4-yl)phenyl)propanoic acid

(91) (2S)-3-(4-(6-(1-(4-(1H-1,2,4-triazol-1-yl)phenyl)-2,2,2-trifluoroethoxy)pyrimidin-4-yl)phenyl)-2-aminopropanoic acid

(92) (2S)-2-amino-3-(4-(2-amino-6-(2,2,2-trifluoro-1-(4-(piperidin-1-ylmethyl)phenyl)ethoxy)pyrimidin-4-yl)phenyl) propanoic acid

(93) (2S)-2-amino-3-(4-(2-amino-6-(2,2,2-trifluoro-1-(2-fluoro-4-(2-methylpyridin-4-yl)phenyl)ethoxy)pyrimidin-4-yl) phenyl)propanoic acid

(94) (2S)-2-amino-3-(4-(2-amino-6-(1-(4-(6-chloropyridazin-3-yl)phenyl)-2,2,2-trifluoroethoxy)pyrimidin-4-yl)phenyl) propanoic acid

(95) (2S)-2-amino-3-(4-(2-amino-6-(1-(4-(4-tert-butylthiazol-2-yl)phenyl)-2,2,2-trifluoroethoxy)pyrimidin-4-yl)phenyl) propanoic acid

(96) (2S)-2-amino-3-(4-(2-amino-6-(2,2,2-trifluoro-1-(3'-methoxy-3-(3-methyl-1H-pyrazol-1-yl)biphenyl-4-yl)ethoxy) pyrimidin-4-yl)phenyl)propanoic acid

(97) (2S)-2-amino-3-(4-(2-amino-6-(1-(5-chloro-2-(3-methyl-1H-pyrazol-1-yl)phenyl)-2,2,2-trifluoroethoxy)pyrimidin-4-yl)phenyl)propanoic acid

(98) (S)-2-amino-3-(4-(2-amino-6-((R)-2,2,2-trifluoro-1-(3'-methoxybiphenyl-4-yl)ethoxy)pyrimidin-4-yl)phenyl) propanoate tosylate.

(99) (S)-2-amino-3-(4-(2-amino-6-((R)-2,2,2-trifluoro-1-(3'-methoxybiphenyl-4-yl)ethoxy)pyrimidin-4-yl)phenyl) propanoate maleate (100)
(S)-ethyl 2-amino-3-(4-(2-amino-6-((R)-1-(4-chloro-2-(3-methyl-1-H-pyrazol-1-yl)phenyl)-2,2,2-trifluoroethoxy)pyrimidin-4-yl)phenyl)propanoate hippurate (101)
(S)-ethyl 2-amino-3-(4-(2-amino-6-((R)-1-(4-chloro-2-(3-methyl-1-H-pyrazol-1-yl)phenyl)-2,2,2-trifluoroethoxy)pyrimidin-4-yl)phenyl)propanoate succinate (102)
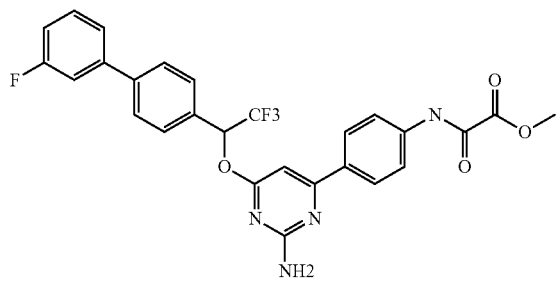 [SMILES: COC(=O)C(=O)Nc1ccc(-c2cc(OC(c3ccc(-c4cccc(F)c4)cc3)C(F)(F)F)nc(N)n2)cc1]

(103)
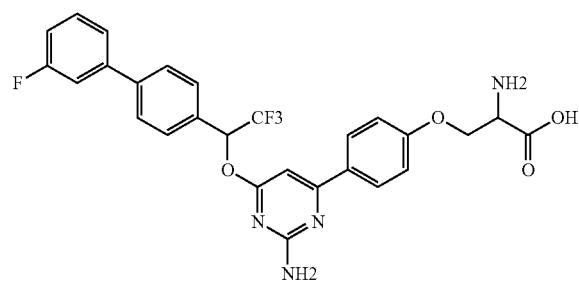 [SMILES: Nc1nc(OC(c2ccc(-c3cccc(F)c3)cc2)C(F)(F)F)cc(-c2ccc(OCC(N)C(=O)O)cc2)n1]

(104)
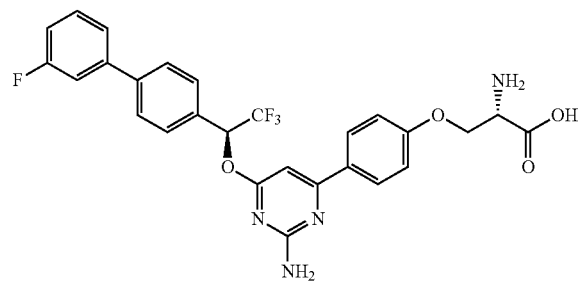 [SMILES: Nc1nc(O[C@@H](c2ccc(-c3cccc(F)c3)cc2)C(F)(F)F)cc(-c2ccc(OC[C@H](N)C(=O)O)cc2)n1]

(105)
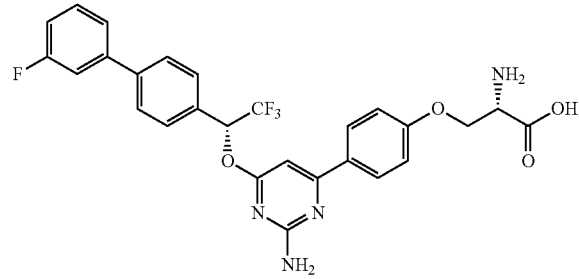

(106)
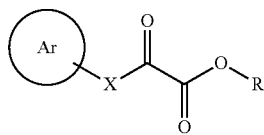

where Ar is a structure comprising multiple aryl or heterocycle rings;
X is —CH$_2$— or N; and
R is hydrogen or optionally substituted alkyl, alkyl-aryl, alkyl-heterocycle, aryl, or heterocycle.
In some compounds, X is N.
In some compounds, R is methyl, ethyl, or isopropyl.
In some compounds, X is N and R is methyl.
In some compounds, Ar is a structure comprising 1-4 optionally substituted linked cycloalkyl, aryl, or heterocycle rings. In some compounds, Ar comprises 1 ring; in some compounds, Ar comprises 2 rings; in some compounds, Ar comprises 3 rings; in some compounds, Ar comprises 4 rings.

(107)
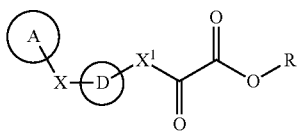

where A is optionally substituted cycloalkyl, aryl, or heterocycle; X is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; R is hydrogen or optionally substituted alkyl, alkyl-aryl, alkyl-heterocycle, aryl, or heterocycle; R$_3$ is hydrogen, alkoxy, amino, cyano, halogen, hydroxyl, or optionally substituted alkyl; R$_4$ is hydrogen, alkoxy, amino, cyano, halogen, hydroxyl, or optionally substituted alkyl or aryl; each R$_5$ is independently hydrogen or optionally substituted alkyl or aryl; and X$^1$ is —CH$_2$— or N.
In some compounds, X$^1$ is N.
In some compounds, R is methyl, ethyl, or isopropyl.
In some compounds, X$^1$ is N and R is methyl.
In some compounds, X$^1$ is N, R is methyl, X is —C(R$_3$R$_4$)O—, R$_3$ is hydrogen, and R$_4$ is substituted alkyl.

(108)
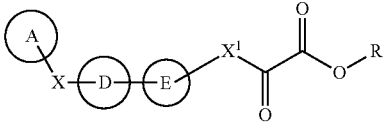

where A is optionally substituted cycloalkyl, aryl, or heterocycle; X is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; E is optionally substituted aryl or heterocycle; R is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and $X^1$ is —CH$_2$— or N.

In some compounds, $X^1$ is N.

In some compounds, R is methyl, ethyl, or isopropyl.

In some compounds, $X^1$ is N and R is methyl.

In some compounds, A is fluoro-substituted biphenyl, X is N, R is methyl, X is —C(R$_3$R$_4$)O—, $R_3$ is hydrogen, and $R_4$ is substituted alkyl. In some of these compounds, A is 3'-fluorobiphenyl. In some of these compounds, $R_4$ is halo-substituted methyl. In some of these compounds, D is substituted pyrimidinyl and E is phenyl. In some of these compounds, D is 2-substituted pyrimidinyl.

In some compounds, A is optionally substituted biphenyl, X is —C(R$_3$R$_4$)O—, $R_3$ is hydrogen, $R_4$ is optionally substituted lower alkyl, D is optionally substituted pyrimidinyl, E is phenyl, $X^1$ is N, and R is lower alkyl. In some of these compounds, A is 2'-, 3'-, 4'-, 5', or 6'-halo-substituted biphenyl, X is —C(R$_3$R$_4$)O—, $R_3$ is hydrogen, $R_4$ is halo-substituted methyl or ethyl, D is 2-substituted pyrimidinyl, E is phenyl, $X^1$ is N, and R is methyl or ethyl. In some of these compounds, A is 2'-, 3'-, 4'-, 5', or 6'-fluoro-substituted biphenyl, X is —C(R$_3$R$_4$)O—, $R_3$ is hydrogen, $R_4$ is fluoro-substituted methyl, D is 2-amino substituted pyrimidinyl, E is phenyl, $X^1$ is N, and R is methyl.

(109)

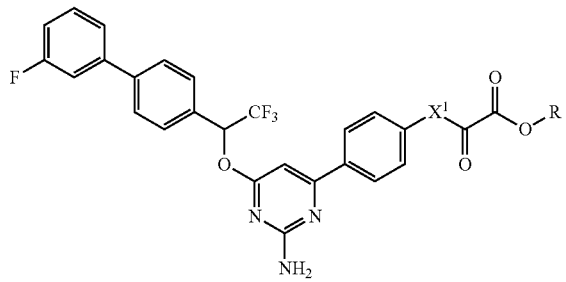

where: $X^1$ is —CH$_2$— or N; and
R is hydrogen or optionally substituted alkyl, alkyl-aryl, alkyl-heterocycle, aryl, or heterocycle.

In some compounds, $X^1$ is N.

In some compounds, R is methyl, ethyl, or isopropyl.

(110)

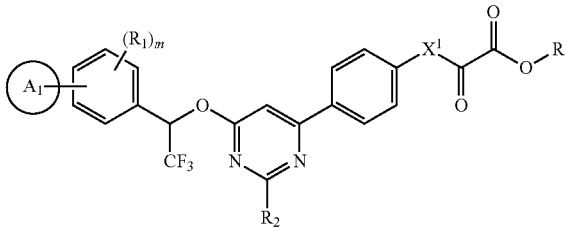

where $A_1$ is optionally substituted aryl or heterocycle; each $R_1$ is independently halogen, hydrogen, C(O)R$_A$, OR$_A$, NR$_B$R$_C$, S(O$_2$)R$_A$, or optionally substituted alkyl, alkyl-aryl or alkyl-heterocycle; $R_2$ is independently halogen, hydrogen, C(O)R$_A$, OR$_A$, NR$_B$R$_C$, S(O$_2$)R$_A$, or optionally substituted alkyl, alkyl-aryl or alkyl-heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; $X^1$ is —CH$_2$— or N; R is hydrogen or optionally substituted alkyl, alkyl-aryl, alkyl-heterocycle, aryl, or heterocycle; and m is 1-4.

(111)

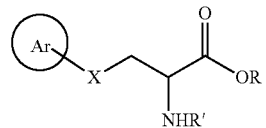

where:
Ar is a structure comprising multiple aryl or heterocycle rings;
X is N, O, or S;
R is hydrogen or optionally substituted alkyl, alkyl-aryl, alkyl-heterocycle, aryl, or heterocycle; and
R' is hydrogen or optionally substituted alkyl.

In some compounds, X is O.

In some compounds, X is O and R and R' are hydrogen.

In some compounds, Ar is a structure comprising 1-4 optionally substituted linked cycloalkyl, aryl, or heterocycle rings. In some compounds, Ar comprises 1 ring; in some compounds, Ar comprises 2 rings; in some compounds, Ar comprises 3 rings; in some compounds, Ar comprises 4 rings.

(112)

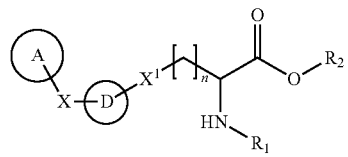

where A is optionally substituted cycloalkyl, aryl, or heterocycle; X is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; $R_1$ is hydrogen or alkyl; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; n is 0-3; and $X^1$ is N, O, or S. In certain embodiments, the carbon having the HNR$^1$ group is in the S configuration.

In some compounds, $X^1$ is O and n is 1.

In some compounds, $X^1$ is O, n is 1, $R_1$ is hydrogen, and $R_2$ is hydrogen.

In some compounds, $X^1$ is O, n is 1, $R_1$ is hydrogen, $R_2$ is hydrogen, X is —C(R$_3$R$_4$)O—, $R_3$ is hydrogen, and $R_4$ is substituted alkyl.

(113)

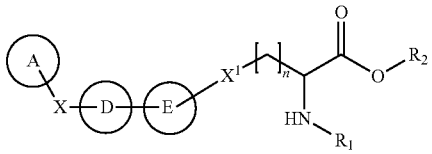

where A is optionally substituted cycloalkyl, aryl, or heterocycle; X is a bond (i.e., A is directly bound to D), —O—, —S—, —C(O)—, —C(R$_4$)=, =C(R$_4$)—, —C(R$_3$R$_4$)—, —C(R$_4$)=C(R$_4$)—, —C≡C—, —N(R$_5$)—, —N(R$_5$)C(O)N(R$_5$)—, —C(R$_3$R$_4$)N(R$_5$)—, —N(R$_5$)C(R$_3$R$_4$)—, —ONC(R$_3$)—, —C(R$_3$)NO—, —C(R$_3$R$_4$)O—, —OC(R$_3$R$_4$)—, —S(O$_2$)—, —S(O$_2$)N(R$_5$)—, —N(R$_5$)S(O$_2$)—, —C(R$_3$R$_4$)S(O$_2$)—, or —S(O$_2$)C(R$_3$R$_4$)—; D is optionally substituted aryl or heterocycle; E is optionally substituted aryl or heterocycle; R$_1$ is H or alkyl; R$_2$ is hydrogen or optionally substituted alkyl, alkyl-aryl, alkyl-heterocycle, aryl, or heterocycle; R$_3$ is hydrogen, alkoxy, amino, cyano, halogen, hydroxyl, or optionally substituted alkyl; R$_4$ is hydrogen, alkoxy, amino, cyano, halogen, hydroxyl, or optionally substituted alkyl or aryl; each R$_5$ is independently hydrogen or optionally substituted alkyl or aryl; n is 0-3; and X$^1$ is N, O, or S.

In some compounds, X$^1$ is O.

In some compounds, X$^1$ is O, n is 1, R$_1$ is hydrogen, and R$_2$ is hydrogen.

In some compounds, X$^1$ is O, n is 1, R$_1$ is hydrogen, R$_2$ is hydrogen, X is —C(R$_3$R$_4$)O—, R$_3$ is hydrogen, and R$_4$ is substituted alkyl. In some of these embodiments, A is fluoro-substituted biphenyl and R$_3$ is hydrogen. In some of these embodiments, A is 3'-fluorobiphenyl. In some of these embodiments, R$_4$ is halo-substituted methyl. In some of these embodiments, D is substituted pyrimidinyl and E is phenyl. In some of these embodiments, D is 2-substituted pyrimidinyl.

In some compounds, A is optionally substituted biphenyl, X is —C(R$_3$R$_4$)O—, R$_3$ is hydrogen, R$_4$ is optionally substituted lower alkyl, D is optionally substituted pyrimidinyl, E is phenyl, X$^1$ is O, n is 1, R$_1$ is hydrogen or lower alkyl, and R$_2$ is hydrogen or lower alkyl. In some of these compounds, A is 2'-, 3'-, 4'-, 5', or 6'-halo-substituted biphenyl, X is —C(R$_3$R$_4$)O—, R$_3$ is hydrogen, R$_4$ is halo-substituted methyl or ethyl, D is 2-substituted pyrimidinyl, E is phenyl, X$^1$ is O, n is 1, R$_1$ is hydrogen, and R$_2$ is hydrogen. In some of these compounds, A is 2'-, 3'-, 4'-, 5', or 6'-fluoro-substituted biphenyl, X is —C(R$_3$R$_4$)O—, R$_3$ is hydrogen, R$_4$ is fluoro-substituted methyl, D is 2-amino substituted pyrimidinyl, E is phenyl, X$^1$ is O, n is 1, R$_1$ is hydrogen, and R$_2$ is hydrogen.

(114)

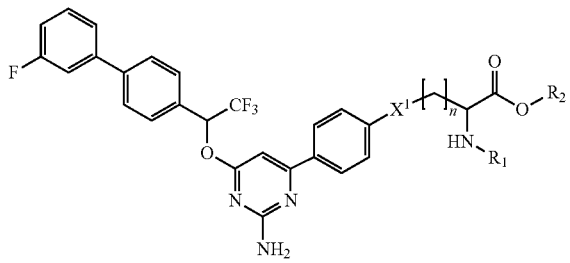

where:
X$^1$ is N, O, or S;
R$_1$ is hydrogen or optionally substituted alkyl;
R$_2$ is hydrogen or optionally substituted alkyl, alkyl-aryl, alkyl-heterocycle, aryl, or heterocycle; and
n is 0-3.

In some compounds, X$^1$ is O and n is 1. In certain embodiments, the carbon having the HNR$^1$ group is in the S configuration.

(115)

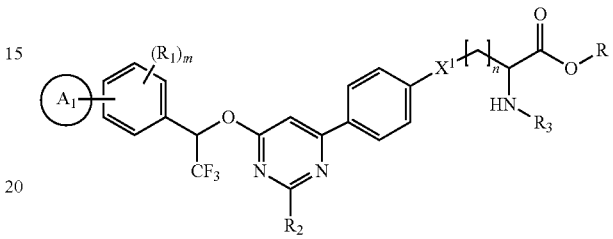

where A$_1$ is optionally substituted aryl or heterocycle; R is hydrogen or optionally substituted alkyl, alkyl-aryl, alkyl-heterocycle, aryl, or heterocycle; each R$_1$ is independently halogen, hydrogen, C(O)R$_A$, OR$_A$, NR$_B$R$_C$, S(O$_2$)R$_A$, or optionally substituted alkyl, alkyl-aryl or alkyl-heterocycle; R$_2$ is halogen, hydrogen, C(O)R$_A$, OR$_A$, NR$_B$R$_C$, S(O$_2$)R$_A$, or optionally substituted alkyl, alkyl-aryl or alkyl-heterocycle; R$_3$ is hydrogen or optionally substituted alkyl; each R$_A$ is independently hydrogen or optionally substituted alkyl, alkyl-aryl or alkyl-heterocycle; each R$_B$ is independently hydrogen or optionally substituted alkyl, alkyl-aryl or alkyl-heterocycle; each R$_C$ is independently hydrogen or optionally substituted alkyl, alkyl-aryl or alkyl-heterocycle; X$^1$ is N, O, or S; m is 1-4; and n is 0-3. In certain embodiments, the carbon having the HNR$_3$ group is in the S configuration.

In some compounds, X$^1$ is O and n is 1.

In some compounds, X$^1$ is O, n is 1, R$_1$ is hydrogen, and R$_2$ is hydrogen.

(116)

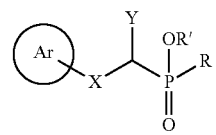

where:
Ar is a structure comprising multiple aryl or heterocycle rings;
X is —CH$_2$— or N;
Y is hydrogen or NH$_2$;
R is optionally substituted alkyl or alkoxy; and
R' is hydrogen or optionally substituted alkyl, alkyl-aryl, alkyl-heterocycle, aryl, or heterocycle.

In some compounds, X is N, Y is NH$_2$, R is optionally substituted alkyl, and R' is hydrogen.

In some compounds, Ar is a structure comprising 1-4 optionally substituted linked cycloalkyl, aryl, or heterocycle rings. In some compounds, Ar comprises 1 ring; in some compounds, Ar comprises 2 rings; in some compounds, Ar comprises 3 rings; in some compounds, Ar comprises 4 rings.

(117)

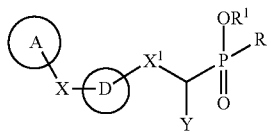

where A is optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; $X^1$ is —$CH_2$— or N; Y is hydrogen or $NH_2$; R is optionally substituted alkyl or alkoxy; and $R^1$ is hydrogen or optionally substituted alkyl, alkyl-aryl, alkyl-heterocycle, aryl, or heterocycle. In certain embodiments where Y is $NH_2$, the carbon to which Y is attached is in the S configuration. In other embodiments, the carbon to which Y is attached is in the R configuration.

In some compounds, $X^1$ is N, Y is $NH_2$, R is optionally substituted alkyl, and R' is hydrogen.

(118)

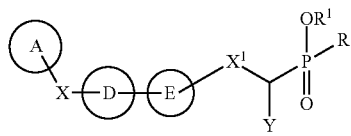

where A is optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; $X^1$ is —$CH_2$— or N; Y is hydrogen or $NH_2$; R is optionally substituted alkyl or alkoxy; and $R^1$ is hydrogen or optionally substituted alkyl, alkyl-aryl, alkyl-heterocycle, aryl, or heterocycle. In certain embodiments where Y is $NH_2$, the carbon to which Y is attached is in the S configuration. In other embodiments, the carbon to which Y is attached is in the R configuration.

In some compounds, $X^1$ is N, Y is $NH_2$, R is optionally substituted alkyl, and R' is hydrogen.

In some compounds, A is optionally substituted biphenyl, X is —C($R_3R_4$)O—, $R_3$ is hydrogen, $R_4$ is optionally substituted lower alkyl, D is optionally substituted pyrimidinyl, E is phenyl, $X^1$ is —$CH_2$— or N; Y is hydrogen or $NH_2$, R is optionally substituted alkyl, and $R^1$ is hydrogen or lower alkyl. In some of these compounds, A is 2'-, 3'-, 4'-, 5', or 6'-halo-substituted biphenyl, X is —C($R_3R_4$)O—, $R_3$ is hydrogen, $R_4$ is halo-substituted methyl or ethyl, D is 2-substituted pyrimidinyl, E is phenyl, $X^1$ is N; Y is hydrogen, R is optionally substituted lower alkyl, and $R^1$ is hydrogen. In some of these compounds, A is 2'-, 3'-, 4'-, 5', or 6'-fluoro-substituted biphenyl, X is —C($R_3R_4$)O—, $R_3$ is hydrogen, $R_4$ is fluoro-substituted methyl, D is 2-amino substituted pyrimidinyl, E is phenyl, $X^1$ is N; Y is hydrogen, R is optionally substituted methyl or ethyl, and $R^1$ is hydrogen.

(119)

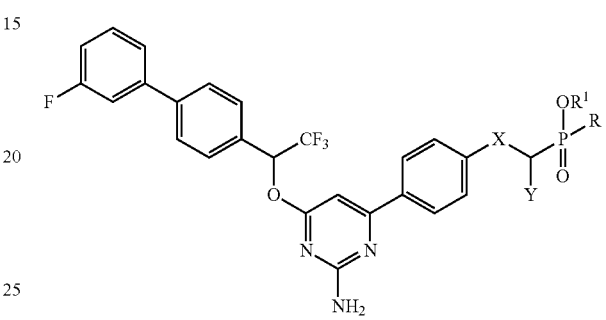

where:
X is —$CH_2$— or N;
Y is hydrogen or $NH_2$;
R is hydrogen or optionally substituted alkyl or alkoxy; and
R' is R is hydrogen or optionally substituted alkyl, alkyl-aryl, alkyl-heterocycle, aryl, or heterocycle. In certain embodiments where Y is $NH_2$, the carbon to which Y is attached is in the S configuration. In other embodiments, the carbon to which Y is attached is in the R configuration.

(120)

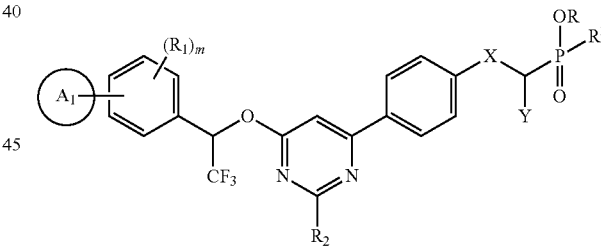

where $A_1$ is optionally substituted aryl or heterocycle; R is hydrogen or optionally substituted alkyl, alkyl-aryl, alkyl-heterocycle, aryl, or heterocycle; each $R_1$ is independently halogen, hydrogen, C(O)$R_A$, O$R_A$, $NR_BR_C$, S($O_2$)$R_A$, or optionally substituted alkyl, alkyl-aryl or alkyl-heterocycle; $R_2$ is halogen, hydrogen, C(O)$R_A$, O$R_A$, $NR_BR_C$, S($O_2$)$R_A$, or optionally substituted alkyl, alkyl-aryl or alkyl-heterocycle; $R_3$ is hydrogen or optionally substituted alkyl; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; X is —$CH_2$— or N; Y is hydrogen or $NH_2$; and m is 1-4. In certain embodiments where Y is $NH_2$, the carbon to which Y is attached is in the S configuration. In other embodiments, the carbon to which Y is attached is in the R configuration.

The present invention provides pharmaceutical compositions comprising a therapeutically effective amount of an agent that lowers serum or plasma serotonin such as the TPH1 inhibitors disclosed herein and at least one pharmaceutically acceptable excipient. In certain embodiments, the agent or TPH1 inhibitor may be in the form of a salt with a physiologically acceptable acid or base.

In certain embodiments, the patient's level of serum or plasma serotonin is measured prior to administering a therapeutic agent that lowers the level of serum or plasma serotonin. In other embodiments, the patient's level of serum or plasma serotonin is measured after administering the therapeutic agent that lowers the level of serum or plasma serotonin. In some embodiments, the patient's level of serum or plasma serotonin is measured before and after administering the therapeutic agent that lowers the level of serum or plasma serotonin.

In certain embodiments, the therapeutic agent that lowers the level of serum or plasma serotonin is repeatedly administered to the patient and the patient's level of serum or plasma serotonin is repeatedly measured until the patient's level of serum or plasma serotonin is reduced to a desired level, e.g., by at least about 10%, at least about 20%, at least about 30%, at least about 40%, at least about 50%, at least about 60%, at least about 70%, at least about 80%, or at least about 90%, compared to the level measured prior to the first administration of the therapeutic agent that lowers the level of serum or plasma serotonin.

In certain embodiments, the patient has been identified as having a serum or plasma serotonin level that is more than 10%, 25%, 35%, 50%, 75%, 100%, or 200% higher than the normal level of serum or plasma serotonin. Those of skill in the art will understand that serum or plasma serotonin levels may vary among individuals depending on certain factors and will be able to take those factors into account to determine whether a person has abnormally high serum or plasma serotonin levels. One possible range which those skilled in the art may consider to be normal serum or plasma serotonin levels is 101-283 ng/ml (nanograms per milliliter).

In certain embodiments, the patient's level of serum or plasma serotonin is lowered by at least about 10%, at least about 20%, at least about 30%, at least about 40%, at least about 50%, at least about 60%, at least about 70%, at least about 80%, or at least about 90% compared to the level before administering the therapeutic agent that lowers the level of serum or plasma serotonin.

In certain embodiments, the therapeutic agent that lowers the level of serum or plasma serotonin is administered in an amount of from about 1 mg/day to about 2 g/day.

The present invention also provides a method for identifying a patient having diabetes or at risk of developing diabetes and treating the patient, comprising:

a) determining the level of serum or plasma serotonin in a biological sample from the patient and in a biological sample from a normal subject;

b) administering to the patient a therapeutically effective amount of a therapeutic agent disclosed herein if the level of serum or plasma serotonin in the sample from the patient is elevated by at least about 25% above the serum or plasma serotonin level in the sample from the normal subject;

whereby the patient's serum or plasma serotonin level is lowered and diabetes is thereby treated.

In certain embodiments, "determining the level of serum or plasma serotonin" of step (a) includes the formation of a complex between the serum or plasma serotonin from the biological sample and a reagent that specifically binds to serotonin.

In certain embodiments, "determining the level of serum or plasma serotonin" of step (a) includes a process whereby the serum or plasma serotonin is transformed into a derivative of serotonin, e.g., N-acylserotonin.

In certain embodiments, the "administering to the patient a therapeutically effective amount of a therapeutic agent" of step b) results in the lowering of blood glucose levels in the patient.

The present invention provides a method of lowering blood glucose levels and thus treating or preventing diabetes in a patient known or suspected to be in need of such treatment or prevention comprising administering to the patient known or suspected to be in need of such treatment or prevention a therapeutically effective amount of an antagonist of the serotonin Htr2b receptor. In some embodiments, the antagonist of the serotonin Htr2b receptor is a compound having the formula

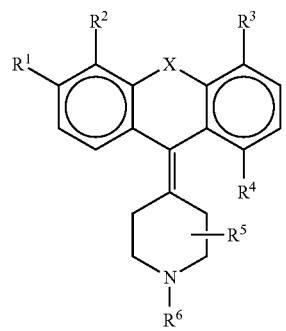

wherein $R^1$ is selected from the group consisting of ethyl, propyl, isopropyl, butyl, isobutyl, pentyl, hexyl, ethoxy, propoxy, isopropoxy, butoxy, isobutoxy, phenoxy, trifluoromethyl, trifluoromethoxy, amino, dimethylamino, —$CON(CH_3)_2$ and —$CON(C_2H_5)_2$;

$R^2$ is a methyl, ethyl, propyl, isopropyl, butyl, isobutyl, pentyl, hexyl, hydroxy or hydrogen, or $R^1$ and $R^2$ together form a five-membered heterocycle, wherein a heteroatom in said heterocycle is an oxygen atom;

$R^3$ is selected from the group consisting of methyl, ethyl, propyl, isopropyl, butyl isobutyl, pentyl, hexyl, hydroxy and hydrogen;

$R^4$ is selected from the group consisting of hydroxy, methoxy, ethoxy, propoxy, isopropoxy, butoxy, isobutoxy, trifluoromethyl, amino, dimethylamino, diethylamino, fluorine, chlorine, bromine, methyl, ethyl, propyl, isopropyl, butyl and hydrogen;

$R^5$ is methyl or hydrogen;

$R^6$ is methyl or ethyl; and

X is S, N or Se;

provided that when $R^1$ is ethoxy and X is S, at least one of $R^2$, $R^3$, W and $R^5$ is not hydrogen (see U.S. Pat. No. 7,060,711)

or is the compound SB224289 (Papageorgiou & Denef, 2007, Endocrinology 148:4509-4522).

BRIEF DESCRIPTION OF THE FIGURES

FIG. 2. GDS favors lipolysis through Htr2b receptor expressed in adipocytes. (A) Relative expression of indicated serotonin receptors in adipose tissue of fed and fasted mice. Plasma levels of (B) glycerol and (C) FFA in mice of indicated genotypes fasted for indicated time (n≥20). (D) Epididymal fat pad weight to body weight ratio in fed and fasted Htr2bf/f and Htr2bfatΔ/Δ mice (n≥12). (E) Average size of adipocytes from fat pad of fed and 48 h-fasted Htr2bf/f and Htr2bfatΔ/Δ mice (n≥5). (F) 48 h-fasting induced body weight loss of mice (n≥20). (G) Glycerol and (H) FFA release from Htr2bf/f or Htr2bfatΔ/Δ epididymal fat explants stimulated with 50 μM serotonin or 1 μM isoproterenol (n=5). (I) Western blot analysis of expression and activation of indicated proteins in Htr2bf/f and Htr2bfatΔ/Δ fat explants stimulated with 50 μM serotonin. * P<0.05, *** P<0.001. For each pair of bars in (B)-(F), the left bar represents Htr2bf/f and the right bar represents Htr2bfatΔ/Δ.

FIG. 7. (A) Metabolic parameters of Tph1f/f and Tph1gutΔ/Δ mice subjected to hyperinsulinemic-euglycemic clamp (n≥9). (B) Relative expression of indicated 5-HT receptors in primary mouse hepatocytes. (C) Normalized glycogen content in livers from fed and fasted Htr2bf/f and Htr2bliverΔ/Δ mice (n≥5). (D) β-hydroxybutyrate levels in Htr2bf/f and Htr2bliverΔ/Δ mice (n≥8). (E) Relative expression of indicated genes in liver from fed and fasted Htr2bf/f and Htr2bliverΔ/Δ mice (n≥5). * P<0.05.

FIG. 8. (A) Insulin tolerance test in Htr2bf/f and Htr2bfatΔ/Δ mice (n≥12). (B) Glucose tolerance test in Htr2bf/f and Htr2bliverΔ/Δ mice (n≥7). (C) Insulin levels during glucose tolerance test in Tph1f/f and Tph1gutΔ/Δ mice (n≥7). (D) Body weight gain of Tph1f/f and Tph1gutΔ/Δ mice fed normal or high fat diet (n≥5). (E) Pyruvate tolerance test in Tph1f/f and Tph1gutΔ/Δ mice fed normal or high fat diet (n≥5). (F) Plasma serotonin concentrations in mice treated with vehicle or LP533401 inhibitor (n≥8). (G) Body weight gain of mice treated with vehicle or LP533401 inhibitor, fed ND or HFD (n≥8). (H) Pyruvate tolerance test in mice treated with vehicle or LP533401 inhibitor (n≥8) fed ND or HFD. * P<0.05,  P<0.01,  P<0.001.

(aP2) mice implanted with serotonin-releasing pellets. (D) FFA levels in Htr2bf/f and Htr2bfatΔ/Δ (aP2) mice implanted with serotonin-releasing pellets.

FIG. 12. (A) Glycerol-evoked glucose production in Tph1f/f and Tph1gutΔ/Δ mice injected with serotonin (10 mg/kg BW) 90 min before the test (n≥7). (B) Glucose infusion rate during hyperinsulinemic-euglycemic clamp in Tph1f/f and Tph1gutΔ/Δ mice (n≥7). (C) Production of glucose from indicated substrates by primary hepatocytes stimulated with indicated doses of serotonin or 100 nM glucagon (n=5).

FIG. 13. (A) Glucose tolerance test in Tph1f/f and Tph1gutΔ/Δ mice injected with serotonin (10 mg/kg BW) 90 min before the test (n≥7). (B) Glucose uptake in primary hepatocytes stimulated with indicated doses of serotonin. (C) Production of glucose from indicated substrates by hepatocytes isolated from Htr2bf/f and Htr2bliverΔ/Δ mice and stimulated by 50 mM serotonin (n=5).

FIG. 14. (A) Glycerol tolerance test in Htr2bf/f and Htr2bliverΔ/Δ mice implanted with placebo or serotonin-releasing pellets (n≥6). (B) Normalized FBPase activity in isolated hepatocytes stimulated with indicated doses of serotonin (n≥3). Data are represented as mean±SEM, *p<0.05, p<0.01, *p<0.001. (C) Normalized G6Pase activity in isolated hepatocytes stimulated with indicated doses of serotonin (n≥3). Data are represented as mean±SEM, *p<0.05, p<0.01, *p<0.001. (D) Glucose tolerance test in Htr2bf/f and Htr2bliverΔ/Δ mice implanted with placebo or serotonin-releasing pellets (n≥6).

Figure 15B:
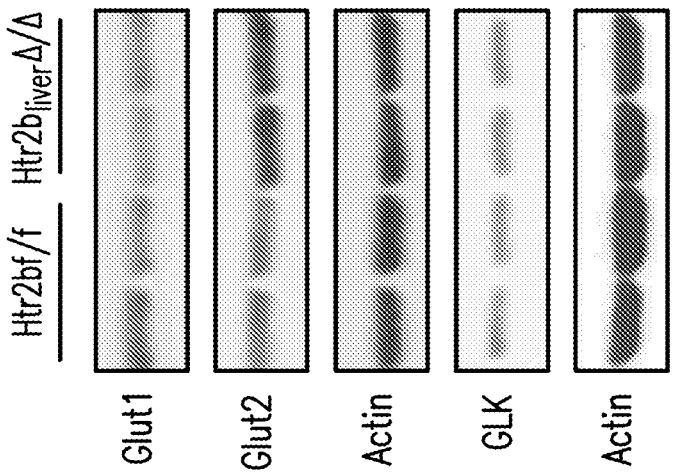
Figure 15A:
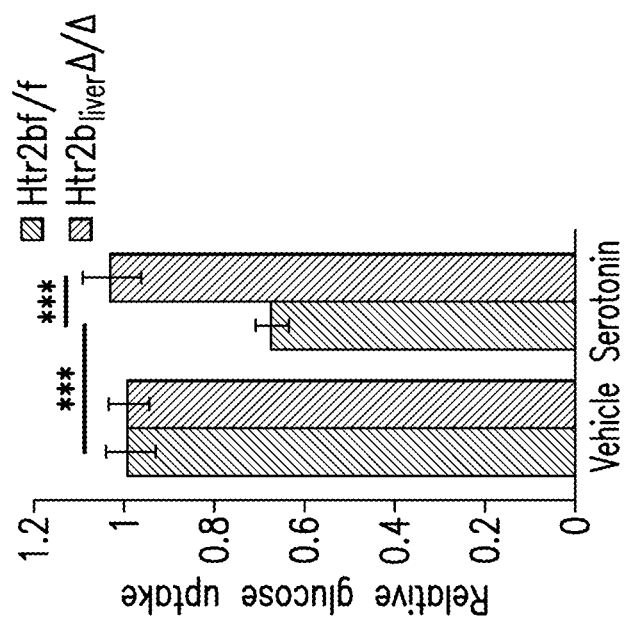
Figure 15C:
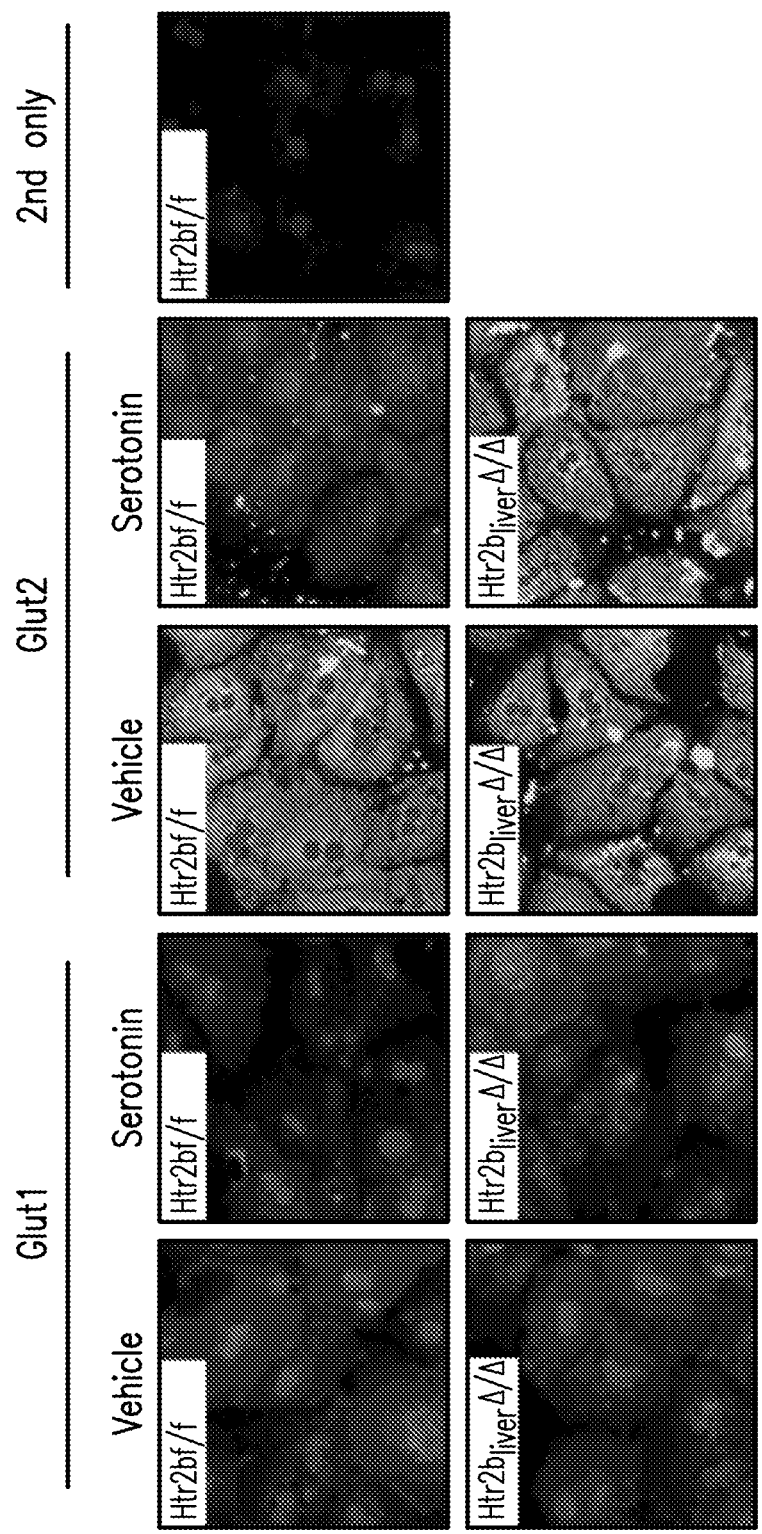

FIG. 15. (A) Relative glucose uptake in Htr2b-deficient hepatocytes stimulated with 50 mM serotonin. (B) Western blot analysis of expression of indicated proteins in livers from fasted Htr2bf/f and Htr2bliverΔ/Δ mice. (C) Immunofluorescence with antibodies against Glut1 and Glut2 on primary hepatocytes of indicated genotypes stimulated with 50 mM serotonin.

FIG. 16. (A) Normalized glucokinase activity in livers of fasted Htr2bf/f and Htr2bliverΔ/Δ mice. Data are represented as mean±SEM, *p<0.05, p<0.01, *p<0.001. (B) Same as for FIG. 8F except that data for mice treated with LP533401 and fed a normal diet (ND) are shown. (C) Same as for FIG. 8G except that data for mice treated with LP533401 and fed a normal diet (ND) are plotted.

Figure 17A:
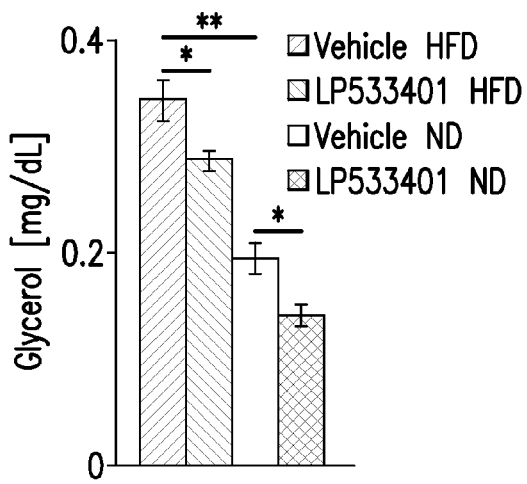
Figure 17B:
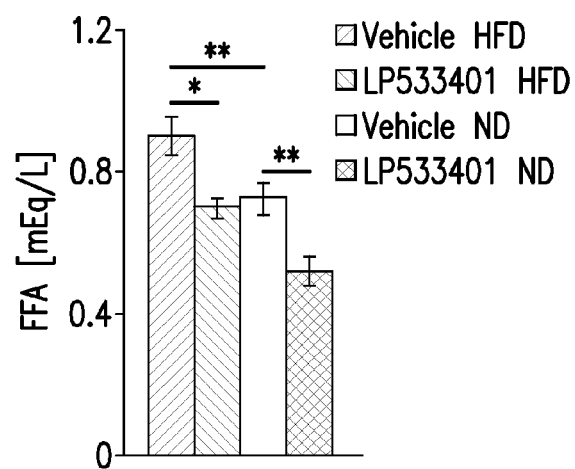
Figure 17C:
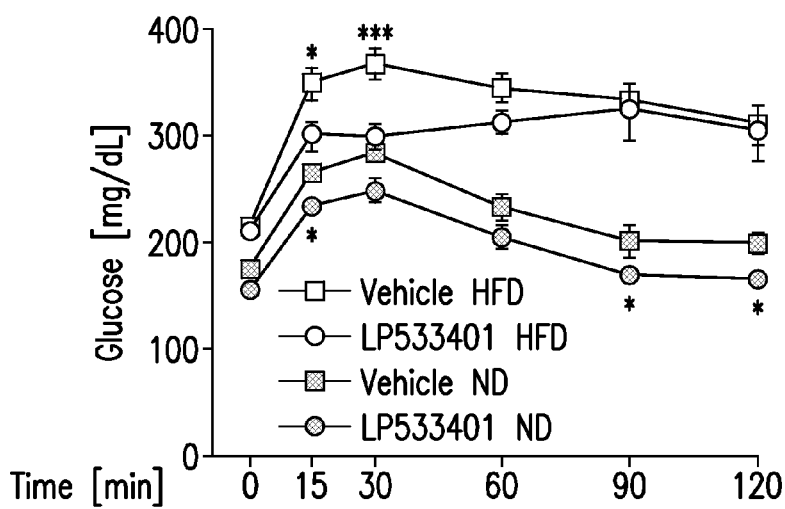

FIG. 17. (A) Same as for FIG. 4G except that data for mice treated with LP533401 and fed a normal diet (ND) are shown. (B) Same as for FIG. 4H except that data for mice treated with LP533401 and fed a normal diet (ND) are shown. (C) Same as for FIG. 8H except that data for mice treated with LP533401 and fed a normal diet (ND) are plotted.

Figure 18A:
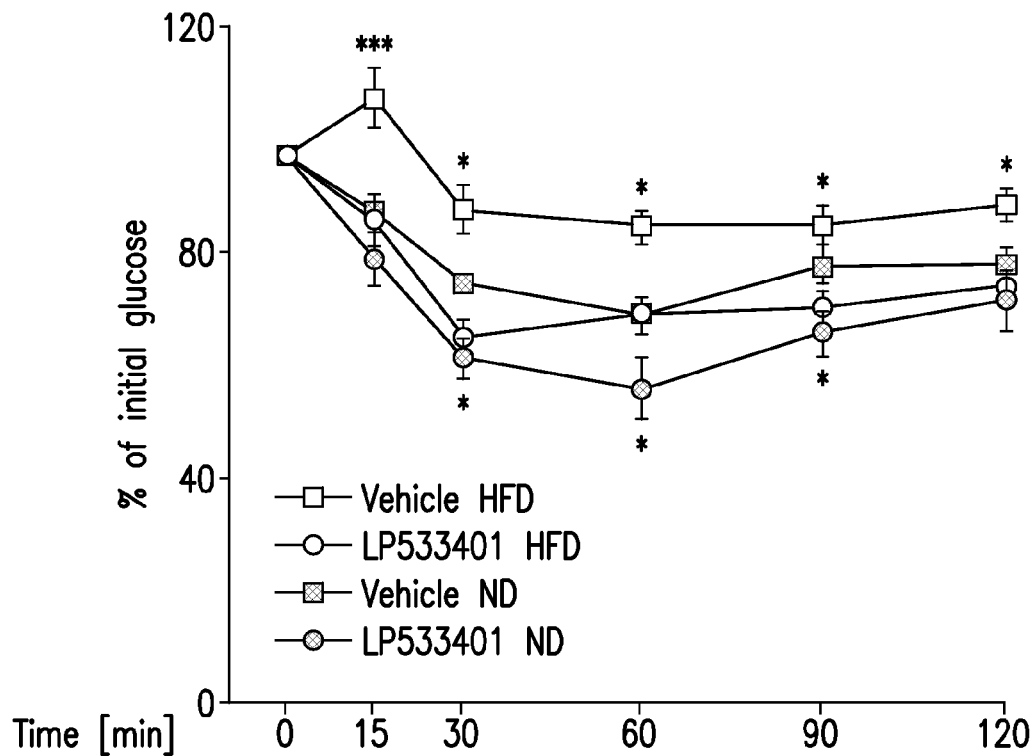
Figure 18B:
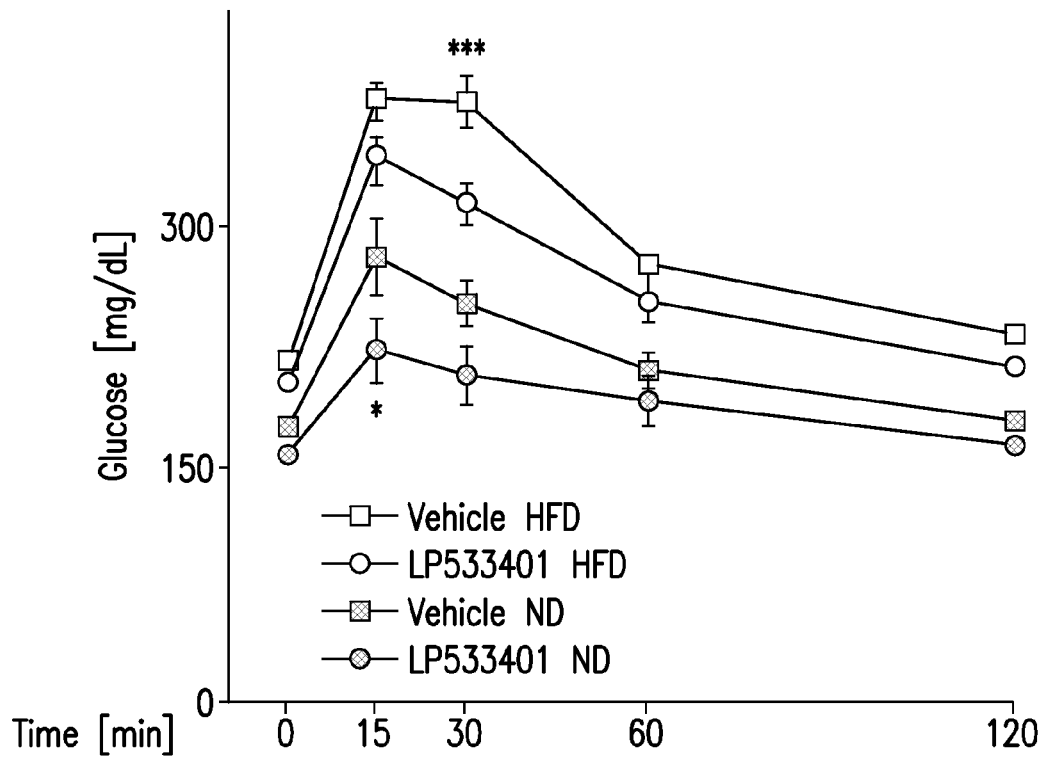

FIG. 18. (A) Same as for FIG. 4I except that data for mice treated with LP533401 and fed a normal diet (ND) are plotted. (B) Same as for FIG. 4J except that data for mice treated with LP533401 and fed a normal diet (ND) are plotted.

DETAILED DESCRIPTION OF THE INVENTION

The term "substituted," when used to describe a chemical structure or moiety, refers to a derivative of that structure or moiety wherein one or more of its hydrogen atoms is substituted with an atom, chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NH-CONH-alkyl-).

The term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

The term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

The term "alkoxy" means an —O-alkyl group. Examples of alkoxy groups include —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Term "alkylaryl" or "alkyl-aryl" means an alkyl moiety bound to an aryl moiety.

The term "alkylheteroaryl" or "alkyl-heteroaryl" means an alkyl moiety bound to a heteroaryl moiety.

The term "alkylheterocycle" or "alkyl-heterocycle" means an alkyl moiety bound to a heterocycle moiety.

The term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

The term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

The term "arylalkyl" or "aryl-alkyl" means an aryl moiety bound to an alkyl moiety.

The terms "halogen" and "halo" encompass fluorine, chlorine, bromine, and iodine.

The term "heteroalkyl" refers to an alkyl moiety (e.g., linear, branched or cyclic) in which at least one of its carbon atoms has been replaced with a heteroatom (e.g., N, O or S).

The term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

The term "heteroarylalkyl" or "heteroaryl-alkyl" means a heteroaryl moiety bound to an alkyl moiety.

The term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

The term "heterocycloalkyl" or "heterocycle-alkyl" refers to a heterocycle moiety bound to an alkyl moiety.

The term "heterocycloalkyl" refers to a non-aromatic heterocycle.

The term "heterocycloalkylalkyl" or "heterocycloalkyl-alkyl" refers to a heterocycloalkyl moiety bound to an alkyl moiety.

"Prevention of" or "preventing" diabetes means actively intervening as described herein prior to the overt onset of diabetes to prevent the development of diabetes or to minimize the extent of the diabetes or slow the course of development of the diabetes.

"Treatment of" or "treating" diabetes means actively intervening as described herein after the onset of diabetes to slow down, ameliorate symptoms of, minimize the extent of, or reverse the course of the diabetes in a patient who is known to have, is at risk of, or suspected to have, diabetes.

Unless otherwise indicated, a "therapeutically effective amount" of a therapeutic agent is an amount that provides a therapeutic benefit in the treatment or management of a disease or condition such as diabetes, delays or minimizes one or more symptoms associated with the disease or condition, or enhances the therapeutic efficacy of another therapeutic agent against the disease or condition. A therapeutic agent is said to be administered in a "therapeutically effective amount" if the amount administered results in a desired change in the physiology of a recipient mammal (e.g., decreasing blood glucose levels in a mammal having or at risk of developing diabetes) compared to pre-treatment levels. That is, the therapy results in treatment, i.e., modulates the recipient mammal's physiology to more closely resemble that of corresponding non-diseased state.

A "patient" is a mammal, preferably a human, but can also be a companion animal such as a dog or cat, or farm animals such as horses, cattle, pigs, or sheep.

In some embodiments, a patient "in need of prevention or treatment" for diabetes may include a patient known or suspected of having, or being at risk of developing, diabetes. Such a patient in need of treatment could be, e.g., a person known to have elevated blood glucose levels. Elevated blood glucose levels may include blood levels of greater than 100 mg/dl, when blood glucose levels are measured according to standard methods (e.g., under fasting conditions).

In some embodiments, a patient at risk of developing diabetes could include the elderly and the obese. Other persons in need of treatment or prevention by the methods of the present invention may include persons who are known to be in need of therapy to decrease serum or plasma serotonin levels in order to treat or prevent diabetes. In some embodiments, such persons might include persons who have been identified as having a serum or plasma serotonin level that is about 25% or more above that of serum or plasma serotonin levels in normal subjects.

In some embodiments, a patient at risk of developing diabetes could include a patient who has been diagnosed as having genetic factors that predispose the patient toward the development of diabetes.

In one embodiment, a patient in need of treatment or prevention for diabetes by the methods of the present invention does not include a patient being treated with a TPH1 inhibitor where the patient is being treated with the TPH1 inhibitor only for a purpose other than to treat diabetes. Thus, a patient in need of treatment or prevention for diabetes by the methods of the present invention does not include a patient being treated with a TPH1 inhibitor only for the purpose of treating chemotherapy-induced emesis, carcinoid syndrome, or gastrointestinal disorders such as irritable bowel syndrome.

A patient in need of treatment or prevention for diabetes by the methods of the present invention does not include a patient being treated with a TPH1 inhibitor only for the purpose of treating gastrointestinal diseases and certain other disorders. Examples of specific diseases and disorders include abdominal pain (e.g., associated with medullary carcinoma of the thyroid), anxiety, carcinoid syndrome, celiac disease, constipation (e.g., constipation having an iatrogenic cause, and idiopathic constipation), Crohn's disease, depression, diarrhea (e.g., bile acid diarrhea, enterotoxin-induced secretory diarrhea, diarrhea having an iatrogenic cause, idiopathic diarrhea (e.g., idiopathic secretory diarrhea), and traveler's diarrhea), emesis, functional abdominal pain, functional anorectal disorders, functional bloating, functional dyspepsia, functional gallbladder disorders, irritable bowel syndrome (IBS; including IBD-d, IBS-c and IBS-a), lactose intolerance, MEN types I and II, nausea, Ogilvie's syndrome, Pancreatic Cholera Syndrome, pancreatic insufficiency, pheochromacytoma, scleroderma, somatization disorder, sphincter of Oddi disorders, ulcerative colitis, and Zollinger-Ellison Syndrome. A patient in need of treatment or prevention for diabetes by the methods of the present invention does not include a patient being treated with a TPH1 inhibitor only for the purpose of treating these diseases and disorders.

A patient in need of treatment or prevention for diabetes by the methods of the present invention also does not include a patient being treated with a TPH1 inhibitor only for the purpose of treating the following diseases and disorders: acute and chronic hypertension, chronic obstructive pulmonary disease (COPD), pulmonary embolism (e.g., bronchoconstriction and pulmonary hypertension following pulmonary embolism), pulmonary hypertension (e.g., pulmonary hypertension associated with portal hypertension), and radiation pneumonitis (including that giving rise to or contributing to pulmonary hypertension). Others include abdominal migraine, adult respiratory distress syndrome (ARDS), carcinoid crisis, CREST syndrome (calcinosis, Raynaud's phenomenon, esophageal dysfunction, sclerodactyl), telangiectasia), serotonin syndrome, and subarachnoid hemorrhage.

A "TPH1 inhibitor" is a substance that reduces the amount of 5-hydroxytryptophan produced from tryptophan by TPH1 in a suitable assay, as compared to the amount of 5-hydroxytryptophan produced from tryptophan by TPH1 in the assay in the absence of the substance. Preferably, the reduction in the amount of 5-hydroxytryptophan produced is at least about 10%, at least about 15%, at least about 20%, at least about 40%, at least about 60%, at least about 80%, or at least about 90%. Examples of assays for determining the level of TPH1 inhibition by a substance are described in U.S. Patent Application Publication US 2009/0029993. In some embodiments, the TPH1 inhibitor is a substance that reduces the amount of 5-hydroxytryptophan produced from tryptophan by TPH1 by a mechanism that involves binding of the substance to TPH1.

"Gut derived serotonin (GDS)" refers to serotonin produced by TPH1 in the duodenum and is the major source for serotonin in the bloodstream, i.e., for plasma and serum serotonin.

An "antagonist of the serotonin Htr2b receptor," as used herein, refers to a substance which reduces the action or effect of signaling through the serotonin Htr2b receptor. Preferably, such reduction of the action or effect of the serotonin Htr2b receptor occurs by a mechanism that involves binding of the substance to the serotonin Htr2b receptor.

Methods of Treatment and Diagnosis

Adaptation to food deprivation is a regulated survival function that requires continuous mobilization of energy from various sources. The data described herein show that gut-derived serotonin (GDS) synthesis is enhanced by fasting and that this hormone promotes lipolysis by signaling in adipocytes through the Htr2b receptor to activate the lipolytic enzyme hormone sensitive lipase (HSL). Additionally, GDS promotes gluconeogenesis in the liver, also by signaling through Htr2b, to increase the activity of gluconeogenic enzymes fructose-1,6-bisphosphatase (FBPase) and glucose-6-phosphatase (G6Pase). Hence, GDS opposes deleterious consequences of food deprivation through two complementary mechanisms that can raise blood glucose levels. Thus, inhibition of GDS synthesis lowers blood glucose levels and improves insulin resistance and glucose intolerance caused by a high fat diet. Small molecule inhibitors of GDS synthesis such as TPH1 inhibitors therefore should be of use to treat Type II diabetes.

Figure 4A:
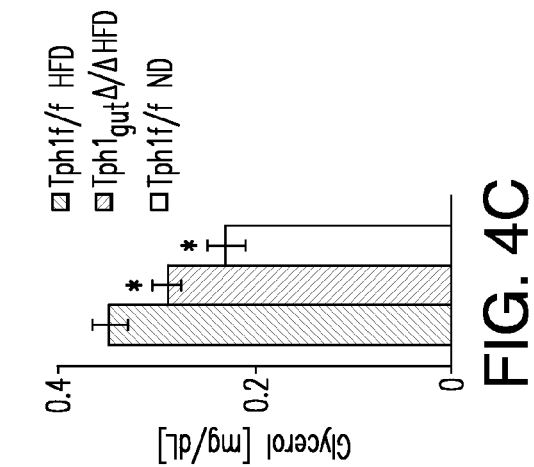
FIG. 4. Decreasing GDS synthesis protects from Type II diabetes. (A) Insulin and (B) glucose tolerance tests in Tph1f/f and Tph1gutΔ/Δ mice (n≥7). (C) Glycerol and (D) FFA plasma levels in mice of indicated genotypes fed normal (ND) or high fat diet (HFD), fasted for 4 h (n≥5). (E) Insulin and (F) glucose tolerance tests in Tph1f/f and Tph1gutΔ/Δ mice on indicated diet (n≥5). (G) Glycerol and (H) FFA plasma levels in mice treated with vehicle or LP533401 fed ND or HFD and fasted for 4 h (n≥7). (I) Insulin and (J) glucose tolerance tests in mice treated with vehicle or LP533401 fed ND or HFD (n≥7). (K) Model of GDS action. * P<0.05,  P<0.01, * P<0.001. For each triplet of bars in (C) and (D), the left bar represents Tph1f/f HFD (high fat diet), the middle bar represents Tph1gutΔ/Δ HFD, and the right bar represents Tph1f/f ND (normal diet). For each triplet of bars in (G) and (H), the left bar represents Vehicle HFD, the middle bar represents LP533401 HFD, and the right bar represents Vehicle ND.
Figure 4C:
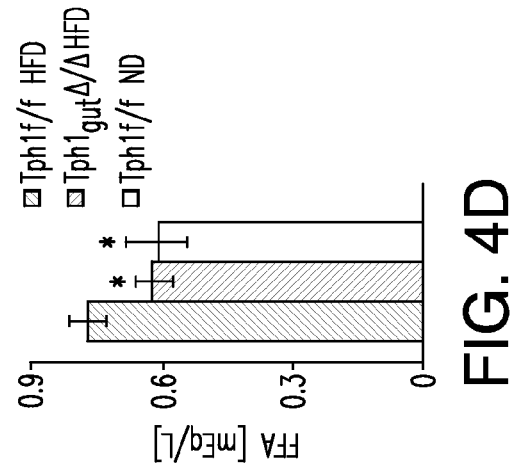
Figure 4B:
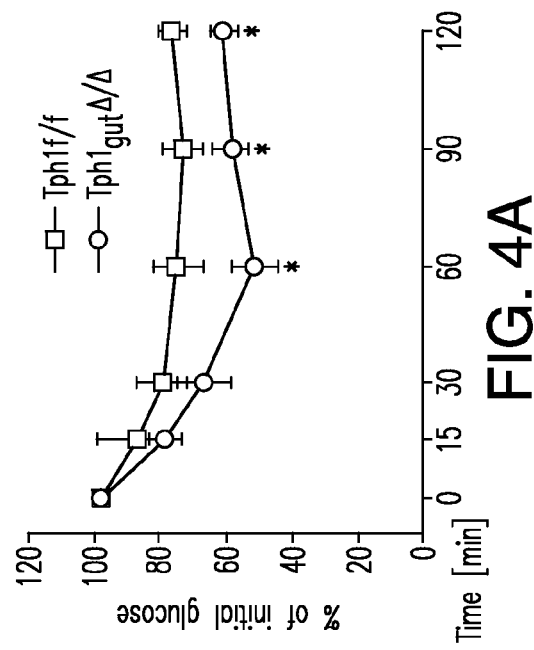
Figure 4D:
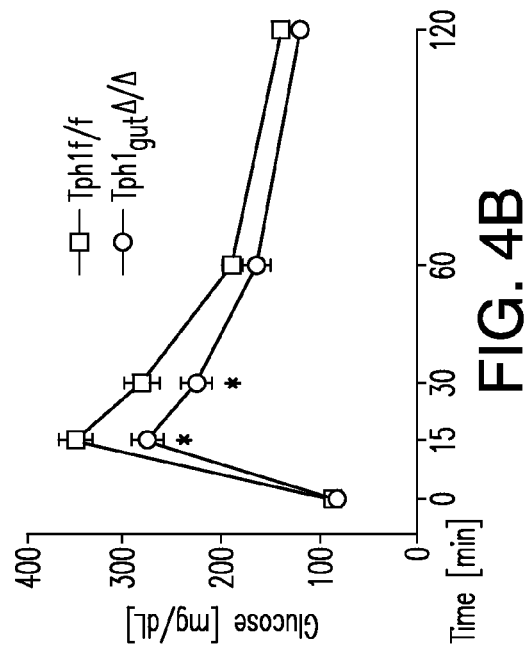
Figure 4E:
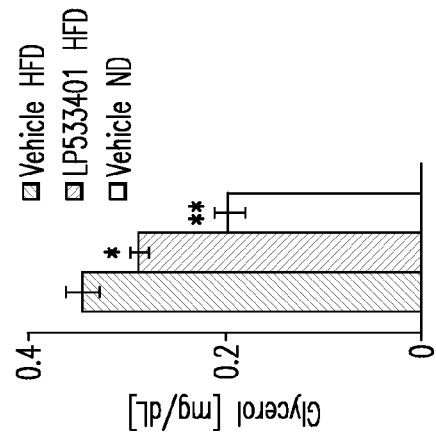
Figure 4G:
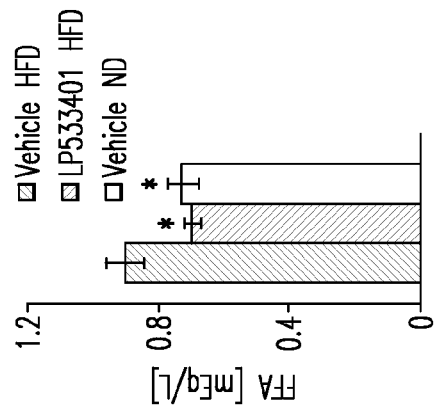
Figure 4F:
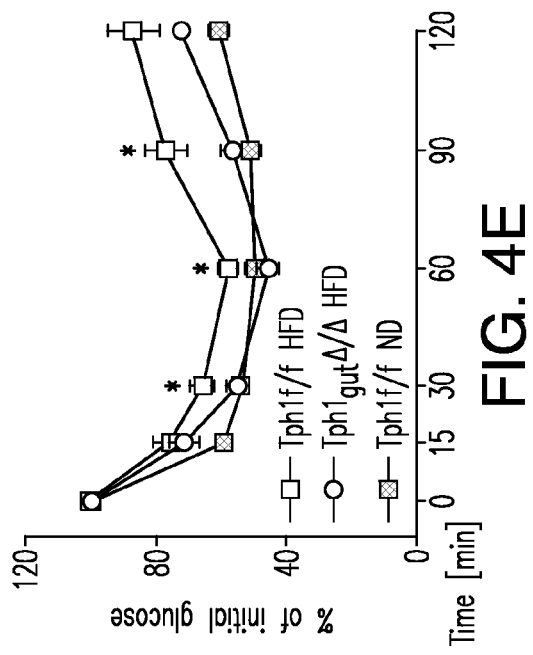
Figure 4H:
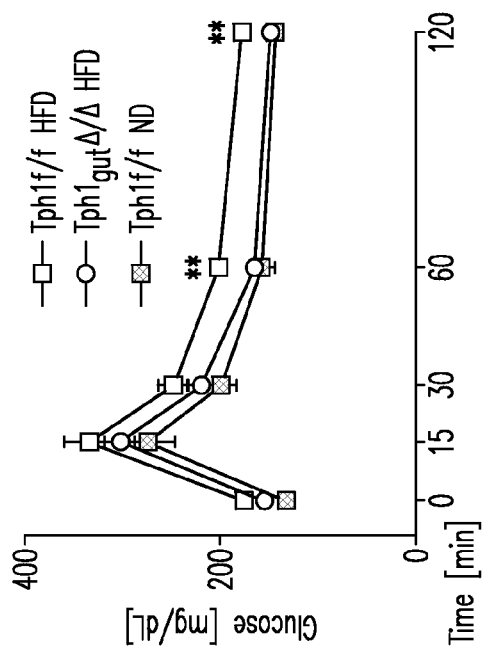
Figure 4J:
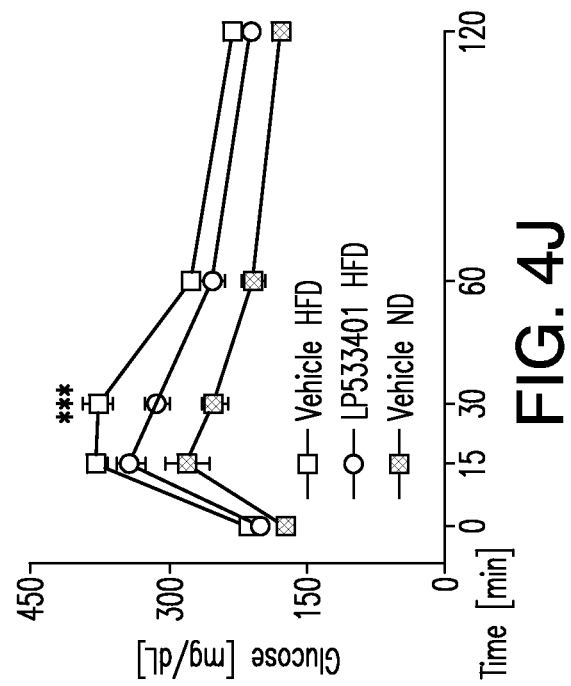
Figure 4I:
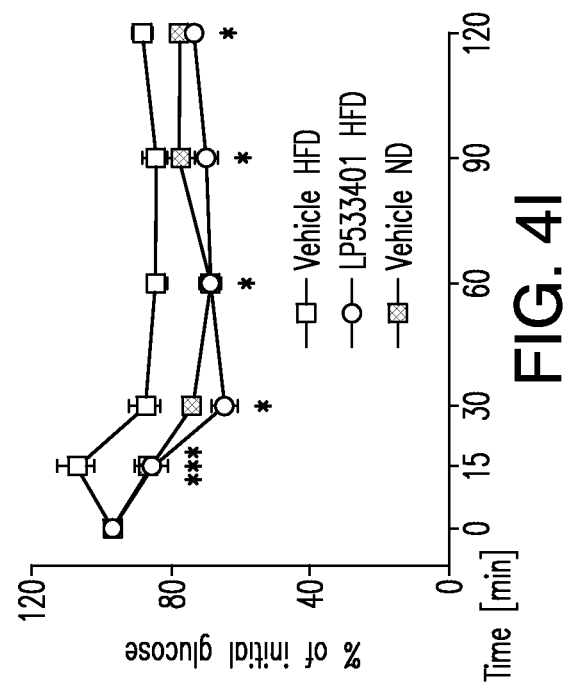
Figure 4K:
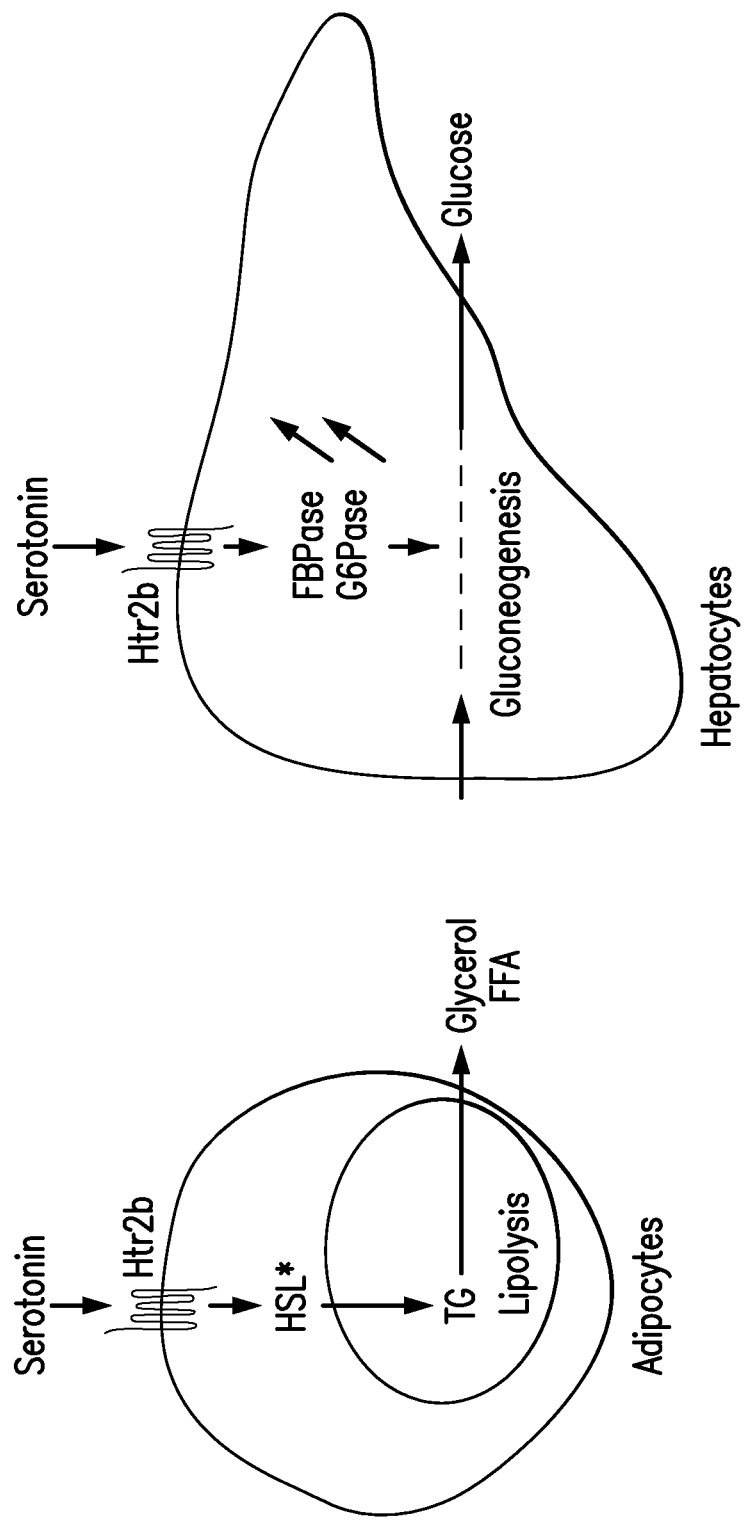

The results presented herein reveal that GDS is a hormone whose synthesis is induced by fasting and that opposes deleterious consequences of food deprivation. To do so, GDS favors glucose production by acting synergistically in adipocytes to promote release of glycerol, a substrate of gluconeogenesis, and in hepatocytes to actively promote gluconeogenesis (FIG. 4K). An important feature of this regulation is that pharmacological evidence indicates that it could be manipulated advantageously to fight Type II diabetes.

The results disclosed herein show that elevated serum or plasma serotonin increases blood glucose levels, leading to diabetes. Thus, certain embodiments of the invention are directed to methods for diagnosing and treating persons at risk of developing diabetes and to methods for treating or preventing diabetes by administering therapeutic agents that decrease the level of serum or plasma serotonin and thus decrease blood glucose levels.

One embodiment of the invention is directed to a method for determining if a patient is at risk of developing diabetes by measuring the patient's level of serum or plasma serotonin and then administering a therapeutic agent disclosed herein that is a TPH1 inhibitor to the patient if the patient's level of serum or plasma serotonin is elevated so as to indicate that the patient is at risk of developing diabetes. In one embodiment, if the patient's level of serum or plasma serotonin is known to be significantly higher (e.g., more than about 25% higher, more than about 50% higher, more than about 75% higher, more than about 100% higher) than the level in a normal subject, then the patient is at risk of developing diabetes and one or more TPH1 inhibitors that reduce serotonin synthesis, and thus serum or plasma serotonin levels, is administered to reduce (and preferably normalize) serum or plasma serotonin levels, thereby preventing diabetes from developing or minimizing the extent or the detrimental effects of diabetes, should diabetes develop. Patient monitoring will determine if an abnormal serum or plasma serotonin level is chronic. If it is chronic, then the patient may need to continue treatment over a prolonged period (e.g., for one month, six months, one year, two years, three years, or many years) to normalize serum or plasma serotonin levels and/or maintain normal levels of serum or plasma serotonin.

When a patient's level of serum or plasma serotonin is compared to the level of serum or plasma serotonin in a normal subject, it should be understood that "normal subject" refers to a person who is matched to the patient in those characteristics that would be expected to affect serum or plasma serotonin levels, e.g., gender, age, general health, medications being taken, etc.

Methods of Treatment and Prevention of Diabetes

The present invention provides a method of preventing or treating diabetes in a patient known or suspected to be in need of such prevention or treatment comprising administering to the patient a therapeutically effective amount of a therapeutic agent that decreases serum or plasma serotonin levels. In certain embodiments, the method comprises administering to the patient therapeutically effective amounts of two or more therapeutic agents disclosed herein that decrease serum or plasma serotonin levels.

TPH1 inhibitors that may be used in certain of the methods of the present invention include the following, including any racemic mixtures and individual enantiomers, pharmaceutically acceptable salts or solvates thereof:

(121)

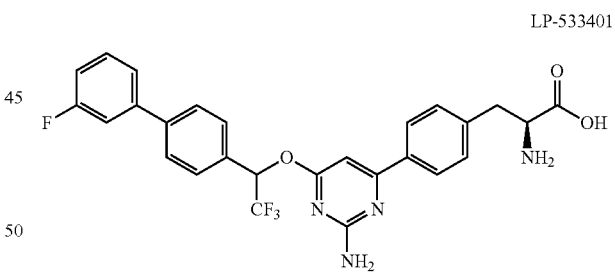

LP-533401

(122)

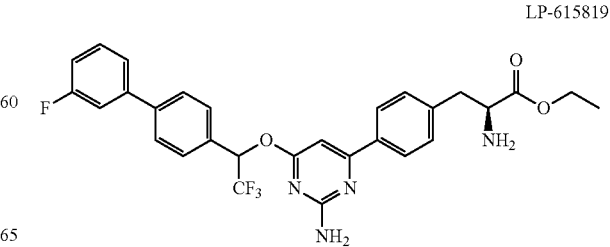

LP-615819

(123)

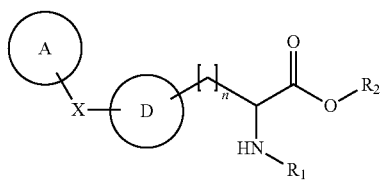

where A is optionally substituted cycloalkyl, aryl, or heterocycle; X is a bond (i.e., A is directly bound to D), —O—, —S—, —C(O)—, —C(R4)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3;

(124)

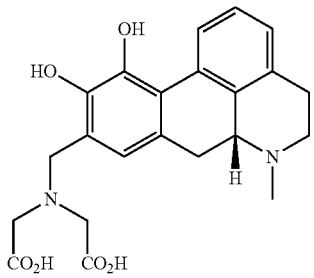

where A is optionally substituted cycloalkyl, aryl, or heterocycle; X is a bond (i.e., A is directly bound to D), —O—, —S—, —C(O)—, —C(R4)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3;

(125)

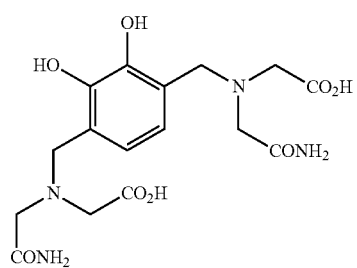 [SMILES: NC(=O)CN(CC(=O)O)Cc1ccc(CN(CC(N)=O)CC(=O)O)c(O)c1O]

(126)

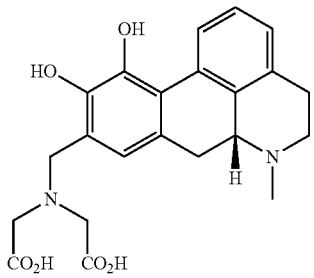

(127)

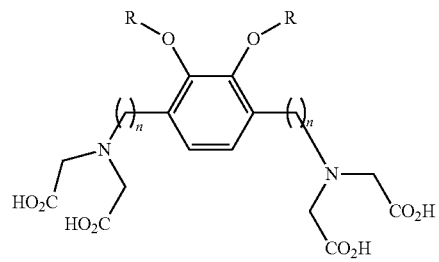

where R is hydrogen or lower alkyl; and n is 1, 2, or 3;

(128)

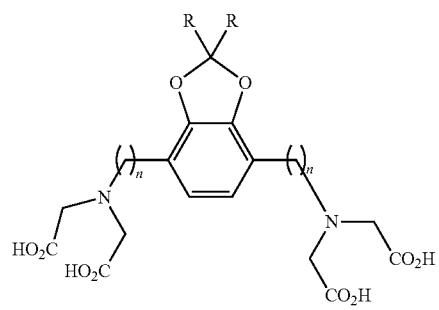

where R is hydrogen or lower alkyl; and n is 1, 2, or 3;

(129)

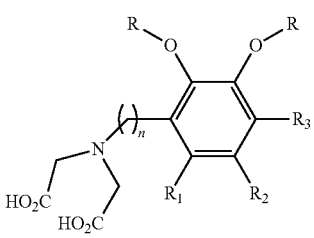

where R is hydrogen or lower alkyl;
$R_1$, $R_2$, and $R_3$, are independently:
hydrogen;
halogen;
lower alkyl;
alkoxy; or
amino; and
n is 1, 2, or 3;

(130)

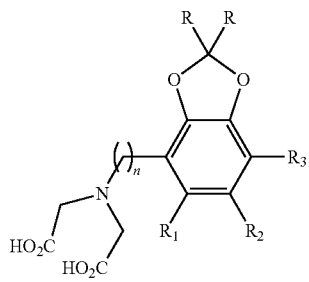

where R is hydrogen or lower alkyl;
$R_1$, $R_2$, and $R_3$, are independently:
  hydrogen;
  halogen;
  lower alkyl;
  alkoxy; or
  amino; and
n is 1, 2, or 3;

(131)

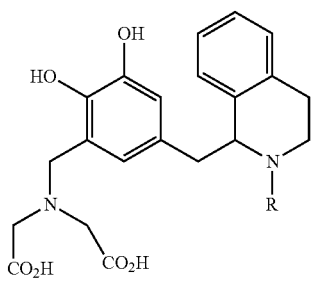

where R is hydrogen, lower alkyl, or cycloalkyl;

(132)

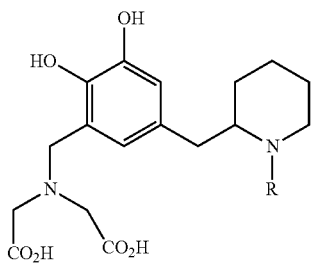

where R is hydrogen, lower alkyl, or cycloalkyl;

(133)

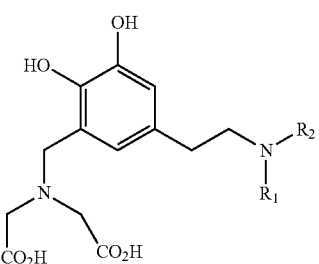

where $R_1$ and $R_2$ are independently hydrogen, lower alkyl, or cycloalkyl;

(134)

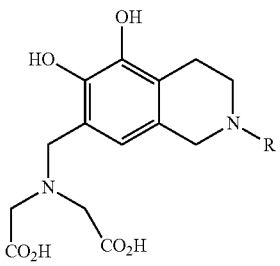

where R is hydrogen, lower alkyl, or cycloalkyl;

(135)

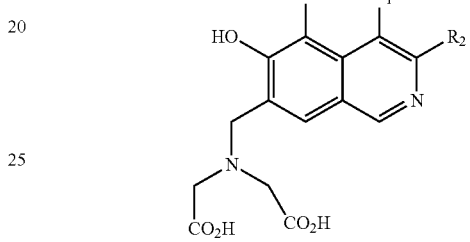

where $R_1$ and $R_2$ are independently hydrogen, lower alkyl, cycloalkyl, F, Cl, or OH;

(136)

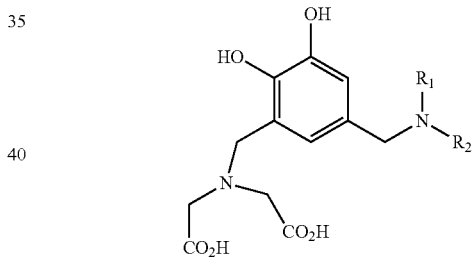

where $R_1$ and $R_2$ are independently hydrogen, lower alkyl, or cycloalkyl.

Other TPH1 inhibitors that may be used in the methods of the present invention include the following, including any racemic mixtures and individual enantiomers, pharmaceutically acceptable salts or solvates thereof:

(137)
(S)-2-Amino-3-(4-(4-amino-6-((R)-1-(naphthalen-2-yl)ethylamino)-1,3,5-triazin-2-yl)phenyl)propanoic acid;

(138)
(S)-2-Amino-3-(4-(4-amino-6-((4'-methylbiphenyl-4-yl)methylamino-1,3,5-triazin-2-yl)phenyl)propanoic acid;

(139)
(S)-2-Amino-3-(4-(4-morpholino-6-(naphthalen-2-ylmethylamino)-1,3,5-triazin-2-yl)phenyl)propanoic acid;

(140)
(2S)-2-Amino-3-(4-(2-amino-6-(2,2,2-trifluoro-1-(2-(trifluoromethyl)phenyl) ethoxy)pyrimidin-4-yl)phenyl)propanoic acid;

(141)
(2S)-2-Amino-3-(4-(2-amino-6-(2,2,2-trifluoro-1-p-tolylethoxy)pyrimidin-4-yl)phenyl)propanoic acid;

(142) (2S)-2-Amino-3-(4-(2-amino-6-(1-cyclohexyl-2,2,2-trifluoroethoxy)pyrimidin-4-yl(phenyl)propanoic acid;
(143) (S)-2-Amino-3-(4-(6-(2-fluorophenoxy)pyrimidin-4-yl)phenyl)propanoic acid;
(144) (2S)-2-Amino-3-(4-(4-(3-(4-chlorophenyl)piperidin-1-yl)-1,3,5-triazin-2-yl)phenyl)propanoic acid;
(145) (2S)-2-Amino-3-(4-(4-amino-6-(2,2,2-trifluoro-1-phenylethoxy)-1,3,5-triazin-2-yl)phenyl)propanoic acid;
(146) (S)-2-Amino-3-(5-(4-amino-6-((R)-(naphthalen-2-yl)ethylamino)-1,3,5-triazin-2-yl)pyridin-2-yl)propanoic acid;
(147) (S)-2-Amino-3-(3-(4-amino-6-(R)-1-(naphthalen-2-yl)ethylamino)-1,3,5-triazin-2-yl)-1H-pyrazol-1-yl)propanoic acid;
(148) (S)-2-Amino-3-(4'-(3-(cyclopentyloxy)-4-methoxybenzylamino)biphenyl-4-yl)propanoic acid;
(149) (S)-2-Amino-3-(4-(6-(3-(cyclopentyloxy)-4-methoxybenzylamino)pyrimidin-4-yl)phenyl)propanoic acid;
(150) (S)-2-Amino-3-(4-(6-(3-(cyclopentyloxy)-4-methoxybenzylamino)pyrazin-2-yl)phenyl)propanoic acid;
(151) (S)-2-Amino-3-(4-(5-((4'-methylbiphenyl-2-yl)methylamino)pyrazin-2-yl)phenyl)propanoic acid;
(152) (2S)-2-Amino-3-(4-(6-(2,2,2-trifluoro-1-phenylethoxy)-pyrimidin-4-yl)phenyl)propanoic acid;
(153) (2S)-2-Amino-3-(4-(6-(1-(3,4-difluorophenyl)-2,2,2-trifluoroethoxy)pyrimidin-4-yl)phenyl)propanoic acid;
(154) (S)-2-Amino-3-(4-(5-(3-(cyclopentyloxy)-4-methoxybenzylamino)-pyrazin-2-yl)phenyl)propanoic acid;
(155) (S)-2-Amino-3-(4-(5-((3-(cyclopentyloxy)-4-methoxybenzyl)-(methyl)amino)pyrazin-2-yl)phenyl)propanoic acid;
(156) (S)-2-Amino-3-(4-(5-((1,3-dimethyl-1H-pyrazol-4-yl)methylamino)pyrazin-2-yl)phenyl)propanoic acid;
(157) (S)-2-Amino-3-(4-(4-amino-6-((S)-1-(naphthalen-2-yl)ethylamino)-1,3,5-triazin-2-yloxy)phenyl)propanoic acid;
(158) (S)-2-Amino-3-(4-(4-amino-6-((R)-1-(biphenyl-2-yl)-2,2,2-trifluoroethoxy)-1,3,5-triazin-2-yl)phenyl)propanoic acid;
(159) (2S)-2-Amino-3-(4-(4-amino-6-(1-(6,8-difluoronaphthalen-2-yl)ethylamino)-1,3,5-triazin-2-yl)phenyl)propanoic acid;
(160) (2S)-2-Amino-3-(4-(4-amino-6-(2,2,2-trifluoro-1-(3'-methylbiphenyl-2-yl)ethoxy)-1,3,5-triazin-2-yl)phenyl)propanoic acid;
(161) (S)-2-Amino-3-(4-(5-(3,4-dimethoxyphenylcarbamoyl)-pyrazin-2-yl)phenyl)propanoic acid;
(162) (S)-2-Amino-3-(4-(2-amino-6-(4-(2-(trifluoromethyl)phenyl)-piperidin-1-yl)pyrimidin-4-yl)phenyl)propanoic acid;
(163) (S)-2-Amino-3-(4-(2-amino-6-((R)-1-(naphthalen-2-yl)ethylamino)pyrimidin-4-yl)phenyl)propanoic acid;
(164) (S)-2-Amino-3-(4-(2-amino-6-(methyl(R)-1-(naphthalen-2-yl)ethyl)amino)pyrimidin-4-yl)phenyl)propanoic acid;
(165) (S)-2-Amino-3-(4-(2-amino-6-((S)-2,2,2-trifluoro-1-(6-methoxynaphthalen-2-yl)ethoxy)pyrimidin-4-yl)phenyl)propanoic acid;
(166) (S)-2-Amino-3-(4-(5-(biphenyl-4-ylmethylamino)pyrazin-2-yl)phenyl)propanoic acid;
(167) (S)-2-Amino-3-(4-(5-(naphthalen-2-ylmethylamino)pyrazin-2-yl)phenyl)propanoic acid;
(168) (S)-2-(Tert-butoxycarbonylamino)-3-(4-(5-(naphthalen-2-ylmethylamino)pyrazin-2-yl)phenyl)propanoic acid;
(169) (S)-2-Morpholinoethyl 2-amino-3-(4-(5-(naphthalen-2-ylmethylamino)pyrazin-2-yl)phenyl)propanoate;
(170) (S)-2-Amino-3-(4-(2-amino-6-(2,2,2-trifluoro-1-(3'-fluorobiphenyl-4-yl)ethoxy)pyrimidin-4-yl)phenyl)propanoic acid;
(171) (S)-2-Amino-3-(4-(2-amino-6-(benzylthio)pyrimidin-4-yl)phenyl)propanoic acid;
(172) (S)-2-Amino-3-(4-(2-amino-6-(naphthalen-2-ylmethylthio)pyrimidin-4-yl)phenyl)propanoic acid;
(173) (2S)-2-Amino-3-(4-(2-amino-6-(1-(3,4-difluorophenyl)-2,2,2-trifluoroethoxy)pyrimidin-4-yl)phenyl)propanoic acid;
(174) (2S)-2-Amino-3-(4-(2-amino-6-(2,2,2-trifluoro-1-(3'-methylbiphenyl-2-yl)ethoxy)pyrimidin-4-yl)phenyl)propanoic acid;
(175) (S)-2-Amino-3-(4-(5-(3-(cyclopentyloxy)-4-methoxybenzylamino)pyridin-3-yl)phenyl)propanoic acid;
(176) 2-Amino-3-(3-(4-amino-6-((R)-1-(naphthalen-2-yl)ethylamino)-1,3,5-triazin-2-yl)phenyl)propanoic acid;
(177) 2-Amino-3-(4-(4-amino-6-((R)-1-(naphthalen-2-yl)ethylamino)-1,3,5-triazin-2-yl)-2-fluorophenyl)propanoic acid;
(178) (2S)-2-Amino-3-(4-(4-amino-6-(1-(adamantyl)ethylamino)-1,3,5-triazin-2-yl)phenyl)propanoic acid;
(179) (S)-2-Amino-3-(4-(5-fluoro-4-((R)-1-(naphthalen-2-yl)ethylamino)pyrimidin-2-yl)phenyl)propanoic acid;
(180) (S)-2-Amino-3-(4-(2-amino-6-(4-(trifluoromethyl)-benzylamino)pyrimidin-4-yl)phenyl) propanoic acid;
(181) 2-Amino-3-(5-(5-phenylthiophen-2-yl)-1H-indol-3-yl)propanoic acid;
(182) (S)-2-Amino-3-(4-(4-(4-phenoxyphenyl)-1H-1,2,3-triazol-1-yl)phenyl)propanoic acid;
(183) (S)-2-Amino-3-(4-(4-(4-(thiophene-2-carboxamido)phenyl)-1H-1,2,3-triazol-1-yl)phenyl)propanoic acid; and (184)

(S)-2-Amino-3-(4-(2-amino-6-(phenylethynyl)pyrimidin-4-yl)phenyl)propanoic acid;

Additional TPH1 inhibitors that may be used in the present invention include:

(185)

N-[(1R,4R,9aS)-4-phenyl octahydropyrido[2,1-c][1,4]oxazin-1-yl]3,4,5-trimethoxybenzamide;

(186)

2,6-Piperidinedione, 3-[3-(dimethylamino)propyl]-3-(3-methoxyphenyl)-4,4-dimethyl-, monohydrochloride;

(187)

Triptosine (CAS registry number 86248-47-7; U.S. Pat. No. 4,472,387);

(188)

pCPA

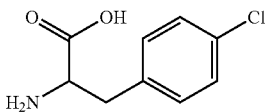

(189)

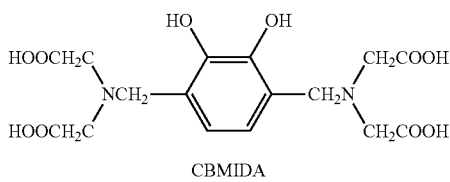

CBMIDA

Additional TPH1 inhibitors that may be used in the present invention are listed in the table below.

TABLE 1

(S)-2-amino-3-(4-(5-(2-fluoro-4,5-dimethoxybenzylamino)pyrazin-2-yl)phenyl)propanoic acid
(S)-2-amino-3-(4-(2-amino-6-(4-(2-methoxyphenyl)piperidin-1-yl)pyrimidin-4-yl)phenyl)propanoic acid
(S)-2-amino-3-(4-(6-(3-(cyclopentyloxy)-4-methoxybenzylamino)-2-(dimethylamino)pyrimidin-4-yl)phenyl)propanoic acid
(S)-2-amino-3-(4-(5-(3,4-dimethylbenzylamino)pyrazin-2-yl)phenyl)propanoic acid
(S)-2-amino-3-(4-(5-(biphenyl-2-ylmethylamino)pyrazin-2-yl)phenyl)propanoic acid
(S)-ethyl 2-amino-3-(4-(2-amino-6-(4-(trifluoromethyl)benzylamino)pyrmidin-4-yl)phenyl)propanoate
(S)-2-amino-3-(4-(5-(cyclopentylmethylamino)pyrazin-2-yl)phenyl)propanoic acid
(2S)-2-amino-3-(4-(2-amino-6-(3-(2-(trifluoromethyl)phenyl)pyrrolidin-1-yl)pyrimidin-4-yl)phenyl)propanoic acid
(2S)-2-amino-3-(4-(2-amino-6-(1,2,3,4-tetrahydronaphthalen-1-ylamino)pyrimidin-4-yl)phenyl)propanoic acid
(S)-2-amino-3-(4-(2-amino-6-((R)-1-(naphthalen-2-yl)ethoxy)pyrimidin-4-yl)phenyl)propanoic acid
(2S)-2-amino-3-(4-(2-amino-6-(1,2-diphenylethylamino)pyrimidin-4-yl)phenyl)propanoic acid
(S)-2-amino-3-(4-(2-amino-6-((R)-1-(4-(benzo[b]thiophen-3-yl)phenyl)ethylamino)pyrimidin-4-yl)phenyl)propanoic acid
(S)-2-amino-3-(4-(4-amino-6-((R)-1-(4'-methoxybiphenyl-4-yl)ethylamino)-1,3,5-triazin-2-yl)phenyl)propanoic acid
2-amino-3-(1-(4-amino-6-((R)-1-(naphthalon-2-yl)ethylamino)-1,3,5-triazin-2-yl)piperidin-4-yl)propanoic acid
(2S)-2-amino-3-(4-(4-amino-6-(1-(4-fluoronaphthalen-1-yl)ethylamino)-1,3,5-triazin-2-yl)phenyl)propanoic acid TABLE 1-continued (S)-2-amino-3-(4-(4-amino-6-((3'-fluorobiphenyl-4-yl)methylamino)-1,3,5-triazin-2-yl)phenyl)propanoic acid
2-amino-3-(4-(4-amino-6-((R)-1-(naphthalen-2-yl)ethylamino)-1,3,5-triazin-2-yl)-2-fluorophenyl)propanoic acid
(S)-2-amino-3-(4-(2-amino-6-((R)-2,2,2-trifluoro-1-(3'-methoxybiphenyl-4-yl)ethoxy)pyrimidin-4-yl)phenyl)propanoic acid
(2S)-2-amino-3-(4-(4-amino-6-(2,2,2-trifluoro-1-(3'-fluorobiphenyl-2-yl)ethoxy)-1,3,5-triazin-2-yl)phenyl)propanoic acid
(2S)-2-amino-3-(4-(4-amino-6-(1-(4-tert-butylphenyl)ethylamino)-1,3,5-triazin-2-yl)phenyl)propanoic acid
(2S)-2-amino-3-(4-(2-amino-6-(2,2,2-trifluoro-1-(3'-fluorobiphenyl-4-yl)ethoxy)pyrimidin-4-yl)phenyl)propanoic acid
(2S)-2-amino-3-(4-(4-amino-6-(6,7-dihydroxy-1-methyl-3-4-dihydroisoquinolin-2(1H)-yl)-1,3,5-triazin-2-yl)phenyl)propanoic acid
(2S)-2-amino-3-(4-(4-amino-6-(2,2,2-trifluoro-1-(3'-methylbiphenyl-4-yl)ethoxy)-1,3,5-triazin-2-yl)phenyl)propanoic acid
(S)-2-amino-3-(4-(4-amino-6-((R)-1-(naphthalen-2-yl)ethylamino)pyrimidin-2-yl)phenyl)propanoic acid
(S)-2-amino-3-(4-(2-amino-6-(benzylthio)pyrimidin-4-yl)phenyl)propanoic acid
(2S)-2-amino-3-(4-(2-amino-6-(2,2,2-trifluoro-1-(4'-fluorobiphenyl-4-yl)ethoxy)pyrimidin-4-yl)phenyl)propanoic acid
(2S)-2-amino-3-(4-(6-(3-(4-chlorophenoxy)piperidin-1-yl)pyrimidin-4-yl)phenyl)propanoic acid
(S)-3-(4-(4-amino-6-((R)-1-(naphthalen-2-yl)ethylamino)-1,3,5-triazin-2-yl)phenyl)-2-(2-aminoacetamido)propanoic acid
(S)-2-amino-3-(4-(6-((R)-1-(naphthalen-2-yl)ethylamino)-2-(trifluoromethyl)pyrimidin-4-yl)phenyl)propanoic acid
(S)-2-amino-3-(4-(2-amino-6-(4-(3-chlorophenyl)piperazin-1-yl)pyrimidin-4-yl)phenyl)propanoic acid
(S)-2-amino-3-(4-(2-amino-6-((R)-2,2,2-trifluoro-1-phenylethoxy)pyrimidin-4-yl)phenyl)propanoic acid
(2S)-2-amino-3-(4-(2-amino-6-(1,4-diphenylbutylamino)pyrimidin-4-yl)phenyl)propanoic acid
(2S)-2-amino-3-(4-(6-(1-(3'-chlorobiphenyl-2-yl)-2,2,2-trifluoroethoxy)pyrimidin-4-yl)phenyl)propanoic acid
(2S)-2-amino-3-(4-(4-amino-6-(1-(biphenyl-4-yl)-2,2,2-trifluoroethoxy)-1,3,5-triazin-2-yl)phenyl)propanoic acid
(2S)-2-amino-3-(4-(2-amino-6-(2,2,3,3,3-pentafluoro-1-(3-fluoro-4-methylphenyl)propoxy)pyrimidin-4-yl)phenyl)propanoic acid
(S)-ethyl 2-amino-3-(4-(2-amino-6-((R)-2,2,2-trifluoro-1-(3'-methoxybiphenyl-4-yl)ethoxy)pyrimidin-4-yl)phenyl)propanoate
(S)-2-amino-3-(4-(2-amino-6-((S)-2,2,2-trifluoro-1-(3'-methoxybiphenyl-4-yl)ethoxy)pyrimidin-4-yl)phenyl)propanoic acid
(2S)-2-amino-3-(4-(2-amino-6-(2,2,2-trifluoro-1-(3-fluoro-3'-methoxybiphenyl-4-yl)ethoxy)pyrimidin-4-yl)phenyl)propanoic acid
(2S)-2-amino-3-(4-(2-amino-6-(1-(3'-(dimethylamino)biphenyl-2-yl)-2,2,2-trifluoroethoxy)pyrimidin-4-yl)phenyl)propanoic acid
(2S)-2-amino-3-(4-(2-amino-6-(2,2,2-trifluoro-1-(3'-methoxy-5-methylbiphenyl-2-yl)ethoxy)pyrimidin-4-yl)phenyl)propanoic acid
(2S)-2-amino-3-(4-(2-amino-6-(2,2,2-trifluoco-1-4'-methoxy-5-methylbiphenyl-2-yl)ethoxy)pyrimidin-4-yl)phenyl)propanoic acid
(2S)-2-amino-3-(4-(2-amino-6-(2,2,2-trifluoro-1-(3'-methoxy-3-(methylsulfonyl)biphenyl-4-yl)ethoxy)pyrimidin-4-yl)phenyl)propanoic acid
(2S)-2-amino-3-(4-(2-amino-6-(1-(2-(cyclopropylmethoxy)-4-fluorophenyl)-2,2,2-trifluoroethoxy)pyrimidin-4-yl)phenyl)propanoic acid
(2S)-2-amino-3-(4-(6-(1-(2-(cyclopropylmethoxy)-4-fluorophenyl)-2,2,2-trifluoroethoxy)pyrimidin-4-yl)phenyl)propanoic acid
(2S)-2-amino-3-(4-(2-amino-6-(2,2,2-trifluoro-1-(2-(isopentyloxy)phenyl)ethoxy)pyrimidin-4-yl)phenyl)propanoic acid
(2S)-2-amino-3-(4-(5-(2,2,2-trifluoro-1-(3'-fluorobiphenyl-4-yl)ethoxy)pyrazin-2-yl)phenyl)propanoic acid TABLE 1-continued (2S)-2-amino-3-(4-(2-amino-6-(2,2,2-trifluoro-1-(4'-methoxybiphenyl-2-yl)ethoxy)pyrimidin-4-yl)phenyl)propanoic acid
(2S)-2-amino-3-(4-(2-amino-6-(1-(3'-carbamoylbiphenyl-2-yl)-2,2,2-trifluoroethoxy)pyrimidin-4-yl)phenyl)propanoic acid
(2S)-2-amino-3-(4-(2-amino-6-(1-(4'-carbamoylbiphenyl-2-yl)-2,2,2-trifluoroethoxy)pyrimidin-4-yl)phenyl)propanoic acid
(2S)-2-amino-3-(4-(2-amino-6-(2,2,2-trifluoro-1-(4-(2-methoxyphenoxy)phenyl)ethoxy)pyrimidin-4-yl)phenyl)propanoic acid
(2S)-2-amino-3-(4-(6-(2,2,2-trifluoro-1-(4-(2-methoxyphenoxy)phenyl)ethoxy)pyrimidin-4-yl)phenyl)propanoic acid
(2S)-2-amino-3-(4-(6-(2,2,2-trifluoro-1-(2-(isopentyloxy)phenyl)ethoxy)pyrimidin-4-yl)phenyl)propanoic acid
(2S)-3-(4-(6-(1-(3'-acetamidobiphenyl-2-yl)-2,2,2-trifluoroethoxy)-2-aminopyrimidin-4-yl)phenyl)-2-aminopropanoic acid
(2S)-3-(4-(6-(1-(4'-acetamidobiphenyl-2-yl)-2,2,2-trifluoroethoxy)-2-aminopyrimidin-4-yl)phenyl)-2-aminopropanoic acid
(2S)-2-amino-3-(4-(2-amino-6-(1-(4-cyanophenyl)-2,2,2-trifluoroethoxy)pyrimidin-4-yl)phenyl)propanoic acid
(S)-ethyl 2-amino-3-(4-(2-amino-6-((R)-2,2,2-trifluoro-1-p-tolylethoxy)pyrimidin-4-yl)phenyl)propanoate
(2S)-2-amino-3-(4-(2-amino-6-(2,2,2-trifluoro-1-(1-methoxybicyclo[2.2.2]oct-5-en-2-yl)ethoxy)pyrimidin-4-yl)phenyl)propanoic acid
(2S)-2-amino-3-(4-(2-amino-6-(1-(4-(cyclopentyloxy)phenyl)-2,2,2-trifluoroethoxy)pyrimidin-4-yl)phenyl)propanoic acid
(2S)-2-amino-3-(4-(6-(1-(4-(cyclopentyloxy)phenyl)-2,2,2-trifluoroethoxy)pyrimidin-4-yl)phanyl)proparioic acid
(2S)-2-amino-3-(4-(2-amino-6-(2,2,2-trifluoro-1-(4-(3-methoxyphenoxy)phenyl)ethoxy)pyrimidin-4-yl)phenyl)propanoic acid
(2S)-2-amino-3-(4-(2-amino-6-(1-(4,5-dimethoxybiphenyl-2-yl)-2,2,2-trifluoroethoxy)pyrimidin-4-yl)phenyl)propanoic acid
(2S)-2-amino-3-(4-(2-amino-6-(1-(4,5-dimethoxy-3'-methylbiphenyl-2-yl)-2,2,2-trifluoroethoxy)pyrimidin-4-yl)phenyl)propanoic acid
(2S)-2-amino-3-(4-(5-(2,2,2-trifluoro-1-(2'-methylbiphenyl-2-yl)ethoxy)pyrazin-2-yl)phenyl)propanoic acid
(2S)-2-amino-3-(4-(6-(2,2,2-trifluoro-1-(4-(3-methoxyphenoxy)phenyl)ethoxy)pyrimidin-4-yl)phenyl)propanoic acid
(2S)-2-amino-3-(4-(2-amino-6-(1-(2-(3,5-difluorophenoxy)phenyl)-2,2,2-trifluoroethoxy)pyrimidin-4-yl)phenyl)propanoic acid
(2S)-2-amino-3-(4-(2-amino-6-(2,2,2-trifluoro-1-(4-(4-methoxyphenoxy)phenyl)ethoxy)pyrimidin-4-yl)phenyl)propanoic acid
(2S)-2-amino-3-(4-(2-amino-6-(1-(4'-((S)-2-amino-2-carboxyethyl)biphenyl-2-yl)-2,2,2-trifluoroethoxy)pyrimidin-4-yl)phenyl)propanoic acid
(2S)-2-amino-3-(4-(2-amino-6-(1-(2-bromophenyl)-2,2,2-trifluoroethoxy)pyrimidin-4-yl)phenyl)propanoic acid
(2S)-2-amino-3-(4-(5-(2,2,2-trifluoro-1-(3'-methylbiphenyl-2-yl)ethoxy)pyrazin-2-yl)phenyl)propanoic acid
(2S)-2-amino-3-(4-(2-amino-6-(2,2,2-trifluoro-1-(4-methoxybiphenyl-2-yl)ethoxy)pyrimidin-4-yl)phenyl)propanoic acid
(2S)-2-amino-3-(4-(5-(2,2,2-trifluoro-1-(2-(4-methylthiophen-3-yl)phenyl)ethoxy)pyrazin-2-yl)phenyl)propanoic acid
(2S)-2-amino-3-(4-(2-amino-6-(2,2,2-trifluoro-1-(4-methoxy-3'-methylbiphenyl-2-yl)ethoxy)pyrimidin-4-yl)phenyl)propanoic acid
(2S)-2-amino-3-(4-(2-amino-6-(2,2,2-trifluoro-1-(3'-(hydroxymethyl)biphenyl-2-yl)ethoxy)pyrimidin-4-yl)phenyl)propanoic acid
(2S)-2-amino-3-(4-(2-amino-6-(1-(3'-cyanobiphenyl-2-yl)-2,2,2-trifluoroethoxy)pyrimidin-4-yl)phenyl)propanoic acid
(2S)-2-amino-3-(4-(6-(1-(2-(3,5-difluorophenoxy)phenyl)-2,2,2-trifluoroethoxy)pyrimidin-4-yl)phenyl)propanoic acid
(2S)-2-amino-3-(4-(6-(2,2,2-trifluoro-1-(4-(4-methoxyphenyl)ethoxy)pyrimidin-4-yl) phenyl)propanoic acid
(2S)-2-amino-3-(4-(2-amino-6-(2,2,2-trifluoro-1-(2-(4-methylthiazol-2-yl)thiophen-3-yl)ethoxy)pyrimidin-4-yl)phenyl)propanoic acid
(2S)-2-amino-3-(4-(2-amino-6-(2,2,2-trifluoro-1-(5-(4-methoxyphenyl)isoxazol-3-yl)ethoxy)pyrimidin-4-yl)phenyl)propanoic acid
(2S)-2-amino-3-(4-(2-amino-6-(2,2,2-trifluoro-1-(1-phenyl-5-(trifluoromethyl)-1H-pyrazol-4-yl)ethoxy)pyrimidin-4-yl)phenyl)propanoic acid
(2S)-2-amino-3-(4-(2-amino-6-(1-(2-(cyclohexyloxy)-4-methylphenyl)-2,2,2-trifluoroethoxy)pyrimidin-4-yl)phenyl)propanoic acid
(2S)-2-amino-3-(4-(2-amino-6-(1-(2-(cyclopentyloxy)-4-methylphenyl)-2,2,2-trifluoroethoxy)pyrimidin-4-yl)phenyl)propanoic acid
(2S)-2-amino-3-(4-(2-amino-6-(1-(benzo[d]thiazol-6-yl)2,2,2-trifluoroethoxy)pyrimidin-4-yl)phenyl)propanoic acid
(2S)-2-amino-3-(4-(2-amino-6-(2,2,2-trifluoro-1-(1-methyl-1H-imidazol-5-yl)ethoxy)pyrimidin-4-yl)phenyl)propanoic acid
(2S)-2-amino-3-(4-(6-(1-(2-(cyclopentyloxy)-4-methylphenyl)-2,2,2-trifluoroethoxy)pyrimidin-4-yl)phenyl)propanoic acid
(2S)-2-amino-3-(4-(6-(1-(2-(cyclohexyloxy)-4-methylphenyl)-2,2,2-trifluoroethoxy)pyrimidin-4-yl)phenyl)propanoic acid
(2S)-2-amino-3-(4-(2-amino-6-(2,2,2-trifluoro-1-(pyridin-3-yl)ethoxy)pyrimidin-4-yl)phenyl)propanoic acid
(2S)-2-amino-3-(4-(2-amino-6-(1-(1,3-dimethyl-1H-pyrazol-5-yl)-2,2,2-trifluoromethoxy)pyrimidin-4-yl)phenyl)propanoic acid
(S)-2-amino-3-(4-(2-amino-6-(3-hydroxyphenyl)pyrimidin-4-yl)phenyl)propanoic acid
(2S)-2-amino-3-(4-(2-amino-6-(2,2,2-trifluoro-1-(3'-hydroxybiphenyl-2-yl)ethoxy)pyrimidin-4-yl)phenyl)propanoic acid
(S)-2-amino-3-(4-(2-amino-6-(3,5-difluorophenyl)pyrimidin-4-yl)phenyl)propanoic acid
(2S)-2-amino-3-(4-(2-amino-6-(1-(3',5'-difluorobiphenyl-2-yl)-2,2,2-trifluoroethoxy)pyrimidin-4-yl)phenyl)propanoic acid
(2S)-2-amino-3-(4-(6-(2,2,2-trifluoro-1-(3'-fluorobiphenyl-3-yl)ethoxy)pyrazin-2-yl)phenyl)propanoic acid
(2S)-2-amino-3-(4-(2-amino-6-(1-(5-ethoxy-2-methyl-2,3-dihydrobenzofuran-6-yl)-2,2,2-trifluoroethoxy)pyrimidin-4-yl)phenyl)propanoic acid
(2S)-2-amino-3-(4-(2-amino-6-(1-(benzofuran-5-yl)-2,2,2-trifluoroethoxy)pyrmidin-4-yl)phenyl)propanoic acid
(2S)-2-amino-3-(4-(2-amino-6-(2,2,2-trifluoro-1-(2-m-tolylfuran-3-yl)ethoxy)pyrimidin-4-yl)phenyl)propanoic acid
(S)-ethyl 3-(4-(2-amino-6-((R)-2,2,2-trifluoro-1-(3'-methoxybiphenyl-4-yl)ethoxy)pyrimidin-4-yl)phenyl)-2-(2-aminoacetamido)propanoate
(2S)-2-amino-3-(4-(6-(2,2,2-trifluoro-1-(2-(4-methylthiophen-3-yl)phenyl)ethoxy)pyrazin-2-yl)phenyl)propanoic acid
(2S)-2-amino-3-(4-(2-amino-6-(2,2,2-trifluoro-1-(5-methyl-3-phenylisoxazol-4-yl)ethoxy)pyrimidin-4-yl)phenyl)propanoic acid
(S)-2-amino-3-(4-(2-amino-6-(3-(methylthio)phenyl)pyrimidin-4-yl)phenyl)propanoic acid
(2S)-2-amino-3-(4-(2-amino-6-(2,2,2-trifluoro-1-(3'-(methylthio)biphenyl-2-yl)ethoxy)pyrimidin-4-yl)phenyl)propanoic acid
(2S)-2-amino-3-(4-(2-amino-6-(1-(3'-((dimethylamino)methyl)biphenyl-2-yl)-2,2,2-trifluoroethoxy)pyrimidin-4-yl)phenyl)propanoic acid
(S)-2-amino-3-(4-(2-amino-6-(3-(trifluoromethoxy)phenyl)pyrimidin-4-yl)phenyl)propanoic acid
(2S)-2-amino-3-(4-(2-amino-6-(2,2,2-trifluoro-1-(3'-(trifluoromethoxy)biphenyl-2-yl)ethoxy)pyrimidin-4-yl)phenyl)propanoic acid
(S)-3-(4-(2-amino-6-((R)-2,2,2-trifluoro-1-(3'-methoxybiphenyl-4-yl)ethoxy)pyrimidin-4-yl)phenyl)-2-(2-aminoacetamido)propanoic acid
(2S)-2-amino-3-(4-(2-amino-6-(2,2,2-trifluoro-1-(1-methyl-5-phenyl-1H-pyrazol-4-yl)ethoxy)pyrimidin-4-yl)phenyl)propanoic acid
(2S)-2-amino-3-(4-(2-amino-6-(2,2,2-trifluoro-1-(4-(methylsulfonyl)phenyl)ethoxy)pyrimidin-4-yl)phenyl)propanoic acid
(S)-2-amino-3-(4-(2-amino-6-((R)-1-(3'-(dimethylamino)biphenyl-2-yl)-2,2,2-trifluoroethoxy)pyrimidin-4-yl)phenyl)propanoic acid
(2S)-2-amino-3-(4-(2-amino-6-(1-(2-chloro-4-(methylsulfonyl)phenyl)-2,2,2-trifluoroethoxy)pyrimidin-4-yl)phenyl)propanoic acid
(2S)-2-amino-3-(4-(2-amino-6-(2,2,2-trifluoro-1-(3-(furan-2-yl)thiophen-2-yl)ethoxy)pyrimidin-4-yl)phenyl)propanoic acid TABLE 1-continued (2S)-2-amino-3-(4-(2-amino-6-(1-(2-(cyclopentyloxy)-4-fluorophenyl)-2,2,2-trifluoroethoxy)pyrimidin-4-yl)phenyl)propanoic acid
(2S)-2-amino-3-(4-(2-amino-6-(2,2,2-trifluoro-1-(2-(3-methoxyphenyl)cyclohex-1-enyl)ethoxy)pyrimidin-4-yl)phenyl)propanoic acid
(2S)-2-amino-3-(4-(2-amino-6-(2,2,2-trifluoro-1-(pyrimidin-5-yl)ethoxy)pyrimidin-4-yl)phenyl)propanoic acid
(2S)-2-amino-3-(4-(5-(2,2,2-trifluoro-1-(3'-methoxybiphenyl-3-yl)ethoxy)pyrazin-2-yl)phenyl)propanoic acid
(S)-2-amino-3-(4-(2-amino-6-((S)-1-(3'-(dimethylamino)biphenyl-2-yl)-2,2,2-trifluoroethoxy)pyrimidin-4-yl)phenyl)propanoic acid
(2S)-2-amino-3-(4-(-amino-6-(2,2,2-trifluoro-1-(2-(furan-2-carboxamido)phenyl)ethoxy)pyrimidin-4-yl)phenyl)propanoic acid
(2S)-2-amino-3-(4-(2-amino-6-(1-(4-chloro-2-(methylsulfonyl)phenyl)-2,2,2-trifluoroethoxy)pyrimidin-4-yl)phenyl)propanoic acid
(S)-isopropyl 2-amino-3-(4-(2-amino-6-((R)-2,2,2-trifluoro-1-(3'-methoxybiphenyl-4-yl)ethoxy)pyrimidin-4-yl)phenyl)propanoate
(2S)-2-amino-3-(4-(6-(1-(2-(cyclopentyloxy)-4-fluorophenyl)-2,2,2-trifluoroethoxy)pyrimidin-4-yl)phenyl)propanoic acid
(2S)-2-amino-3-(4-(6-(1-(2-(cyclohexyloxy)-4-fluorophenyl)-2,2,2-trifluoromethoxy)pyrimidin-4-yl)phenyl)propanoic acid
(2S)-2-amino-3-(4-(2-amino-6-(2,2,2-trifluoro-1-(1-(thiophen-2-yl)cyclohexyl)ethoxy)pyrimidin-4-yl)phenyl)propanoic acid
(2S)-2-amino-3-(4-(2-(2,2,2-trifluoro-1-(3'-methoxybiphenyl-4-yl)ethoxy)thiazol-5-yl)phenyl)propanoic acid
(2S)-2-amino-3-(4-(2-amino-6-(1-(2-(cyclohexyloxy)-4-fluorophenyl)-2,2,2-trifluoroethoxy)pyrimidin-4-yl)phenyl)propanoic acid
(2S)-2-amino-3-(4-(2-amino-6-(2,2,2-trifluoro-1-(1-(4 methoxyphenyl)cyclohexyl)ethoxy)pyrimidin-4-yl)phenyl)propanoic acid
(2S)-2-amino-3-(4-(6-(2,2,2-trifluoro-1-(4-fluoro-2-methylphenyl)ethoxy)pyrimidin-4-yl)phenyl)propanoic acid
(2S)-2-amino-3-(4-(2-amino-6-(2,2,2-trifluoro-1-(4-fluoro-2-methylphenyl)ethoxy)pyrimidin-4-yl)phenyl)propanoic acid
(2S)-2-amino-3-(4-(2-amino-6-(oxazol-2-yl(phenyl)methoxy)pyrimidin-4-yl)phenyl)propanoic acid
(S)-2-amino-3-(4-(2-amino-6-(1-cyclohexyl-2,2,2-trifluoroethylideneaminooxy)pyrimidin-4-yl)phenyl)propanoic acid
(2S)-2-amino-3-(4-(2-amino-6-(1-(2-(3-(dimethylamino)phenyl)furan-3-yl)-2,2,2-trifluoroethoxy)pyrimidin-4-yl)phenyl)propanoic acid
(2S)-2-amino-3-(4-(2-amino-6-(2,2,2-trifluoro-1-(5-phenylthiophen-2-yl)ethoxy)pyrimidin-4-yl)phenyl)propanoic acid
(S)-phenyl 2-amino-3-(4-(2-amino-6-((R)-2,2,2-trifluoro-1-(3'-methoxybiphenyl-4-yl)ethoxy)pyrimidin-4-yl)phenyl)propanoate
(S)-2-amino-3-(4-(2-amino-6-((R)-1-(3'-((dimethylamino)methyl)biphenyl-4-yl)-2,2,2-trifluoroethoxy)pyrimidin-4-yl)phenyl)propanoic acid
(S)-2-amino-3-(4-(1-(3-methoxybenzoyl)-1H-pyrazol-4-yl)phenyl)propanoic acid
(2S)-2-amino-3-(4-(6-(2,2,2-trifluoro-1-(5-phenylfuran-2-yl)ethoxy)pyrimidin-4-yl)phenyl)propanoic acid
(2S)-2-amino-3-(4-(2-amino-6-(1-(4-chloro-2-fluorophenyl)-2,2,2-trifluoroethoxy)pyrimidin-4-yl)phenyl)propanoic acid
(S,E)-2-amino-3-(4-(2-amino-6-(4-(trifluoromethyl)styryl)pyrimidin-4-yl)phenyl)propanoic acid
(2S)-2-amino-3-(4-(2-amino-6-(1-(3,4-dichlorophenyl)-2,2,2-trifluoroethoxy)pyrimidin-4-yl)phenyl)propanoic acid
(2S)-2-amino-3-(4-(2-amino-6-(1-(4-chloro-3-fluorophenyl)-2,2,2-trifluoroethoxy)pyrimidin-4-yl)phenyl)propanoic acid
(S)-2-amino-3-(4-(2-amino-6-((R)-1-(3'-(dimethylamino)biphenyl-4-yl)-2,2,2-trifluoroethoxy)pyrimidin-4-yl)phenyl)propanoic acid
(2S)-2-amino-3-(4-(2-amino-6-(1-chloro-2,2,2-trifluoro-1-(4-methoxybiphenyl-2-yl)ethoxy)pyrimidin-4-yl)phenyl)propanoic acid
(2S)-2-amino-3-(4-(6-(2,2,2-trifluoro-1-(5-phenylthiophen-2-yl)ethoxy)pyrimidin-4-yl)phenyl)propanoic acid
(S)-2-amino-3-(4-(5-(4-phenoxyphenyl)-1H-1,2,3-triazol-1-yl)phenyl)propanoic acid
(S,E)-2-amino-3-(4-(2-amino-6-(2-(biphenyl-4-yl)vinyl)pyrimidin-4-yl)phenyl)propanoic acid
(S)-2-amino-3-(4-(4-amino-6-((R)-2,2,2-trifluoro-1-(3'-methoxybiphenyl-4-yl)ethoxy)pyrimidin-2-yl)phenyl)propanoic acid
(S)-2-amino-3-(4-(4'-methoxybiphenyl-4-ylsulfonamido)phenyl)propanoic acid
(S)-2-amino-3-(4-(2-amino-6-(2,2,2-trifluoro-1-(6-(3-methoxyphenyl)pyridin-3-yl)ethoxy)pyrimidin-4-yl)phenyl)propanoic acid
(S)-2-amino-3-(4-(2-amino-6-(2,2,2-trifluoro-1-(6-(2-fluoro-3-methoxyphenyl)pyridin-3-yl)ethoxy)pyrimidin-4-yl)phenyl)propanoic acid
2-amino-3-(5-(4'-methylbiphenyl-4-yl)-1H-indol-3-yl)propanoic acid
2-amino-3-(5-m-tolyl-1H-indol-3-yl)propanoic acid
(2S)-2-amino-3-(4-(2-(2-methoxyphenyl)furan-3-carboxamido)phenyl)propanoic acid
2-amino-3-(5-(1-benzyl-1H-pyrazol-4-yl)-1H-indol-3-yl)propanoic acid
(2S)-2-amino-3-(4-(2-amino-6-(2,2,2-trifluoro-1-(6-(thiophen-2-yl)pyridin-3-yl)ethoxy)pyrimidin-4-yl)phenyl)propanoic acid
2-amino-3-(6-(1-benzyl-1H-pyrazol-4-yl)-1H-indol-3-yl)propanoic acid
(S)-2-amino-3-(4-((2-(4-(trifluoromethyl)phenyl)thiazol-4-yl)methylamino)phenyl)propanoic acid
(S)-2-amino-3-(4-((4'-methoxybiphenyl-4-ylsulfonamido)methyl)phenyl)propanoic acid
(S)-2-amino-3-(4-(3-(2-methoxydibenzo[b,d]furan-3-yl)ureido)phenyl)propanoic acid
(S)-2-amino-3-(4-(3-(2,2-diphenylethyl)ureido)phenyl)propanoic acid
(S)-2-amino-3-(4-(phenylethynyl)phenyl)propanoic acid
(S)-2-amino-3-(4-(2-amino-6-((5-(1-methyl-5-(trifluoromethyl)-1H-pyrazol-3-yl)thiophen-2-yl)methoxy)pyrimidin-4-yl)phenyl)propanoic acid
(2S)-2-amino-3-(4-(2-amino-6-(1,1,1-trifluoro-3-((R)-2,2,3-trimethylcyclopent-3-enyl)propan-2-yloxy)pyrimidin-4-yl)phenyl)propanoic acid
(2S)-2-amino-3-(4-(2-amino-6-(3-(2-hydroxyethylcarbamoyl)piperidin-1-yl)pyrimidin-4-yl)phenyl)propanoic acid
(2S)-2-amino-3-(4-(2-amino-6-(3-(pyridin-2-yloxy)piperidin-1-yl)pyrimidin-4-yl)phenyl)propanoic acid
(S)-2-amino-3-(4-(2-amino-6-(4-chloro-3-(piparidine-1-carbonyl)phenyl)pyrimidin-4-yl)phenyl)propanoic acid In certain embodiments, the TPH1 inhibitors disclosed herein reduce serum or plasma serotonin to a level that is at least about 10% less than the level before treatment with the TPH1 inhibitor. In certain embodiments, the TPH1 inhibitor reduces serum or plasma serotonin to a level that is about 10% less, about 20% less, about 30% less, about 40% less, about 50% less, about 60% less, about 70% less, about 80% less, or about 90% less, than the level before treatment with the TPH1 inhibitor.

In certain embodiments, the methods described herein result in a decrease in blood glucose levels of at least about 5%, at least about 10%, at least about 15%, at least about 20%, at least about 25%, at least about 30%, at least about 35%, at least about 40%, at least about 45%, at least about 50%, at least about 55%, or at least about 60%. In certain embodiments, the methods described herein result in a decrease in blood glucose levels of at least about 5 mg/dl, at least about 10 mg/dl, at least about 15 mg/dl, at least about 20 mg/dl, at least about 25 mg/dl, at least about 30 mg/dl, at least about 35 mg/dl, at least about 40 mg/dl, at least about 45 mg/dl, at least about 50 mg/dl, at least about 55 mg/dl, or at least about 60 mg/dl. In certain embodiments, the methods described herein result in a decrease in blood glucose levels of 5-50%, 10-40%, 15-35%, or 20-30%. In certain embodiments, the methods described herein result in a decrease in blood glucose levels of from 5-50 mg/dl, 10-40 mg/dl, 15-35 mg/dl, or 20-30 mg/dl. In certain embodiments, the methods described herein result in a decrease in blood glucose levels of 5-10%, 10-20%, 20-30%, 30-40%, or 40-50%. In certain embodiments, the methods described herein result in a decrease in blood glucose levels of from 5-10 mg/dl, 10-20 mg/dl, 20-30 mg/dl, 30-40 mg/dl, or 40-50 mg/dl.

Synthesis of the compounds described herein can be carried out by methods similar to those disclosed in U.S. Patent Application Publication US 2007/0191370, U.S. Patent Application Publication US 2008/0153852, U.S. Patent Application Publication US 2009/0005381, and U.S. Patent Application Publication US 2009/0029993. Moieties such as A, X, D, and E can be prepared and linked according to the methods described in those patent applications. By choosing suitable starting materials for the remaining portion of the structures disclosed herein, the remaining portion can be incorporated with the A-X-D or A-X-D-E portion in the final structure and thus the compounds disclosed herein can be prepared.

One skilled in the art would be guided by other publications. For instance, one skilled in the art could consult the Examples in International Patent Publication WO 2010/056992 and could, for example, choose intermediates such as the following from Scheme 1 of Example 9

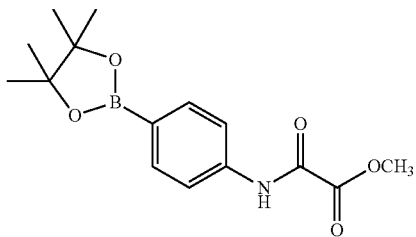 [SMILES: COC(=O)C(=O)Nc1ccc(B2OC(C)(C)C(C)(C)O2)cc1]

and link the intermediate compounds to suitable moieties such as A, $X_1$, D, and E that had been prepared according to the disclosures of the patent applications described above. By choosing other intermediates similar to the intermediate shown above, one skilled in the art could readily synthesize other TPH1 inhibitors disclosed herein.

Synthesis of specific compounds disclosed herein as well as the compounds within the generic formulas disclosed herein can also be carried out by methods similar to those disclosed in International Patent Publication WO 2007/089335 and International Patent Publication WO 2008/073933. Moieties such as A, X, D, and E can be prepared and linked according to the methods described in WO 2007/089335, in particular the methods disclosed at pages 35-41. Further methods that can be turned to for guidance are shown on pages 14-17 of WO 2008/073933. By choosing suitable starting materials for the remaining portion of the structures disclosed herein (e.g., the $X^1$-2-oxoacetate or $X^1$-2-oxoacetic acid moiety in certain of the generic formulas described above), the remaining portion can be incorporated with the A-X-D or A-X-D-E portion in the final structure and thus the compounds of the present invention can be prepared.

Certain compounds disclosed herein can be prepared according to the methods disclosed in International Patent Publication WO 2009/123978 or International Patent Publication WO 2010/056992, incorporated herein by reference in their entireties and specifically for the purpose of their disclosures of the synthesis of the compounds disclosed herein.

The present invention also encompasses the use of certain derivatives of the TPH1 inhibitors disclosed herein. For example, prodrugs of the TPH1 inhibitors could be produced by esterifying the carboxylic acid functions of the TPH1 inhibitors with a lower alcohol, e.g., methanol, ethanol, propanol, isopropanol, butanol, etc. The use of prodrugs of the TPH1 inhibitors that are not esters is also contemplated. For example, pharmaceutically acceptable carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of the TPH1 inhibitors are also contemplated. In some embodiments, the prodrugs will contain a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Guidance for the preparation of prodrugs of the TPH1 inhibitors disclosed herein can be found in publications such as *Design of Prodrugs*, Bundgaard, A. Ed., Elsevier, 1985; *Design and Application of Prodrugs, A Textbook of Drug Design and Development*, Krosgaard-Larsen and H. Bundgaard, Ed., 1991, Chapter 5, pages 113-191; and Bundgaard, H., Advanced Drug Delivery Review, 1992, 8, pages 1-38.

In certain embodiments, the TPH1 inhibitor inhibits TPH1 without significantly affecting the level of brain-derived serotonin. Methods of obtaining such inhibitors include: (1) screening for compounds that inhibit TPH1 to a much greater extent than TPH2; and (2) screening for compounds that, while they inhibit both TPH1 and TPH2, cannot cross the blood brain barrier and thus are effectively specific for TPH1 when administered to the patient outside the central nervous system. Of course, compounds that both inhibit TPH1 to a much greater extent than TPH2 and cannot cross the blood brain barrier are also suitable. Preferably, compounds that inhibit TPH1 to a much greater extent than TPH2 have an $IC_{50}$ for TPH2 that is at least about 10-fold greater than their $IC_{50}$ for TPH1.

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

A chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol, and pyridin-4-ol.

If the stereochemistry of a structure or a portion of a structure is not indicated with, for example, bold or dashed lines or wedges, the structure or the portion of the structure is to be interpreted as encompassing all stereoisomers of it, unless the chemical name associated with the structure indicates otherwise. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. When the stereochemistry of a structure or a portion of a structure is indicated with, for example, a bold or dashed line, the use of that structure in the methods describe herein encompasses the use of the indicated stereochemistry substantially free of any of the non-indicated structure. For example, such use includes the use of the indicated structure where the indicated structure is present in an enantiomeric excess of 95%, 96%, 97%, 98%, 99%, or 99.5%, Notwithstanding the above, it is understood that the methods of the invention may encompass the use of pure R and S enantiomers of the compounds disclosed herein as well as racemic mixtures. Thus, the disclose of the use of a compound without indication of any particular stereochemistry should be considered a disclosure of the use of that compound in the form of all racemic mixtures (e.g., a mixture of about 50% R and 50% S enantiomers) as well as a disclosure of the use of essentially pure enantiomers (i.e., about 100% R or about 100% S enantiomers).

In certain embodiments of the invention, a therapeutically effective amount of one or more of the TPH1 inhibitors described herein is administered in combination with other compounds or medications that are known to prevent or treat diabetes to a subject who has or is at risk of developing diabetes in order to treat or prevent diabetes. Classes of such compounds or medications include: insulin biguanides, meglitinides, sulfonylureas, thiazolidinediones, alpha glucosidase inhibitors, dipeptidyl peptidase inhibitors, and ergot alkaloids. Particular compounds or medications include: metformin (GLUCOPHAGE®, GLUCOPHAGE XR®, GLUMETZA®, RIOMET®, FORTAMET®), repaglinide (PRANDIN®), nateglinide (STARLIX®), Chlorpropamide (DIABINESE®), Glimepiride (AMARYL®), glipizide (GLUCOTROL®), glyburide (DIABETA®, MICRONASE®, GLYNASE®), Tolazamide (TOLINASE®), Tolbutamide (ORINASE®), pioglitazone (ACTOS®), rosiglitazone (AVANDIA®), acarbose (PRECOS®), miglitol (GLYSET®), sitagliptide (JANUVIA®), saxagliptin (ONGLYZA®), and bromocriptine (CYCLOSET®).

In certain embodiments, the TPH1 inhibitor is administered to a patient in need of treatment or prevention of diabetes in combination with an inhibitor of hormone sensitive lipase (HSL). For example, the TPH1 inhibitor may be administered with one or more of the following HSL inhibitors:

Methylphenylcarbamic acid 5-(4-isobutyl-2,6,-dioxopiperazin-1-yl)pyridinyl-2-yl ester

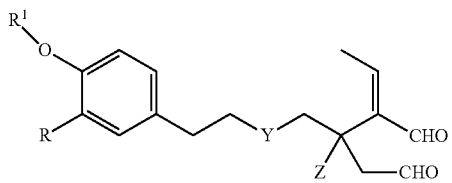

See International Patent Publication WO 2006/087308.

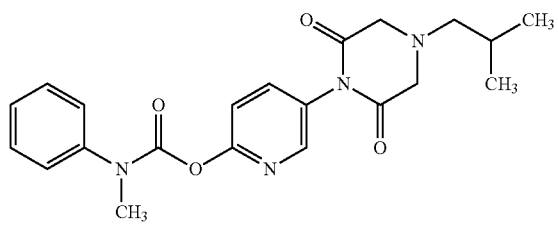

wherein R is hydrogen, hydroxyl or —OR$^1$;

wherein R$^1$ is hydrogen or a chemical moiety that can be cleaved in vivo to release a hydroxyl group and includes, for example, aliphatic or aromatic acyl (to form an ester bond) and the like. Such aliphatic or aromatic groups can include a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group, a carbalkoxy, a carbaryloxy, —SO$_3$H and —SO$_3$R$^3$, —P(O)(OH)$_2$, or —P(O)(OR$^3$)$_2$;

wherein R$^3$ is a saturated or unsaturated aliphatic group, substituted or unsubstituted aliphatic group, substituted or unsubstituted saturated or unsaturated alicyclic group, substituted or unsubstituted aromatic group, substituted or unsubstituted heteroaromatic group, substituted or unsubstituted heterocyclic group, glucuronide or glucuronide ester, —P(O)(OH)$_2$, and —P(O)(OR$^3$)$_2$;

wherein Y is —(CH$_2$)$_m$— where m=1 or 2, —OC(O)—, —O(CH$_2$)$_m$— where m=1 or 2, or —S(O)$_n$(CH$_2$)$_m$— where m=1 or 2; n=0, 1 or 2;

wherein Z is hydrogen, CH$_3$, F, Cl, Br or I.

See International Patent Publication WO 2007/081808.

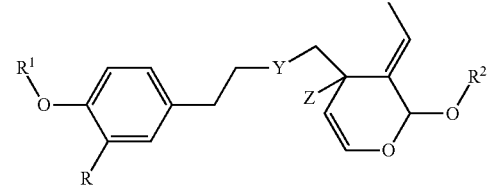

wherein R, R$^1$, R$^3$, Y and Z are as defined in the previous paragraph; and, wherein R$^2$ is hydrogen or a hydroxyl protecting group, as described in "Protective Groups in Organic Synthesis" by Theodora W. Greene, Peter G. M. Wuts, 1999, 3$^{rd}$ edition, pp 17-200, —SO$_3$H and —SO$_3$R$^3$ where R$^3$ is a saturated or unsaturated aliphatic group; a substituted or unsubstituted saturated or unsaturated alicyclic group.

See International Patent Publication WO 2007/081808.

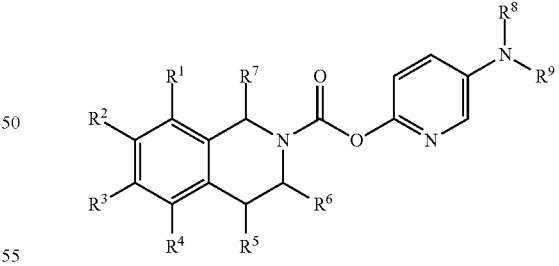

wherein R$^1$, R$^2$, R$^3$, R$^4$, R$^5$, R$^6$, and R$^7$, independent of each other, each represents hydrogen, hydroxy, mercapto, amino, —CONH$_2$, —CSNH$_2$, —NH—CO—NH$_2$, —NH—CS—NH$_2$, halogen, —S(=O)$_2$(OH), C$_{1-6}$-alkyl, C$_{1-6}$-alkoxy, C$_{2-6}$-alkenyl, aryl, heteroaryl, C$_{3-8}$-heterocyclyl and C$_{3-13}$-cycloalkyl, wherein each of hydroxy, mercapto, amino, —CONH$_2$, —NH—CO—NH$_2$, —NH—CS—NH$_2$, —CSNH$_2$, —S(=O)$_2$(OH), C$_{1-6}$-alkyl, C$_{1-6}$-alkoxy, C$_{2-6}$-alkenyl, aryl, heteroaryl, C$_{3-8}$-heterocyclyl and C$_{3-13}$-cycloalkyl may optionally be substituted with one or more substituents independently selected from hydroxy, mercapto, oxo (=O), thioxo halogen, amino, —S(=O)$_2$(OH), C$_{1-6}$-alkoxy, C$_{2-6}$-alkenyl, aryl, heteroaryl, C$_{3-6}$-heterocyclyl, and C$_{3-13}$-cycloalkyl, wherein each of hydroxy, mercapto, —S(=O)$_2$(OH), C$_{1-6}$-alkyl, C$_{1-6}$-alkoxy, C$_{2-6}$-alkenyl, aryl, heteroaryl, C$_{3-8}$-heterocyclyl and C$_{3-13}$-cycloalkyl may optionally be substituted with one or more substituents independently selected from hydroxy, mercapto, oxo, halogen, amino, —S(=O)$_2$(OH), halo-C$_{1-4}$-alkyl, halo-C$_{1-4}$-alkoxy, C$_{1-6}$-alkyl, C$_{1-6}$-alkoxy, C$_{2-6}$-alkenyl, aryl, heteroaryl, C$_{3-8}$-heterocyclyl, and C$_{3-13}$-cycloalkyl; and either R$^8$ is hydrogen and R$^9$ represents C$_{3-8}$-heterocyclyl which, optionally, is substituted with one or more substituents independently selected from hydroxy, mercapto, oxo (=O), thioxo (=S), halogen, amino, —S(=O)$_2$(OH), C$_{1-6}$-alkyl, C$_{1-6}$-alkoxy, C$_{2-6}$-alkenyl, aryl, heteroaryl, heterocycyl, and C$_{3-13}$-cycloalkyl; or R$^8$ together with R$^9$ and together with the adjacent nitrogen atom represents C$_{3-8}$-heterocyclyl which, optionally, is substituted with one or more substituents independently selected from hydroxy, mercapto, oxo (=O), thioxo (=S), halogen, amino, —S(=O)$_2$(OH), C$_{1-6}$-alkyl, C$_{1-6}$-alkoxy, C$_{2-6}$-alkenyl, aryl, heteroaryl, C$_{3-8}$-heterocyclyl, and C$_{3-13}$-cycloalkyl; or a pharmaceutically acceptable salt thereof, or a pharmaceutically acceptable solvate thereof, or any tautomeric forms, stereoisomers, mixture of stereoisomers including a racemic mixture, or polymorphs.
See International Patent Publication WO 2006/087309.

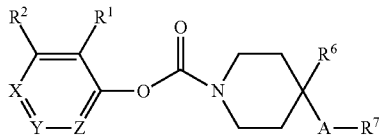

wherein
R$^1$ and R$^2$ are independently selected from hydrogen, hydroxy, sulfanyl, amino, halogen, sulfo, C$_{1-6}$-alkyl, C$_{1-6}$-alkoxy, C$_{2-6}$-alkenyl, aryl, heteroaryl, C$_{3-8}$-heterocyclyl and C$_{3-10}$-cycloalkyl, wherein each of hydroxy, sulfanyl, sulfo, C$_{1-6}$-alkyl, C$_{1-6}$-alkoxy, C$_{2-6}$-alkenyl, aryl, heteroaryl, C$_{3-8}$-heterocyclyl and C$_{3-10}$-cycloalkyl may optionally be substituted with one or more substituents independently selected from hydroxy, sulfanyl, oxo, halogen, amino, sulfo, perhalomethyl, perhalomethoxy, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl, wherein each of hydroxy, sulfanyl, sulfo, C$_{1-6}$-alkyl, C$_{1-6}$-alkoxy, C$_{2-6}$-alkenyl, aryl, heteroaryl, C$_{3-8}$-heterocyclyl and C$_{3-10}$-cycloalkyl may optionally be substituted with one or more substituents independently selected from hydroxy, sulfanyl, oxo, halogen, amino, sulk), perhalomethyl, perhalomethoxy, C$_{1-6}$-alkyl, C$_{1-6}$-alkoxy, C$_{2-6}$-alkenyl, aryl, heteroaryl. C$_{3-8}$-heterocyclyl, and C$_{3-10}$-cycloalkyl;
X is N or C—R$^3$; V is N or C—R$^4$; Z is N or C—R$^5$;
R$^3$, R$^4$ and R$^6$ are independently selected from hydrogen, hydroxy, sulfanyl, amino, sulfo, C$_{1-6}$-alkyl, C$_{2-6}$-alkenyl, aryl, heteroaryl, C$_{3-8}$-heterocyclyl and C$_{3-10}$-cycloalkyl, wherein each of hydroxy, sulfanyl, amino, sulfo, C$_{1-6}$-alkyl, C$_{2-6}$-alkenyl, aryl, heteroaryl, C$_{3-8}$-heterocyclyl and C$_{3-10}$-cycloalkyl is optionally substituted with one or mare substituents independently selected from hydroxy, sulfanyl, oxo, halogen, amino, sulfo, C$_{1-6}$-alkyl, C$_{2-6}$-alkenyl, aryl, heteroaryl, C$_{3-8}$-heterocyclyl and C$_{3-10}$-cycloalkyl, wherein each of hydroxy, sulfanyl, amino, sulfo, C$_{1-6}$-alkyl, C$_{2-6}$-alkenyl, aryl, heteroaryl, C$_{3-8}$-heterocyclyl and C$_{3-10}$-cycloalkyl is optionally substituted with one or more substituents independently selected from hydroxy, sulfanyl, oxo, halogen, amino, sulfo, C$_{2-6}$-alkenyl, aryl, heteroaryl, C$_{3-8}$-heterocyclyl and C$_{3-10}$-cycloalkyl, wherein each of hydroxy, sulfanyl, sulfo, C$_{1-6}$-alkyl, C$_{1-6}$-alkoxy, C$_{2-6}$-alkenyl, aryl, heteroaryl, C$_{3-8}$-heterocyclyl and C$_{3-10}$-cycloalkyl may optionally be substituted with one or more substituents independently selected from hydroxy, sulfanyl, oxo, halogen, amino, sulfo, perhalomethyl, perhalomethoxy, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl;
R$^6$ is hydrogen or fluor;
A is selected from —O—, —S—, —S(=O)—, —S(=O)$_2$—, —CH$_2$O—, —CH$_2$S—, —CH$_2$CH$_2$—N(R$^8$)—, —CH$_2$CHF—N(R$^8$)—, —CH$_2$CF$_2$—N(R$^8$)—, and —CHFCH$_2$—N(R$^8$)—;
R$^8$ is selected from hydrogen, C$_{1-6}$-alkyl, C$_{2-6}$-alkenyl, aryl, heteroaryl, C$_{3-8}$-heterocyclyl and C$_{3-10}$-cycloalkyl, wherein each of C$_{1-6}$-alkyl, C$_{2-6}$-alkenyl, aryl, heteroaryl, C$_{3-8}$-heterocyclyl and C$_{3-10}$-cycloalkyl is optionally substituted with one or more substituents independently selected from hydroxy, sulfanyl, oxo, halogen, amino, sulfo, C$_{1-6}$-alkyl, C$_{2-6}$-alkenyl, aryl, heteroaryl, C$_{3-8}$heterocyclyl and C$_{3-10}$-cycloalkyl, wherein each of hydroxy, sulfanyl, amino, sulfo, C$_{1-6}$-alkyl, C$_{2-6}$-alkenyl, aryl, heteroaryl, C$_{3-8}$-heterocyclyl and C$_{3-10}$-cycloalkyl is optionally substituted with one or more substituents independently selected from hydroxy, sulfanyl, oxo, halogen, amino, C$_{1-6}$-alkyl, perhalomethyl and perhalomethoxy;
R$^7$ is selected from aryl or heteroaryl, which may optionally be substituted with one or more substituents selected from hydroxy, sulfanyl, halogen, amino, sulfo, C$_{1-6}$-alkyl, C$_{2-6}$-alkenyl, aryl, heteroaryl, C$_{3-8}$-heterocyclyl and C$_{3-10}$-cycloalkyl, wherein each of hydroxy, sulfanyl, amino, sulfo, C$_{1-6}$-alkyl, C$_{2-6}$-alkenyl, aryl, heteroaryl, C$_{3-8}$-heterocyclyl and C$_{3-10}$-cycloalkyl is optionally substituted with one or more substituents independently selected from hydroxy, sulfanyl, oxo, halogen, amino, sulfo, C$_{1-6}$-alkyl, C$_{2-6}$-alkenyl, aryl, heteroaryl, C$_{3-8}$-heterocyclyl and C$_{3-10}$-cycloalkyl, wherein each of hydroxy, sulfanyl, amino, sulfo, C$_{1-6}$-alkyl, C$_{2-6}$-alkenyl, aryl, heteroaryl, C$_{3-8}$-heterocyclyl and C$_{3-10}$-cycloalkyl is optionally substituted with one or more substituents independently selected from hydroxy, sulfanyl, oxo, halogen, amino, C$_{1-6}$-alkyl, perhalomethyl and perhalomethoxy;
See International Patent Publication WO 2004/111032.

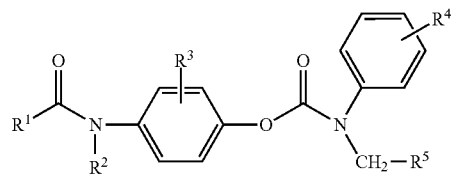

wherein
R$^1$ and R$^2$ are independently selected from hydrogen, hydroxy, sulfanyl, amino, halogen, sulk), C$_{1-6}$-alkyl, C$_{1-6}$-alkoxy, C$_{2-6}$-alkenyl, aryl, heteroaryl, C$_{3-10}$-heterocyclyl and C$_{3-10}$-cycloalkyl, wherein each of hydroxy, sulfanyl, sulfo, C$_{1-6}$-alkyl, C$_{1-6}$-alkoxy, C$_{2-6}$-alkenyl, aryl, heteroaryl, C$_{3-8}$-heterocyclyl and C$_{3-10}$-cycloalkyl may optionally be substituted with one or more substituents independently selected from hydroxy, sulfanyl, oxo, halogen, amino, sulfo, perhalomethyl, perhalomethoxy, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl;
R$^3$, R$^4$ and R$^3$ are independently selected from hydrogen, hydroxy, sulfanyl, fluor, amino, sulfo, C$_{2-6}$-alkenyl, aryl, heteroaryl, C$_{3-6}$-heterocyclyl and C$_{3-10}$-cycloalkyl, wherein each of hydroxy, sulfanyl, amino, sulfo, $C_{1-6}$-alkyl, $C_{2-6}$-alkenyl, aryl, heteroaryl, heterocyclyl and $C_{3-10}$-cycloalkyl is optionally substituted with one or more substituents independently selected from hydroxy, sulfanyl, oxo, halogen, amino, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, $C_{1-6}$-alkyl, perhalomethyl and perhalomethoxy;

See International Patent Publication WO 2004/111025.

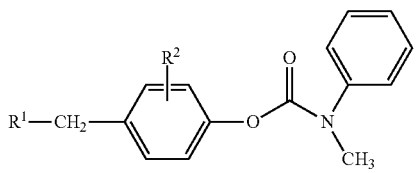

wherein
$R^1$ is selected from hydroxy, sulfanyl, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfanyl, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, sulfo, perhalomethyl, perhalomethoxy, $C_{1-6}$-alkyl, $C_{1-6}$alkoxy, $C_{2-6}$-alkenyl, aryl, heteroaryl, $C_{3-8}$-heterocyclyl, and $C_{3-10}$-cycloalkyl;

$R^2$ is selected from hydrogen, hydroxy, sulfanyl, amino, halogen, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-10}$-heterocyclyl and $C_{3-10}$-cycloalkyl may optionally be substituted with one or more substituents independently selected from hydroxy, sulfanyl, oxo, halogen, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, sulfo, perhalomethyl, perhalomethoxy, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl;

See International Patent Publication WO 2004/111006.

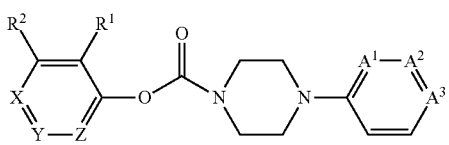

wherein
X is N or C—$R^3$, Y is N or C—$R^4$, Z is N or C—$R^5$;
$A^1$ is N or C—$R^6$, $A^2$ is N or C—$R^7$, $A^3$ is N or C—$R^8$;
provided that at least one of $A^1$, $A^2$ and $A^3$ is N;

$R^1$, $R^2$, $R^3$, $R^4$, $R^5$, $R^6$, $R^7$ and $R^8$ are independently selected from hydrogen, hydroxy, sulfanyl, halogen, amino, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, sulfo, $C_{1-6}$-alkyl, $C_{2-6}$-alkenyl, perhalomethyl and perhalomethoxy;

See International Patent Publication WO 2004/111007.

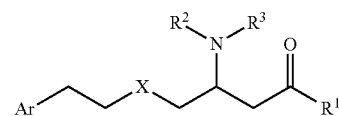

wherein:
Ar is an aryl or heteroaryl group;
X is —OC(O)—, —$NR^6$C(O)—, —$(CH_2)_m$—, —$O(CH_2)_m$, —$S(O)(CH_2)_m$, or —$S(O)O(CH_2)_m$, wherein m is 1 or 2;
$R^1$ is selected from the group consisting of hydrogen, OH, $C_{1-10}$alkyl, aryl, heteroaryl, $OC_{1-10}$heteroaryl, O-aryl, O-heteroaryl, $OC_{1-10}$alkylenylaryl, $OC_{1-10}$alkylenylheteroaryl, and N($R^4$)$R^5$;
$R^2$, $R^3$, $R^4$, $R^5$, and $R^6$ are each independently selected from the group consisting of hydrogen, $C_{1-10}$alkyl, $C(O)C_{1-10}$alkyl, $C(O)C(O)C_{1-10}$alkyl, $C(O)NR^7R^8$, and $C(O)C_{1-10}$haloalkyl; and
$R^7$ and $R^8$ are independently selected from the group consisting of hydrogen, $C_{1-10}$alkyl, aryl, and heteroaryl,
or a salt thereof.

In certain embodiments, the TPH1 inhibitor may be administered with one or more of the HSL inhibitors disclosed in International Patent Publication WO 2006/074957; International Patent Publication WO 2005/073199; International Patent Publication WO 2004/111031; International Patent Publication WO 2004/111004; International Patent Publication WO 2004/035550; International Patent Publication WO 2003/051841; International Patent Publication WO 2003/051842; or International Patent Publication WO 2001/066531.

In some embodiments, the efficacy of therapy to prevent or treat diabetes by administering TPH1 inhibitors is monitored by measuring blood glucose levels before and over time after treatment to determine the efficacy of the therapy.

The amount of therapeutic agents such as TPH1 inhibitors disclosed herein to be administered to a patient depends on many factors, as discussed herein. However, in humans, for example, the amount may range from about 1 mg/day to about 2 g/day; preferably from about 15 mg/day to about 500 mg/day; or from about 20 mg/day to about 250 mg/day; or from about 40 mg/day to about 100 mg/day. Other preferred dosages include about 2 mg/day, about 5 mg/day, about 10 mg/day, about 15 mg/day, about 20 mg/day, about 25 mg/day, about 30 mg/day, about 40 mg/day, about 50 mg/day, about 60 mg/day, about 70 mg/day, about 80 mg/day, about 90 mg/day, about 100 mg/day, about 125 mg/day, about 150 mg/day, about 175 mg/day, about 200 mg/day, about 250 mg/day, about 300 mg/day, about 350 mg/day, about 400 mg/day, about 500 mg/day, about 600 mg/day, about 700 mg/day, about 800 mg/day, and about 900 mg/day.

Other dose ranges that may be used include from about 50 mg/day to about 15 g/day; from about 50 mg/day to about 10 g/day; from about 50 mg/day to about 5 g/day; from about 50 mg/day to about 1 g/day; from about 50 mg/day to about 900 mg/day; from about 50 mg/day to about 800 mg/day; from about 50 mg/day to about 700 mg/day; from about 50 mg/day to about 600 mg/day; from about 50 mg/day to about 500 mg/day; from about 50 mg/day to about 400 mg/day; from about 50 mg/day to about 300 mg/day; or from about 50 mg/day to about 200 mg/day.

Other dose ranges that may be used include from about 100 mg/day to about 15 g/day; from about 100 mg/day to about 10 g/day; from about 100 mg/day to about 5 g/day; from about 100 mg/day to about 1 g/day; from about 100 mg/day to about 900 mg/day; from about 100 mg/day to about 800 mg/day; from about 100 mg/day to about 700 mg/day; from about 100 mg/day to about 600 mg/day; from about 100 mg/day to about 500 mg/day; from about 100 mg/day to about 400 mg/day; from about 100 mg/day to about 300 mg/day; or from about 100 mg/day to about 200 mg/day.

Other dose ranges that may be used include from about 200 mg/day to about 15 g/day; from about 200 mg/day to about 10 g/day; from about 200 mg/day to about 5 g/day; from about 200 mg/day to about 1 g/day; from about 200 mg/day to about 900 mg/day; from about 200 mg/day to about 800 mg/day; from about 200 mg/day to about 700 mg/day; from about 200 mg/day to about 600 mg/day; from about 200 mg/day to about 500 mg/day; from about 200 mg/day to about 400 mg/day; or from about 200 mg/day to about 300 mg/day.

Other dose ranges that may be used include from about 300 mg/day to about 15 g/day; from about 300 mg/day to about 10 g/day; from about 300 mg/day to about 5 g/day; from about 300 mg/day to about 1 g/day; from about 300 mg/day to about 900 mg/day; from about 300 mg/day to about 800 mg/day; from about 300 mg/day to about 700 mg/day; from about 300 mg/day to about 600 mg/day; from about 300 mg/day to about 500 mg/day; or from about 300 mg/day to about 400 mg/day.

Other dose ranges that may be used include from about 400 mg/day to about 15 g/day; from about 400 mg/day to about 10 g/day; from about 400 mg/day to about 5 g/day; from about 400 mg/day to about 1 g/day; from about 400 mg/day to about 900 mg/day; from about 400 mg/day to about 800 mg/day; from about 400 mg/day to about 700 mg/day; from about 400 mg/day to about 600 mg/day; or from about 400 mg/day to about 500 mg/day.

Other dose ranges that may be used include from about 500 mg/day to about 15 g/day; from about 500 mg/day to about 10 g/day; from about 500 mg/day to about 5 g/day; from about 500 mg/day to about 4 g/day; from about 500 mg/day to about 3 g/day; from about 500 mg/day to about 2 g/day; from about 500 mg/day to about 1 g/day; from about 500 mg/day to about 900 mg/day; from about 500 mg/day to about 800 mg/day; from about 500 mg/day to about 700 mg/day; or from about 500 mg/day to about 600 mg/day.

Other dose ranges that may be used include from about 600 mg/day to about 15 g/day; from about 600 mg/day to about 10 g/day; from about 600 mg/day to about 5 g/day; from about 600 mg/day to about 4 g/day; from about 600 mg/day to about 3 g/day; from about 600 mg/day to about 2 g/day; from about 600 mg/day to about 1 g/day; from about 600 mg/day to about 900 mg/day; from about 600 mg/day to about 800 mg/day; or from about 600 mg/day to about 700 mg/day.

Other dose ranges that may be used include from about 700 mg/day to about 15 g/day; from about 700 mg/day to about 10 g/day; from about 700 mg/day to about 5 g/day; from about 700 mg/day to about 4 g/day; from about 700 mg/day to about 3 g/day; from about 700 mg/day to about 2 g/day; from about 700 mg/day to about 1 g/day; from about 700 mg/day to about 900 mg/day; or from about 700 mg/day to about 800 mg/day.

Other dose ranges that may be used include from about 800 mg/day to about 15 g/day; from about 800 mg/day to about 10 g/day; from about 800 mg/day to about 5 g/day; from about 800 mg/day to about 4 g/day; from about 800 mg/day to about 3 g/day; from about 800 mg/day to about 2 g/day; from about 800 mg/day to about 1 g/day; or from about 800 mg/day to about 900 mg/day.

Other dose ranges that may be used include from about 900 mg/day to about 15 g/day; from about 900 mg/day to about 10 g/day; from about 900 mg/day to about 5 g/day; from about 900 mg/day to about 4 g/day; from about 900 mg/day to about 3 g/day; from about 900 mg/day to about 2 g/day; or from about 900 mg/day to about 1 g/day.

Other dose ranges that may be used include from about 1 g/day to about 15 g/day; from about 1 g/day to about 10 g/day; from about 1 g/day to about 5 g/day; from about 1 g/day to about 4 g/day; from about 1 g/day to about 3 g/day; or from about 1 g/day to about 2 g/day.

Other dosages that may be used include from about 1 g/day, about 2 g/day, about 3 g/day, about 4 g/day, about 5 g/day, about 6 g/day, about 7 g/day, about 8 g/day, about 9 g/day, about 10 g/day, about 11 g/day, about 12 g/day, about 13 g/day, about 14 g/day, or about 15 g/day.

The amount of therapeutic agent disclosed herein to be administered to a patient may range from about 5 mg/kg/day to about 500 mg/kg/day, from about 5 mg/kg/day to about 400 mg/kg/day, from about 5 mg/kg/day to about 300 mg/kg/day, from about 5 mg/kg/day to about 250 mg/kg/day, from about 5 mg/kg/day to about 200 mg/kg/day, from about 5 mg/kg/day to about 150 mg/kg/day, from about 5 mg/kg/day to about 100 mg/kg/day, from about 5 mg/kg/day to about 75 mg/kg/day, from about 5 mg/kg/day to about 50 mg/kg/day, from about 5 mg/kg/day to about 40 mg/kg/day, from about 5 mg/kg/day to about 35 mg/kg/day, from about 5 mg/kg/day to about 30 mg/kg/day, from about 5 mg/kg/day to about 25 mg/kg/day, from about 5 mg/kg/day to about 24 mg/kg/day, from about 5 mg/kg/day to about 23 mg/kg/day, from about 5 mg/kg/day to about 22 mg/kg/day, from about 5 mg/kg/day to about 21 mg/kg/day, from about 5 mg/kg/day to about 20 mg/kg/day, from about 5 mg/kg/day to about 19 mg/kg/day, from about 5 mg/kg/day to about 18 mg/kg/day, from about 5 mg/kg/day to about 17 mg/kg/day, from about 5 mg/kg/day to about 16 mg/kg/day, from about 5 mg/kg/day to about 15 mg/kg/day, from about 5 mg/kg/day to about 14 mg/kg/day, from about 5 mg/kg/day to about 13 mg/kg/day, from about 5 mg/kg/day to about 12 mg/kg/day, from about 5 mg/kg/day to about 11 mg/kg/day, or from about 5 mg/kg/day to about 10 mg/kg/day.

Other dose ranges that may be used include from about 10 mg/kg/day to about 500 mg/kg/day, from about 10 mg/kg/day to about 400 mg/kg/day, from about 10 mg/kg/day to about 300 mg/kg/day, from about 10 mg/kg/day to about 250 mg/kg/day, from about 10 mg/kg/day to about 200 mg/kg/day, from about 10 mg/kg/day to about 150 mg/kg/day, from about 10 mg/kg/day to about 100 mg/kg/day, from about 10 mg/kg/day to about 75 mg/kg/day, from about 10 mg/kg/day to about 50 mg/kg/day, from about 10 mg/kg/day to about 45 mg/kg/day, from about 10 mg/kg/day to about 40 mg/kg/day, from about 10 mg/kg/day to about 35 mg/kg/day, from about 10 mg/kg/day to about 34 mg/kg/day, from about 10 mg/kg/day to about 33 mg/kg/day, from about 10 mg/kg/day to about 32 mg/kg/day, from about 10 mg/kg/day to about 31 mg/kg/day, from about 10 mg/kg/day to about 30 mg/kg/day, from about 10 mg/kg/day to about 29 mg/kg/day, from about 10 mg/kg/day to about 28 mg/kg/day, from about 10 mg/kg/day to about 27 mg/kg/day, from about 10 mg/kg/day to about 26 mg/kg/day, from about 10 mg/kg/day to about 25 mg/kg/day, from about 10 mg/kg/day to about 24 mg/kg/day, from about 10 mg/kg/day to about 23 mg/kg/day, from about 10 mg/kg/day to about 22 mg/kg/day, from about 10 mg/kg/day to about 21 mg/kg/day, from about 10 mg/kg/day to about 20 mg/kg/day, from about 10 mg/kg/day to about 19 mg/kg/day, from about 10 mg/kg/day to about 18 mg/kg/day, from about 10 mg/kg/day to about 17 mg/kg/day, from about 10 mg/kg/day to about 16 mg/kg/day, or from about 10 mg/kg/day to about 15 mg/kg/day.

Other dose ranges that may be used include from about 15 mg/kg/day to about 500 mg/kg/day, from about 15 mg/kg/day to about 400 mg/kg/day, from about 15 mg/kg/day to about 300 mg/kg/day, from about 15 mg/kg/day to about 250 mg/kg/day, from about 15 mg/kg/day to about 200 mg/kg/day, from about 15 mg/kg/day to about 150 mg/kg/day, from about 15 mg/kg/day to about 100 mg/kg/day, from about 15 mg/kg/day to about 75 mg/kg/day, from about 15 mg/kg/day to about 50 mg/kg/day, from about 15 mg/kg/day to about 40 mg/kg/day, from about 15 mg/kg/day to about 30 mg/kg/day, from about 15 mg/kg/day to about 25 mg/kg/day, or from about 15 mg/kg/day to about 20 mg/kg/day.

Other dose ranges that may be used include from about 20 mg/kg/day to about 500 mg/kg/day, from about 20 mg/kg/day to about 400 mg/kg/day, from about 20 mg/kg/day to about 300 mg/kg/day, from about 20 mg/kg/day to about 250 mg/kg/day, from about 20 mg/kg/day to about 200 mg/kg/day, from about 20 mg/kg/day to about 150 mg/kg/day, from about 20 mg/kg/day to about 100 mg/kg/day, from about 20 mg/kg/day to about 75 mg/kg/day, from about 20 mg/kg/day to about 50 mg/kg/day, from about 20 mg/kg/day to about 40 mg/kg/day, from about 20 mg/kg/day to about 30 mg/kg/day, or from about 20 mg/kg/day to about 25 mg/kg/day.

Other dose ranges that may be used include from about 25 mg/kg/day to about 500 mg/kg/day, from about 25 mg/kg/day to about 400 mg/kg/day, from about 25 mg/kg/day to about 300 mg/kg/day, from about 25 mg/kg/day to about 250 mg/kg/day, from about 25 mg/kg/day to about 200 mg/kg/day, from about 25 mg/kg/day to about 150 mg/kg/day, from about 25 mg/kg/day to about 100 mg/kg/day, from about 25 mg/kg/day to about 75 mg/kg/day, from about 25 mg/kg/day to about 50 mg/kg/day, from about 25 mg/kg/day to about 40 mg/kg/day, or from about 25 mg/kg/day to about 30 mg/kg/day.

Other dose ranges that may be used include from about 30 mg/kg/day to about 500 mg/kg/day, from about 30 mg/kg/day to about 400 mg/kg/day, from about 30 mg/kg/day to about 300 mg/kg/day, from about 30 mg/kg/day to about 250 mg/kg/day, from about 30 mg/kg/day to about 200 mg/kg/day, from about 30 mg/kg/day to about 150 mg/kg/day, from about 30 mg/kg/day to about 100 mg/kg/day, from about 30 mg/kg/day to about 75 mg/kg/day, from about 30 mg/kg/day to about 50 mg/kg/day, or from about 30 mg/kg/day to about 40 mg/kg/day.

Other dose ranges that may be used include from about 40 mg/kg/day to about 500 mg/kg/day, from about 40 mg/kg/day to about 400 mg/kg/day, from about 40 mg/kg/day to about 300 mg/kg/day, from about 40 mg/kg/day to about 250 mg/kg/day, from about 40 mg/kg/day to about 200 mg/kg/day, from about 40 mg/kg/day to about 150 mg/kg/day, from about 40 mg/kg/day to about 100 mg/kg/day, from about 40 mg/kg/day to about 75 mg/kg/day, from about 40 mg/kg/day to about 60 mg/kg/day, or from about 40 mg/kg/day to about 50 mg/kg/day.

Other dose ranges that may be used include from about 50 mg/kg/day to about 500 mg/kg/day, from about 50 mg/kg/day to about 400 mg/kg/day, from about 50 mg/kg/day to about 300 mg/kg/day, from about 50 mg/kg/day to about 250 mg/kg/day, from about 50 mg/kg/day to about 200 mg/kg/day, from about 50 mg/kg/day to about 175 mg/kg/day, from about 50 mg/kg/day to about 150 mg/kg/day, from about 50 mg/kg/day to about 125 mg/kg/day, from about 50 mg/kg/day to about 100 mg/kg/day, from about 50 mg/kg/day to about 75 mg/kg/day, or from about 50 mg/kg/day to about 60 mg/kg/day.

Other dose ranges that may be used include from about 60 mg/kg/day to about 500 mg/kg/day, from about 60 mg/kg/day to about 400 mg/kg/day, from about 60 mg/kg/day to about 300 mg/kg/day, from about 60 mg/kg/day to about 250 mg/kg/day, from about 60 mg/kg/day to about 200 mg/kg/day, from about 60 mg/kg/day to about 175 mg/kg/day, from about 60 mg/kg/day to about 150 mg/kg/day, from about 60 mg/kg/day to about 125 mg/kg/day, from about 60 mg/kg/day to about 100 mg/kg/day, or from about 60 mg/kg/day to about 75 mg/kg/day.

Other dose ranges that may be used include from about 70 mg/kg/day to about 500 mg/kg/day, from about 70 mg/kg/day to about 400 mg/kg/day, from about 70 mg/kg/day to about 300 mg/kg/day, from about 70 mg/kg/day to about 250 mg/kg/day, from about 70 mg/kg/day to about 200 mg/kg/day, from about 70 mg/kg/day to about 175 mg/kg/day, from about 70 mg/kg/day to about 150 mg/kg/day, from about 70 mg/kg/day to about 125 mg/kg/day, or from about 70 mg/kg/day to about 100 mg/kg/day.

Other dose ranges that may be used include from about 80 mg/kg/day to about 500 mg/kg/day, from about 80 mg/kg/day to about 400 mg/kg/day, from about 80 mg/kg/day to about 300 mg/kg/day, from about 80 mg/kg/day to about 250 mg/kg/day, from about 80 mg/kg/day to about 200 mg/kg/day, from about 80 mg/kg/day to about 175 mg/kg/day, from about 80 mg/kg/day to about 150 mg/kg/day, from about 80 mg/kg/day to about 125 mg/kg/day, or from about 80 mg/kg/day to about 100 mg/kg/day.

Other dose ranges that may be used include from about 90 mg/kg/day to about 500 mg/kg/day, from about 90 mg/kg/day to about 400 mg/kg/day, from about 90 mg/kg/day to about 300 mg/kg/day, from about 90 mg/kg/day to about 250 mg/kg/day, from about 90 mg/kg/day to about 200 mg/kg/day, from about 90 mg/kg/day to about 175 mg/kg/day, from about 90 mg/kg/day to about 150 mg/kg/day, from about 90 mg/kg/day to about 125 mg/kg/day, or from about 90 mg/kg/day to about 100 mg/kg/day.

Other dose ranges that may be used include from about 100 mg/kg/day to about 500 mg/kg/day, from about 100 mg/kg/day to about 400 mg/kg/day, from about 100 mg/kg/day to about 300 mg/kg/day, from about 100 mg/kg/day to about 250 mg/kg/day, from about 100 mg/kg/day to about 200 mg/kg/day, from about 100 mg/kg/day to about 175 mg/kg/day, from about 100 mg/kg/day to about 150 mg/kg/day, or from about 100 mg/kg/day to about 125 mg/kg/day.

Other dosages that may be used include about 5 mg/kg/day, about 6 mg/kg/day, about 7 mg/kg/day, about 8 mg/kg/day, about 9 mg/kg/day, about 10 mg/kg/day, about 11 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, about 25 mg/kg/day, about 26 mg/kg/day, about 27 mg/kg/day, about 28 mg/kg/day, about 29 mg/kg/day, about 30 mg/kg/day, about 31 mg/kg/day, about 32 mg/kg/day, about 33 mg/kg/day, about 34 mg/kg/day, about 35 mg/kg/day, about 36 mg/kg/day, about 37 mg/kg/day, about 38 mg/kg/day, about 39 mg/kg/day, about 40 mg/kg/day, about 45 mg/kg/day, about 50 mg/kg/day, about 60 mg/kg/day, about 70 mg/kg/day, about 80 mg/kg/day, about 90 mg/kg/day, about 100 mg/kg/day, about 125 mg/kg/day, about 150 mg/kg/day, about 175 mg/kg/day, about 200 mg/kg/day, about 250 mg/kg/day, or about 350 mg/kg/day.

The amounts and dosages of therapeutic agents disclosed above may be administered in the form of a once-per day pharmaceutical composition. Thus, e.g., the disclosure of 50 mg/day is to be taken as including the disclosure of a pharmaceutical composition comprising a therapeutic agent as disclosed herein where the pharmaceutical composition comprises 50 mg of the therapeutic agent.

Routine experimentation will determine the appropriate dosage for each patient and each therapeutic agent by monitoring the therapeutic agent's effect on serum or plasma serotonin levels, which can be frequently and easily monitored. The therapeutic agent can be administered once or multiple times per day. Serum or plasma serotonin levels can be monitored before and during therapy to determine the appropriate amount of therapeutic agent to administer to lower serum or plasma serotonin levels or bring serum or plasma serotonin levels to normal and to maintain normal levels over extended periods of time. The frequency of administration may vary from a single dose per day to multiple doses per day. Preferred routes of administration include oral, intravenous and intraperitoneal, but other forms of administration may be chosen as well.

In certain embodiments, the therapeutic agents of the invention act selectively on peripheral serotonin or are administered in an amount that decreases serum or plasma serotonin without increasing or decreasing brain-derived serotonin.

Monitoring the therapeutic efficacy of TPH1 inhibitors is straightforward, as one can administer the TPH1 inhibitors in an amount and for a duration that reduces serum or plasma serotonin levels, and over time decreases blood glucose levels. Serum or plasma serotonin levels and blood glucose levels can be easily measured. Monitoring serum or plasma serotonin is simple and can be done frequently during the course of therapy to establish the appropriate dose for each patient. Any method known in the art for assaying serum or plasma serotonin can be used. Measuring blood glucose levels may also be done by methods known in the art.

In certain embodiments, the methods of the present invention comprise the step of identifying a patient in need of therapy for diabetes. Thus, the present invention provides a method comprising:

(a) identifying a patient in need of therapy for diabetes;

(b) administering to the patient a therapeutically effective amount of a therapeutic agent that decreases serum or plasma serotonin levels in order to prevent or treat diabetes in the patient identified in step (a).

In certain embodiments, "identifying" in step (a) above may be done by measuring the patient's level of blood, serum, or plasma serotonin, e.g., by forming a detectable complex of blood, serum, or plasma serotonin and a reagent that binds to blood, serum, or plasma serotonin in order to determine the patient's level of blood, serum, or plasma serotonin, where an elevated level of blood, serum, or plasma serotonin identifies the patient as being in need of therapy for diabetes. In certain embodiments, the reagent is an antibody or antibody fragment that binds to serotonin. In certain embodiments, the antibody or antibody fragment that binds to serotonin is labeled (e.g., radioactively, antigenically, fluorescently, with peroxidase, etc.) and measuring the patient's level of blood, serum, or plasma serotonin includes the step of detecting a physical transformation in the label (e.g., radioactive decay of the label) or in a substance acted upon by the label (oxidation of a substrate by a peroxidase label).

In certain embodiments, "identifying" in step (a) above includes transforming serotonin from a bodily sample from the patient into a derivative of serotonin, e.g., N-acylserotonin. In certain embodiments, "identifying" in step (a) above includes subjecting serotonin or a serotonin derivative from a bodily sample from the patient to chromatography where the serotonin is separated from the components of the blood with which it is normally found and interacts with the stationary phase used in the chromatographic process.

In certain embodiments, the patient's level of blood, serum, or plasma serotonin is determined to be elevated in comparison to a standard level of blood, serum, or plasma serotonin that has previously been determined to be a normal level. In other embodiments, the patient's level of blood, serum, or plasma serotonin is determined to be elevated in comparison to a level of blood, serum, or plasma serotonin measured in a person who is known not to be in need of therapy for diabetes. In other embodiments, the patient's level of blood, serum, or plasma serotonin is determined to be elevated in comparison to a level of blood, serum, or plasma serotonin measured in the patient at a time when the patient was known not to be in need of therapy for diabetes.

In certain embodiments, "a patient in need of therapy for diabetes" is a patient with an elevated blood glucose level, "identifying" in step (a) above may be done by measuring the patient's blood glucose level, e.g., by forming a detectable complex of glucose obtained from the blood of the patient and a reagent that binds to glucose in order to determine the patient's blood glucose level, where an elevated blood glucose level identifies the patient as being in need of therapy for diabetes. In certain embodiments, the reagent is labeled (e.g., radioactively, antigenically, fluorescently, with peroxidase etc.) and measuring the patient's blood glucose level includes the step of detecting a physical transformation in the label (e.g., radioactive decay of the label) or in a substance acted upon by the label (oxidation of a substrate by a peroxidase label to transform the substrate into a different substance).

In certain embodiments, "identifying" in step (a) above includes transforming glucose from a bodily sample from the patient into a derivative of glucose, e.g., by contacting glucose from the patient's blood with glucose oxidase, thereby oxidizing the glucose. In certain embodiments, "identifying" in step (a) above includes subjecting glucose or a glucose derivative from a bodily sample from the patient to chromatography where the glucose is separated from the components of the blood with which it is normally found and interacts with the stationary phase used in the chromatographic process.

In certain embodiments, the patient's level of blood glucose is determined to be elevated in comparison to a standard level of blood glucose that has previously been determined to be a normal level. In other embodiments, the patient's level of blood glucose is determined to be elevated in comparison to a level of blood glucose measured in a person who is known not to be in need of therapy for diabetes. In other embodiments, the patient's level of blood glucose is determined to be elevated in comparison to a level of blood glucose measured in the patient at a time when the patient was known not to be in need of therapy for diabetes.

The present invention encompasses a TPH1 inhibitor for use in the prevention or treatment of diabetes in a patient in need of such prevention or treatment. The patient is preferably a mammal, e.g., a human. The TPH1 inhibitor may be a therapeutic agent selected from therapeutic agents (1)-(189) disclosed herein or the therapeutic agents listed in Table 1. In certain embodiments, the diabetes is Type II diabetes. In other embodiments, the diabetes is Type I diabetes.

The present invention encompasses the use a TPH1 inhibitor for the manufacture of a medicament for preventing or treating diabetes. In certain embodiments, the present invention encompasses the use of a therapeutic agent selected from therapeutic agents (1)-(189) disclosed herein or the therapeutic agents listed in Table 1 for the manufacture of a medicament for preventing or treating diabetes. In certain embodiments, the diabetes is Type II diabetes. In other embodiments, the diabetes is Type I diabetes.

Pharmaceutical Compositions

Therapeutic agents such as the TPH1 inhibitors described herein may be formulated into pharmaceutical compositions. The pharmaceutical compositions may be solids or liquids. The therapeutic agents may be present in the pharmaceutical compositions in the form of salts of pharmaceutically acceptable acids or in the form of bases. The therapeutic agents may be present in amorphous form or in crystalline forms, including hydrates and solvates. Preferably, the pharmaceutical compositions comprise a therapeutically effective amount of a TPH1 inhibitor.

Pharmaceutically acceptable derivatives of any of the TPH1 inhibitors described herein are within the scope of the invention. A "pharmaceutically acceptable derivative" of a TPH1 inhibitor means any non-toxic derivative of a TPH1 inhibitor described herein that, upon administration to a patient, exhibits the same or similar activity with respect to reducing blood, serum, or plasma serotonin levels as the TPH1 inhibitor described herein.

Pharmaceutically acceptable salts of the therapeutic agents described herein for use in treating or preventing diabetes include those salts derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate salts. Other acids, such as oxalic, while not in themselves pharmaceutically acceptable, may be employed in the preparation of salts useful as intermediates in obtaining the therapeutic agents of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. The present invention also envisions the quaternization of any basic nitrogen-containing groups of the therapeutic agents disclosed herein. Water or oil-soluble or dispersible products may be obtained by such quaternization.

The therapeutic agents disclosed herein are also meant to include all stereochemical forms of the therapeutic agents (i.e., the R and S configurations for each asymmetric center). Therefore, the use of single enantiomers, racemic mixtures, and diastereomers of the therapeutic agents is within the scope of the invention. Also within the scope of the invention is the use of steric isomers and positional isomers of the therapeutic agents. The therapeutic agents of the present invention are also meant to include compounds which differ only in the presence of one or more isotopically enriched atoms. For example, therapeutic agents in which one or more hydrogens are replaced by deuterium or tritium, or the replacement of one or more carbons by $^{13}$C- or $^{14}$C-enriched carbon, are within the scope of this invention.

In a particular embodiment, the therapeutic agents of the present invention are administered in a pharmaceutical composition that includes a pharmaceutically acceptable carrier, adjuvant, or vehicle. The term "pharmaceutically acceptable carrier, adjuvant, or vehicle" refers to a non-toxic carrier, adjuvant, or vehicle that does not destroy or significantly diminish the pharmacological activity of the therapeutic agent with which it is formulated. Pharmaceutically acceptable carriers, adjuvants or vehicles that may be used in the pharmaceutical compositions of this invention encompass any of the standard pharmaceutically accepted solid carriers as well as liquid carriers such as a phosphate-buffered saline solution, water, as well as emulsions such as an oil/water emulsion or a triglyceride emulsion. An example of an acceptable triglyceride emulsion useful in the intravenous and intraperitoneal administration of the compounds is the triglyceride emulsion commercially known as INTRALIPID®. Solid carriers may include excipients such as starch, milk, sugar, certain types of clay, stearic acid, talc, gums, glycols, or other known excipients. Carriers may also include flavor and color additives or other ingredients.

The pharmaceutical compositions of the present invention are preferably administered orally. However, the pharmaceutical compositions may be administered parenterally, by inhalation spray, topically, rectally, nasally, buccally, vaginally or via an implanted reservoir. Preferably, the pharmaceutical compositions are administered orally, intraperitoneally or intravenously. Sterile injectable forms of the pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solutions. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, solid forms such as capsules and tablets. In the case of tablets for oral use, carriers commonly used include microcrystalline cellulose, lactose and corn starch. Lubricating agents, such as magnesium stearate, are also typically added. When aqueous suspensions are required for oral use, the active ingredient may be combined with emulsifying and suspending agents. If desired, certain sweetening, flavoring or coloring agents may also be added.

The pharmaceutical compositions of this invention may also be administered by nasal aerosol or inhalation. Such pharmaceutical compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Should topical administration be desired, it can be accomplished using any method commonly known to those skilled in the art and includes but is not limited to incorporation of the pharmaceutical composition into creams, ointments, or transdermal patches.

The pharmaceutical compositions may contain derivatives of the TPH1 inhibitors. For example, the TPH1 inhibitors of the present invention can be derivatized by the formation of a reversible linkage with one or more suitable groups to yield "pro-drugs," i.e., chemical derivatives that, after absorption by the host, are converted into the parent compound. Liberation of the parent compound may be by chemical hydrolysis or enzymatic attack. A derivative or pro-drug can have enhanced permeability for the target organ. In the case of TPH1 inhibitors, the target organ is the duodenum where 95% of peripheral serotonin is made. The prodrug has an enhanced permeability according to the present invention if, after administration of the pro-drug or derivative thereof to a living organism, a higher amount of the compound reaches the target organ, resulting in a higher level of effective therapeutic agent, as compared to administration of the base compound without derivatization.

The amount of the therapeutic agents of the present invention that may be combined with the carrier materials to produce a pharmaceutical composition in a single dosage form may vary depending upon the patient being treated and the particular mode of administration. It should be understood that a specific dosage and treatment regimen for any particular patient will depend upon a variety of factors, including the activity of the specific therapeutic agent employed, the age, body weight, general health, sex, diet, time of administration, rate of excretion, drug combination, and the judgment of the treating physician, as well as the severity of the particular condition being treated. Despite their variety, accounting for these factors in order to select an appropriate dosage or treatment regimen is routinely done in the art and thus would require no more than routine experimentation.

The dosage of TPH1 inhibitor administered may also depend on whether the TPH1 inhibitor is being administered for the prevention or for the treatment of diabetes. For prevention, preferred dose ranges include from about 5 mg/kg/day to about 250 mg/kg/day; from about 5 mg/kg/day to about 100 mg/kg/day; or from about 5 mg/kg/day to about 30 mg/kg/day; with about 10 mg/kg/day being especially preferred.

For treatment, preferred dose ranges include from about 10 mg/kg/day to about 250 mg/kg/day; from about 10 mg/kg/day to about 50 mg/kg/day; or from about 10 mg/kg/day to about 30 mg/kg/day; with about 25 mg/kg/day being especially preferred.

Additional drugs which are normally administered to treat diabetes may also be administered with the therapeutic agents of this invention. Those additional drugs may be administered separately from the therapeutic agents that are used to lower blood, serum, or plasma serotonin levels, as part of a multiple drug dosage regimen. Alternatively, those additional drugs may be part of a single dosage form, mixed together or otherwise combined with the therapeutic agents that are used to lower blood, serum, or plasma serotonin levels in a single pharmaceutical composition. If administered as part of a multiple drug dosage regime, the additional drugs and the therapeutic agents used to lower blood, serum, or plasma serotonin levels may be administered simultaneously, sequentially or within a selected specified period of time from one another. The amount of both the therapeutic agent that is used to lower blood, serum, or plasma serotonin levels and the additional drug (in those compositions which comprise an additional drug) that may be combined with the carrier materials to produce a single dosage form will vary depending upon the patient treated and the particular mode of administration as well as on the nature of the therapeutic agent that is used to lower blood, serum, or plasma serotonin levels and the nature of the additional drug.

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

EXAMPLES

Example 1

Materials & Methods

Animal Experiments

Mice were housed under 12:12 light:dark cycle and chow and water were provided ad libitum. All animals were maintained according to NIH guidelines. The Htr2bflox/flox, Tph1flox/flox, and Villin-cre mice have been described previously (1). Alb-cre and aP2-cre mice were obtained from the Jackson Laboratory. For glucose tolerance tests mice were fasted overnight before i.p. injection of 2 g/kg body weight (BW) d-glucose in phosphate buffered saline (PBS) or 1 g/kg BW when mice were fed high fat diet. For pyruvate tolerance tests, mice were fasted overnight, injected i.p. with 2 g/kg BW sodium pyruvate in PBS. Glycerol tolerance test (4 g/kg BW) was performed after 4 h fasting. For insulin tolerance tests, mice were injected with 0.75 U/kg of insulin after 4 h fasting. Glucose was measured by tail vein bleeds at the indicated intervals using an ACCU-CHECK® glucometer. Measurement of free fatty acids (FFA) and glycerol were performed in plasma using a serum triglycerides determination kit (TR0100, Sigma) and a NEFA-HR(2) kit (WAKO Diagnostics). Plasma concentration of serotonin and glucagon were determined by Glucagon ELISA (Alpco, 48-GLUHU-E01) and Serotonin (Research) ELISA, (IBL-America, IB89540). Hyperinsulinemic-euglycemic clamp was performed in the University of Massachusetts Mouse Phenotyping Center, University of Massachusetts Medical School. LP533401 was purchased from Dalton Pharma Services (Toronto, Ontario, Canada), dissolved in polyethylene glycol 400 and supplemented with 2.5% glucose, and administered daily at the dose of 100 mg/kg by gavage.

Histology

Histological analyses were performed on paraffin embedded epididymal fat. 5 μm thick sections were stained with hematoxylin-eosin and analyzed using a 20× objective. Quantification of the size of individual adipocytes was performed using ImageJ.

Enzymatic Activity Assays fructose-1,6-bisphosphatase (FBPase) and glucose-6-phosphatase (G6Pase) enzymatic activities assays were performed as described previously (2-3). All reagents were obtained from Sigma.

In Vitro Lipolysis of Isolated Fat Pads

In vitro lipolysis assay was performed as described (4). Briefly, epididymal fat pads were isolated and washed several times in Hank's Balanced Salt Solution (HBSS) (Sigma). Tissue pieces (~25 mg) were incubated in Dulbecco's Modified Eagle's Medium (DMEM) medium (Invitrogen) containing 2% fatty acid free bovine serum albumin (Sigma) at 37° C. for 1 h. After this preincubation, the fat explants were transferred into identical, fresh medium containing serotonin (Sigma) or 10 μM forskolin as a positive control and incubated further for the indicated time-points at 37° C. Afterwards, aliquots of medium were taken for measurements of FFAs and glycerol using available kits (NEFA-HR(2), WAKO Diagnostics; serum triglycerides determination kit, TR0100, Sigma) and tissue was lysed with RIPA buffer for subsequent Western blot analysis or in TRIZOL® (Invitrogen) for gene expression analysis.

In Vitro Glucose Production

Production of glucose was assessed in primary, freshly isolated, attached hepatocytes. Briefly, cells were platted on 12 well plate format (200,000 cells per well). After isolation, the cells were allowed to attach and recover for 6 h in Williams E medium containing 10% fetal calf serum. Then they were washed and starved for 1 h in Dulbecco's Modified Eagle's DMEM without glucose and phenol red but with 2 mM L-glutamate and 0.5% BSA (D5030, Sigma). Then the cells were switched to the same medium or the same medium containing 10 mM glycerol and stimulated with the indicated substances for 6 h. Glucose concentration was determined in the medium using Amplex Red Glucose/Glucose Oxidase Assay Kit, (Invitrogen, A22189). Glucose production from glycerol was determined by subtracting glucose produced by the cells incubated without glycerol from this incubated with glycerol.

Western Blotting

Western blotting was performed according to standard procedures. Frozen tissues or cells were homogenized and lysed with RIPA buffer. Membranes were blocked and then incubated overnight with primary antibody in TBST-5% BSA, followed by incubation with appropriate HRP-conjugated secondary antibody. Signals were visualized with ECL. The following primary antibodies were used: antiphospho-HSL (s563) (4139), antiphospho-HSL(s565) (4137), antiphospho-HSL(s660) (4126) and anti-perilipin (3470) (all from Cell Signaling); anti-HSL (ab45422), anti-ATGL (ab85348) and anti-glycerol kinase (ab70029) (all from Abcam); anti-β-actin (A5441) and anti-α-tubulin (T6199) (all from Sigma); anti-G6Pase (Aviva Systems Biology, ARP44224_P050); anti-FBPase (Abgent, AP7385c); antiphospho-perilipin (s522) (Vala Sciences, 4856).

RNA Isolation and Real-Time PCR Analysis

Total RNA was isolated using TRIZOL® reagent with manufacturer's protocol (Invitrogen) and 2 μg of total RNA was used to synthesize complementary DNA using random primers and M-MLV reverse transcriptase (Invitrogen). For quantitative PCR, FastStart SYBR Green Master (Roche) was used in an MX3000P Real-Time System thermocycler (Stratagene). Primers sequence available upon request. qPCR values were normalized against β-actin or GAPDH expression. Primer sequences are available upon request.

Statistical Analysis

Data are always shown as mean values±s.e.m. Analyses of significant differences between means were performed using two-tailed Student's t-tests in case of comparison of 2 groups or analysis of variance followed by Tukey's post-hoc test, in case of multiple groups. n, number of independent cultures or animals used. In all cases *P<0.05; P<0.01; *P<0.001.

REFERENCES FOR EXAMPLE 1, MATERIALS AND METHODS

1. V. K. Yadav et al., *Cell* 135, 825 (Nov. 28, 2008).
2. A. Reyes, M. E. Burgos, E. Hubert, J. C. Slebe, *J Biol Chem* 262, 8451 (Jun. 25, 1987).
3. M. Alegre, C. J. Ciudad, C. Fillat, J. J. Guinovart, *Anal Biochem* 173, 185 (Aug. 15, 1988).
4. M. Schweiger et al., *J Biol Chem* 281, 40236 (Dec. 29, 2006).

Example 2

Fasting Increases Plasma Serotonin Levels

Figure 1I:
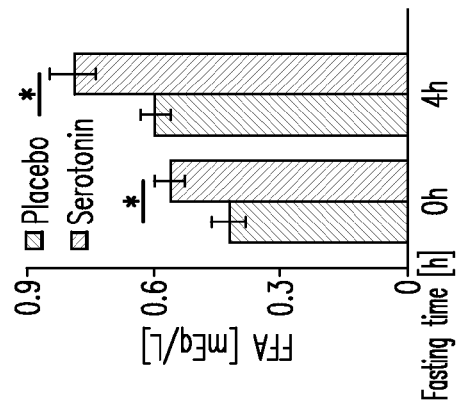
FIG. 1. GDS is required for fasting induced lipolysis. (A) Relative expression of Tph1 in duodenum from mice fasted for indicated time (n≥5). (B) Relative increase in plasma levels of serotonin (5-HT) and glucagon in mice fasted for indicated time (n≥5). Plasma levels of (C) glycerol and (D) FFA in mice of indicated genotypes fasted for indicated time (n≥7). (E) Epididymal fat pad weight to body weight ratio in fed and fasted Tph1f/f and Tph1gutΔ/Δ mice (n≥6). (F) Average size of adipocytes from fat pad of fed and 48 h-fasted Tph1f/f and Tph1gutΔ/Δ mice (n≥5). (G) 48 h fasting-induced body weight loss (n≥7). Plasma levels of (H) glycerol and (I) FFA in mice with implanted placebo or serotonin-releasing pellets fasted for indicated time (n≥8). (J) Glycerol and (K) FFA release from mouse epigonadal fat explants stimulated with indicted dose of serotonin (n≥5). * P<0.05,  P<0.01, * P<0.001. For each pair of bars in (C)-(G), the left bar represents Tph1f/f and the right bar represents Tph1gutΔ/Δ. For each pair of bars in (H) and (I), the left bar represents placebo and the right bar represents serotonin.
Figure 5A:
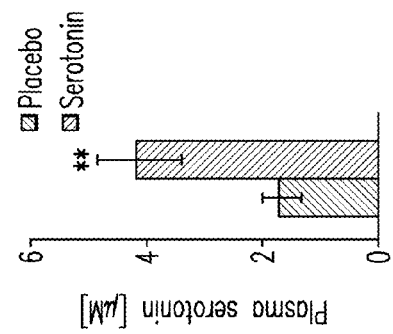
FIG. 5. (A) Plasma serotonin concentration in fed and fasted Tph1f/f and Tph1gutΔ/Δ mice (n≥5). (B) Histology of fat pad from fed and 48 h-fasted Tph1f/f and Tph1gutΔ/Δ mice (n≥5). (C) Plasma serotonin concentration in mice with implanted placebo and serotonin-releasing pellets (n≥8). (D) Relative expression of indicated genes in fat pad from fed and fasted Tph1f/f and Tph1gutΔ/Δ mice (n≥5). * P<0.05, ** P<0.01.

Tph1 expression, and even more plasma serotonin levels, were both significantly increased in mice fasted for only 2 h and remained so during a 48 h fasting period (FIGS. 1A and B). This elevation of circulating serotonin levels occurred before the elevation of glucagon, a hormone involved in the adaptation to fasting in vertebrates (7). Fasting triggers mobilization of triglycerides, in the form of glycerol and free fatty acids (FFAs), through lipolysis (8, 9). Thus, the potential role of GDS in this process was determined through the study of mice lacking Tph1 only in the gut (Tph1gutΔ/Δ mice) (FIG. 5A).

Example 3

Plasma Serotonin Levels Regulate Lypolysis

Unlike Tph1fl/fl control littermates, Tph1gutΔ/Δ mice did not show a significant increase in circulating levels of FFAs and glycerol following a 4 h fasting period. While glycerol circulating levels did not increase even when fasting was prolonged up to 48 h, FFAs levels did increase in Tph1gutΔ/Δ mice during this extended fasting but not to the same extent as in Tph1fl/fl mice (FIGS. 1C and D). As a consequence of this failure to induce appropriate lipolysis, Tph1gutΔ/Δ mice fasted for 48 h displayed heavier fat pads, larger adipocytes and lost significantly less weight than Tph1fl/fl mice (FIG.

Figure 5B:
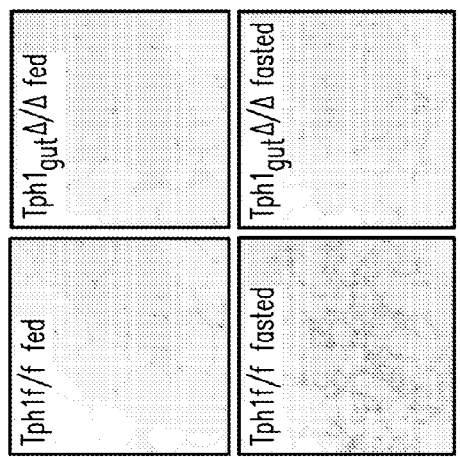

1E-G and FIG. 5B). These results indicate that serotonin is a physiological regulator of lipolysis.

Example 4

Serotonin Affects Lypolysis in the Fed State

Figure 1H:
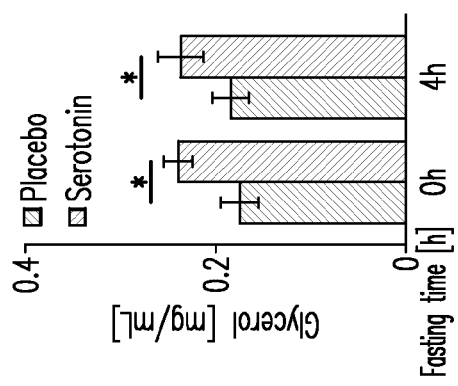
Figure 1G:
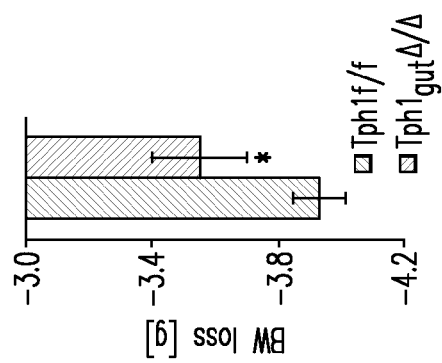
Figure 1K:
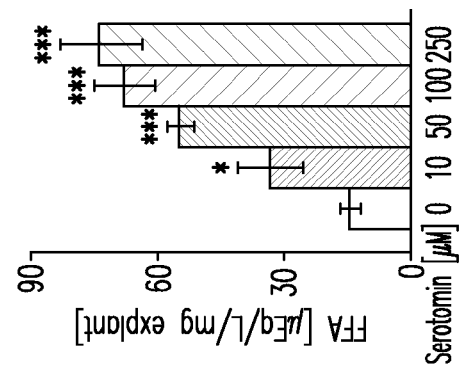
Figure 5C:
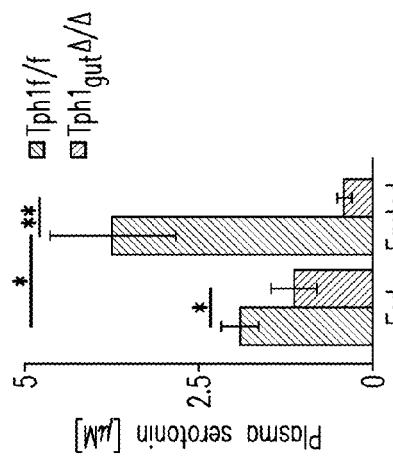

Whether serotonin could affect lipolysis in fed mice, a situation in which this process is normally blocked (8, 9), was also tested. This was done by implanting subcutaneously serotonin releasing pellets in WT mice. These pellets increased circulating levels of serotonin approximately two-fold (FIG. 5C). This resulted in a significant increase in circulating levels of glycerol and FFAs (FIGS. 1H and I). Lipolysis was further enhanced if WT mice implanted with these pellets were fasted for 4 h. Hence, GDS is sufficient to induce lipolysis in fed or fasted mice.

Example 5

GDS Acts Directly on Adipocytes Through Htr2b

Figure 1J:
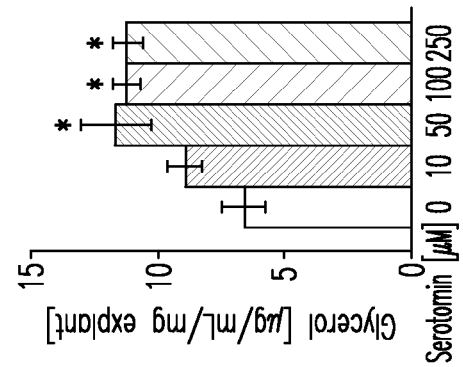
Figure 5D:
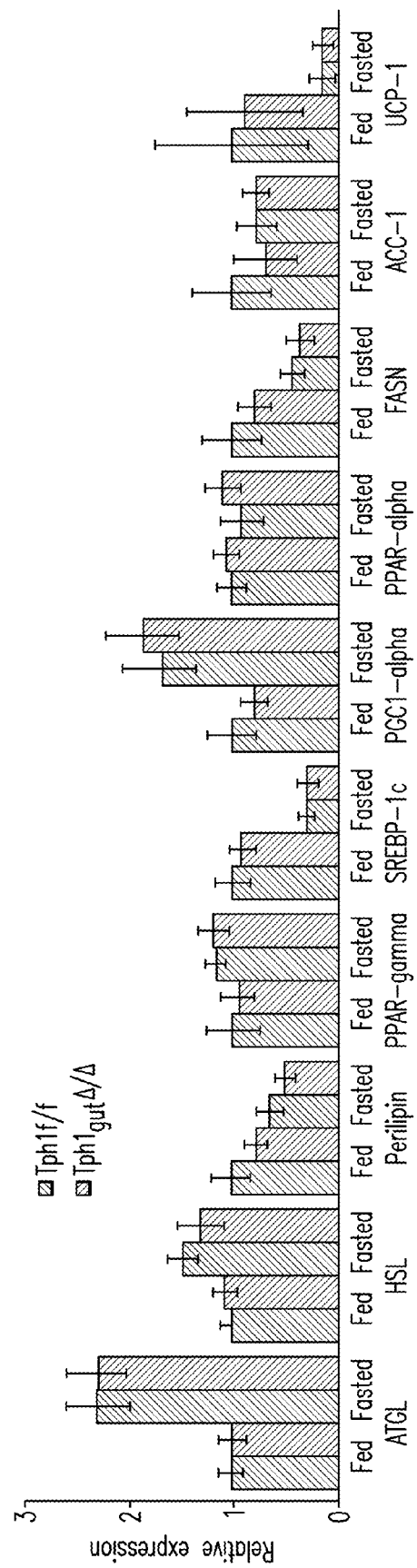
Figure 6A:
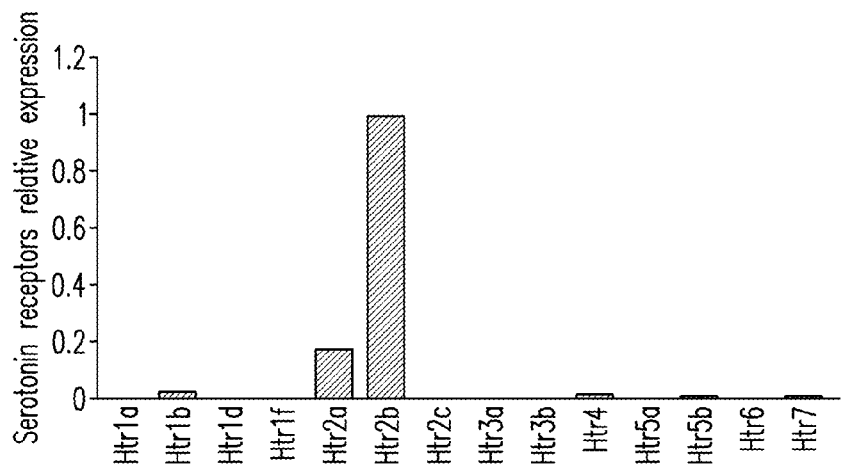
FIG. 6. (A) Relative expression of indicated serotonin receptors in primary mouse adipocytes. (B) Relative expression of indicated genes in fat pad from fed and fasted Htr2bf/f and Htr2bfatΔ/Δ mice (n≥5). (C) Histology of fat pad from fed and 48 h-fasted Htr2bf/f and Htr2bfatΔ/Δ mice (n≥5).

To determine whether GDS promotes lipolysis by acting directly on adipocytes, epididymal fat pads were treated with increasing amounts of serotonin. This treatment significantly increased release of both glycerol and FFAs (FIGS. 1J and K). Of note, there was no evidence of white fat into brown fat transformation in Tph1 gut$\Delta/\Delta$ mice (10) (FIG. 5D). In view of these results, the identity of the signaling pathway used by GDS in adipocytes was investigated. Among the fourteen known serotonin receptors (1), Htr2b was by far the most highly expressed in mouse adipocytes (FIG. 6A). Furthermore, its expression in white adipose tissue increased upon fasting (FIG. 2A). Hence, mice lacking Htr2b in adipocytes only were generated (Htr2bfat$\Delta/\Delta$ mice) and their response to fasting was analyzed.

Fasting failed to increase glycerol circulating levels in Htr2bfat$\Delta/\Delta$, as it did in Htr2bfl/fl mice (FIG. 2B). The increase in FFAs circulating levels observed upon fasting in Htr2bfat$\Delta/\Delta$ mice was also significantly weaker than in Htr2bfl/fl mice (FIG. 2C). Consequently, Htr2bfat$\Delta/\Delta$ mice had bigger fat pads, larger adipocytes, and lost less weight during a 48 h fasting than Htr2bfl/fl littermates (FIG. 2D-F and FIG. 6C). Moreover, in cell culture, serotonin failed to enhance release of glycerol and FFAs from Htr2b-deficient fat pad explants. This was not due to the poor quality of explants because isoproterenol, used as a positive control, favored equally well FFAs and glycerol release from these explants (FIGS. 2G and H).

Example 6

GDS Controls the Activation of Hormone Sensitive Lipase (HSL)

Figure 6B:
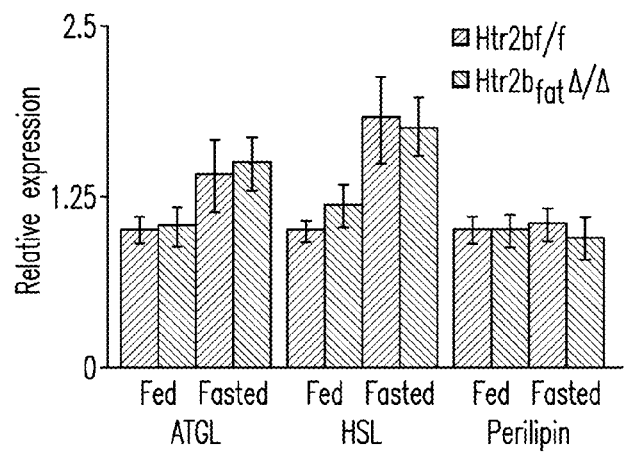
Figure 6C:
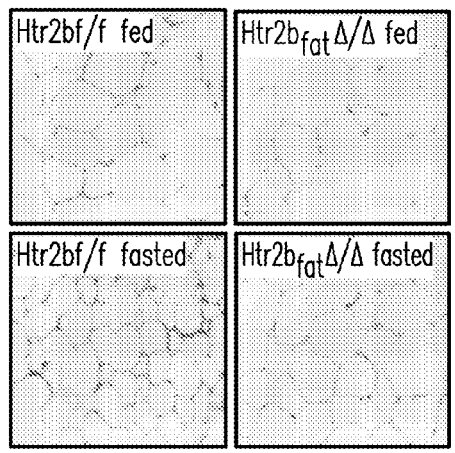
Figure 9A:
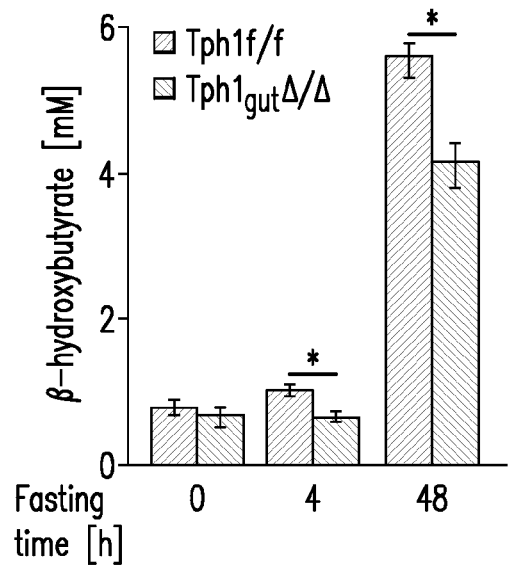
FIG. 9. (A) Plasma levels of β-hydroxybutyrate in mice of indicated genotypes fasted for indicated times (n≥7). (B) Plasma levels of triglycerides in mice of indicated genotypes fasted for indicated times (n≥7). (C) Percent of fat content in fed and fasted mice of indicated genotypes measured by magnetic resonance imaging (MRI) (n≥5). (D) Percent of fat content loss during 48 hr fasting in relation to initial fat content of each animal; average of five mice of Tph1f/f and Tph1gutΔ/Δ genotype.
Figure 9B:
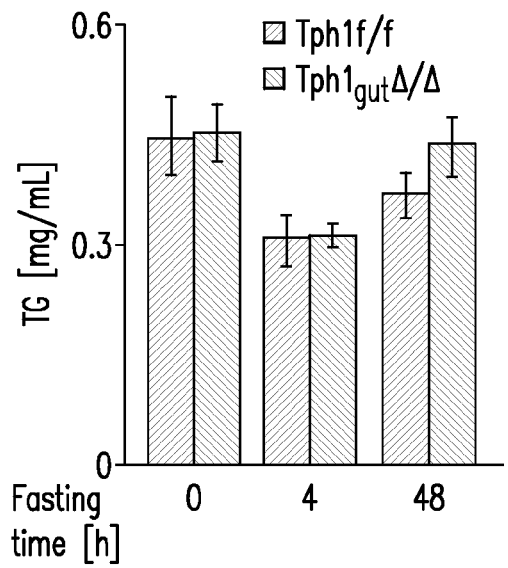
Figure 9C:
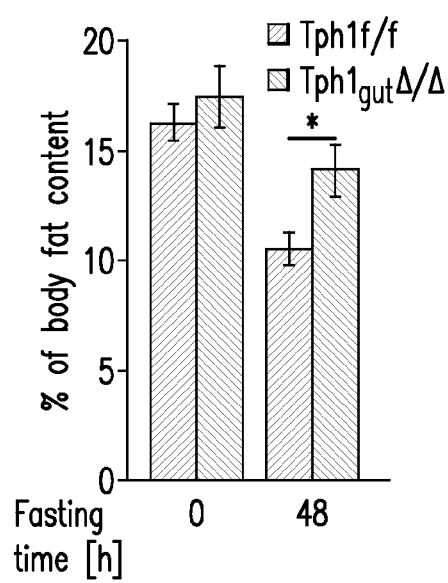
Figure 9D:
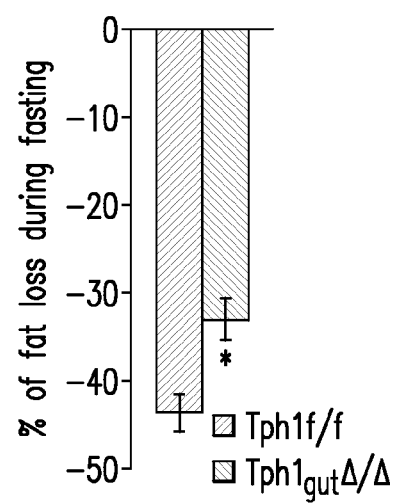
Figure 10A:
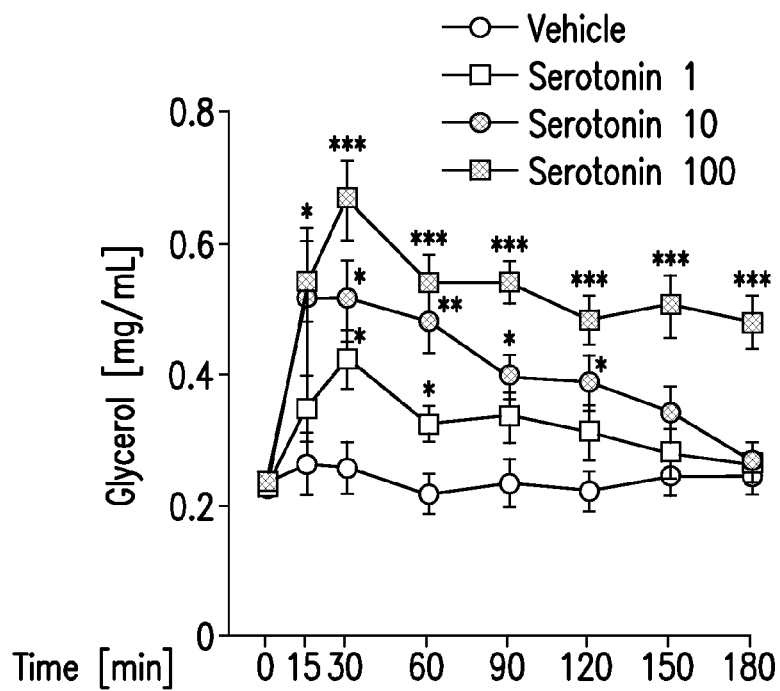
FIG. 10. (A) Plasma levels of glycerol at indicated time points after i.p. injection of serotonin (doses in mg/kg BW) (n≥5). Data represented as mean±SEM, *p<0.05, p<0.01, *p<0.001. (B) Plasma levels of FFAs at indicated time points after i.p. injection of serotonin (doses in mg/kg BW) (n≥5). Data represented as mean±SEM, *p<0.05, p<0.01, *p<0.001. (C) Plasma levels of β-hydroxybutyrate in mice lacking Htr2b in adipose tissue (deletion by aP2-Cre, indicated on graphs by Htr2bfatΔ/Δ [aP2]) fasted for indicated times (n≥20). (D) Western blot analysis of expression and activation of indicated proteins in fat pads isolated from Htr2bf/f and Htr2bfatΔ/Δ (aP2) mice fasted for 48 hr. Data are represented as mean±SEM, *p<0.05, ***p<0.001.
Figure 10B:
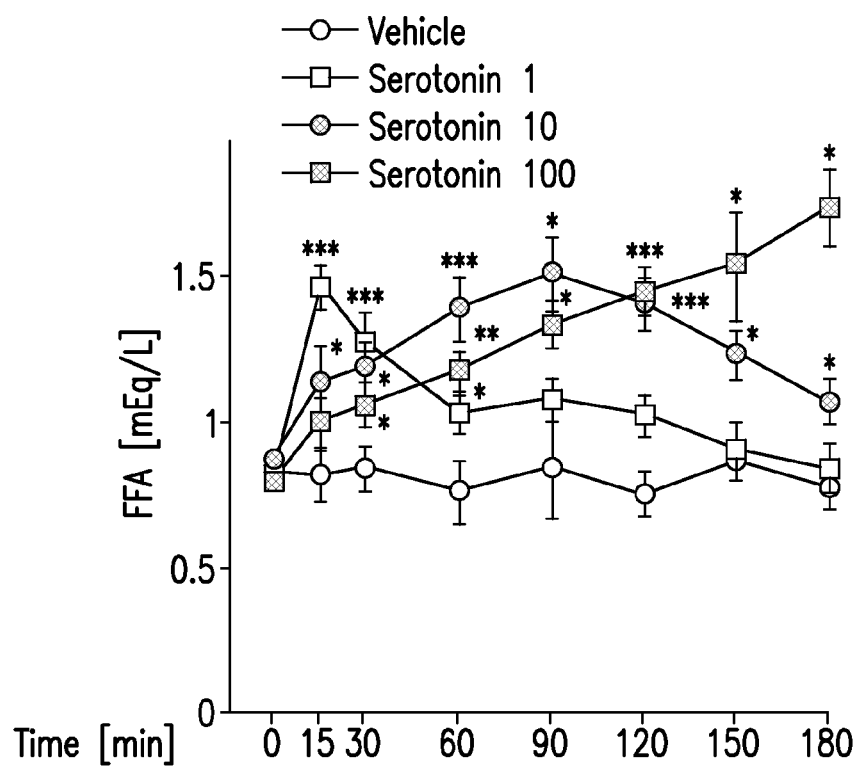
Figure 10D:
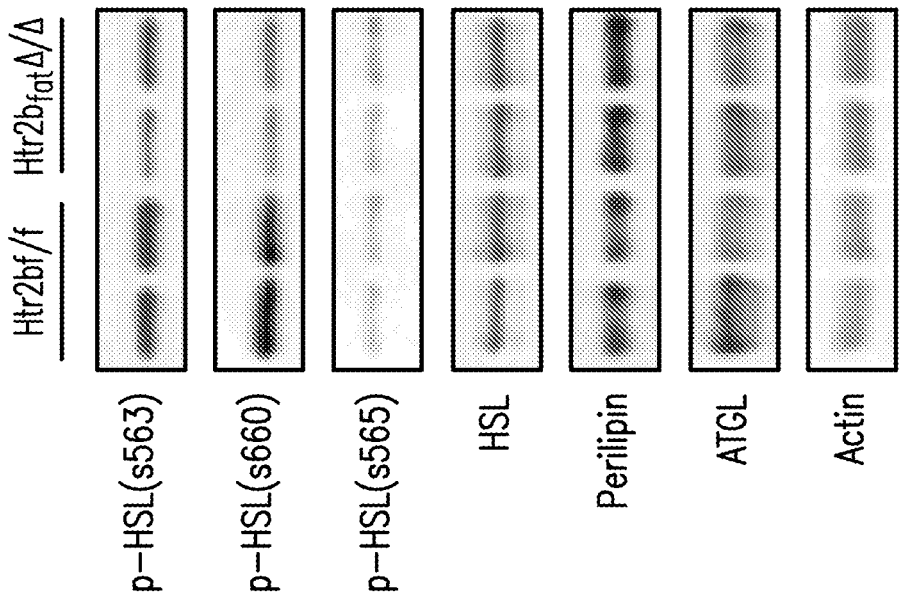
Figure 10C:
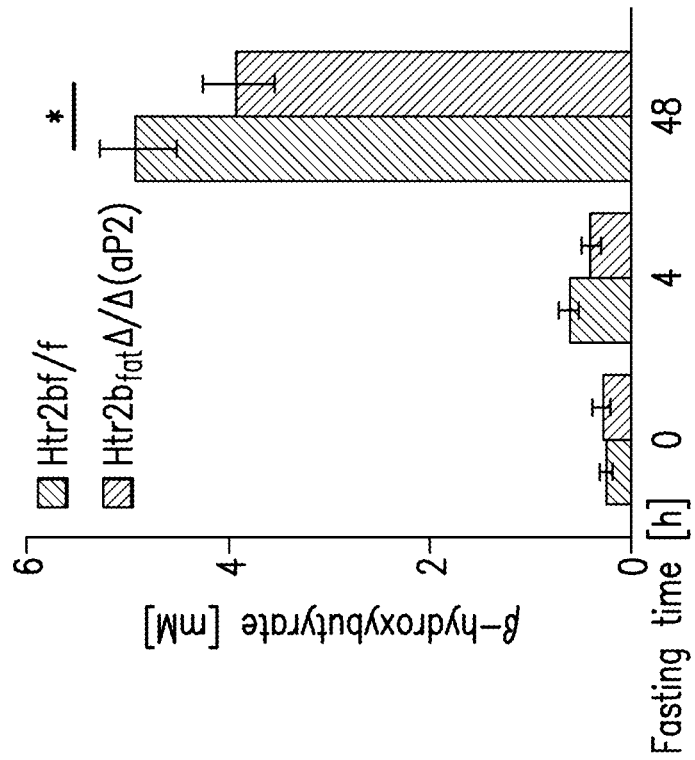
Figure 11A:
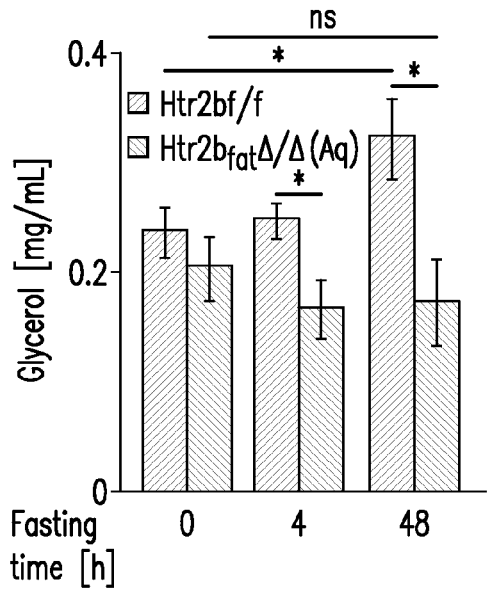
FIG. 11. (A) Plasma levels of glycerol in mice lacking Htr2b in adipose tissue (deletion by Adiponectin-Cre, indicated on graphs by Htr2bfatΔ/Δ [Aq]) fasted for indicated times (n≥6). (B) Plasma levels of FFAs (H) in mice lacking Htr2b in adipose tissue (deletion by Adiponectin-Cre, indicated on graphs by Htr2bfatΔ/Δ [Aq]) fasted for indicated times (n≥6). (C) Glycerol levels in Htr2bf/f and Htr2bfatΔ/Δ
Figure 11B:
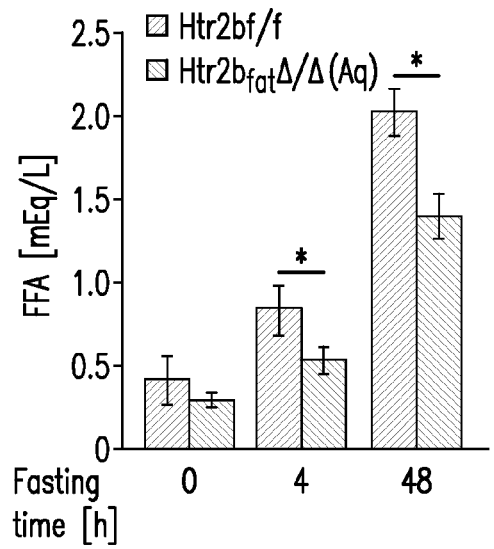
Figure 11C:
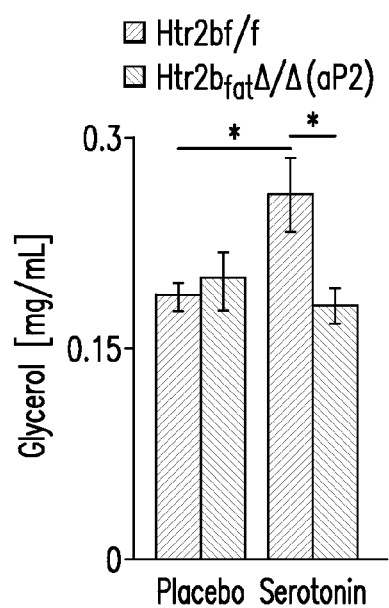
Figure 11D:
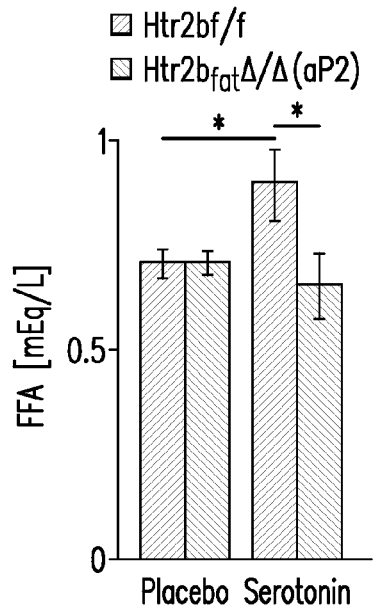

To begin deciphering serotonin's molecular mode of action in adipocytes, the expression, accumulation, and phosphorylation of key lipolytic enzymes (11-14) were analyzed. There was no alteration of gene expression in Tph1 gut$\Delta/\Delta$ and Htr2bfat$\Delta/\Delta$ mice (FIG. 5D and FIG. 6B) or in the accumulation of many enzymes involved in lipolysis. In contrast, serotonin favored, in an Htr2b-dependent manner, phosphorylation of hormone sensitive lipase (HSL) on serine residues 563 and 660 (FIG. 2I). Those phosphorylation events enhance HSL activity (15, 16). Taken together, these experiments indicate that serotonin promotes lipolysis by signaling in adipocytes through Htr2b to increase phosphorylation and activity of HSL.

Example 7

GDS Promotes Gluconeogenesis

Figure 3D:
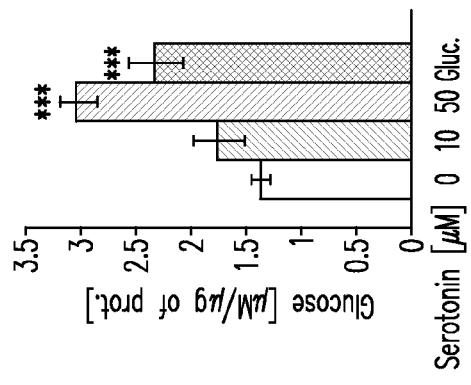
FIG. 3. GDS promotes gluconeogenesis in liver by acting through Htr2b. (A) Glycerol evoked glucose production in Tph1f/f and Tph1gutΔ/Δ mice (n≥8). (B) Pyruvate tolerance test in Tph1f/f and Tph1gutΔ/Δ mice (n≥8). (C) Glycerol tolerance test in WT mice implanted with placebo or serotonin-releasing pellets (n≥8). (D) Hepatic glucose production during hyperinsulinemiceuglycemic clamp in Tph1f/f and Tph1gutΔ/Δ mice (n≥7). (E) Production of glucose from glycerol by primary hepatocytes stimulated with indicated doses of serotonin or 100 nM glucagon (n=5). (F) Relative expression of indicated serotonin receptors in liver of fed and fasted mice. (G) Glycerol tolerance test in Htr2b1f/f and Htr2bliverΔ/Δ mice (n≥7). (H) Pyruvate tolerance test in Htr2bf/f and Htr2bliverΔ/Δ mice (n≥7). (I) Glycerol-induced glucose production in Htr2bf/f and Htr2bliverΔ/Δ hepatocytes stimulated by 50 μM serotonin (n=5). Normalized (J) FBPase and (K) G6Pase activity in livers of Htr2bf/f and Htr2bliverΔ/Δ mice (n≥6). * P<0.05,  P<0.01, * P<0.001. For the pair of bars in (D), the left bar represents Tph1f/f and the right bar represents Tph1gutΔ/Δ. For each pair of bars in (I)-(K), the left bar represents Htr2bf/f and the right bar represents Htr2bliverΔ/Δ.

Glycerol can be converted to glucose by the liver during fasting (7). Hence, results presented above raised the prospect that GDS may promote gluconeogenesis simply through its ability to increase glycerol circulating levels or independently of its role on lipolysis. These possibilities were tested by measuring glucose production following glycerol injection (17). In the conditions of this experiment, glycerol did not increase circulating glucose levels in Tph1 gut$\Delta/\Delta$ mice to the same extent as in Tph1fl/fl mice (FIG. 3A). The same was true for pyruvate, the initial substrate in liver gluconeogenesis (FIG. 3B). Conversely, in WT mice implanted with serotonin pellets glycerol increased blood glucose levels to a higher level than in controls (FIG. 3C). These experiments indicated that serotonin is a physiological regulator of liver gluconeogenesis and that this function is not a mere consequence of its action on lipolysis. To further test if serotonin can induce gluconeogenesis from endogenous substrates, Tph1gut$\Delta/\Delta$ mice were subjected to hyperinsulinemic-euglycemic clamp. Hepatic glucose production was markedly reduced in Tph1gut$\Delta/\Delta$ mice (FIG. 3D). Consistent with the notion that serotonin adapts the organism to food deprivation glycogen synthesis rate was also increased in Tph1gut$\Delta/\Delta$ mice (FIG. 7A). That whole-body glycolysis rate was unchanged ruled out that the observed effect on gluconeogenesis might be secondary to alterations of this process (FIG. 7A).

Example 8

GDS Promotes Gluconeogenesis in Hepatocytes Through Htr2b

Figure 3F:
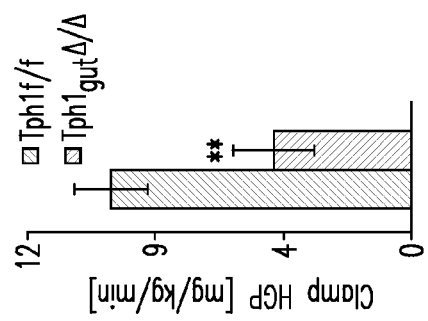
Figure 3E:
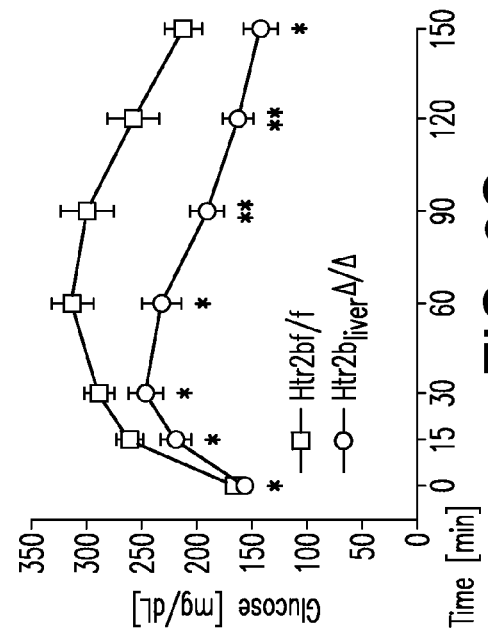
Figure 3G:
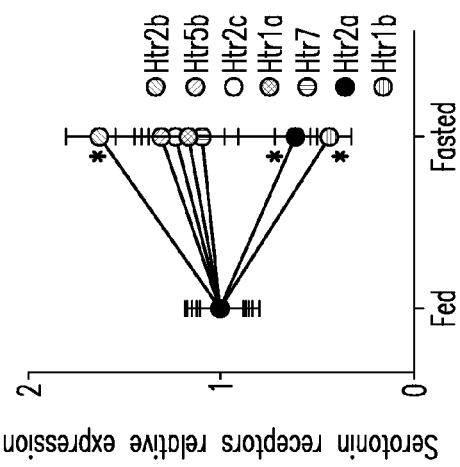
Figure 3H:
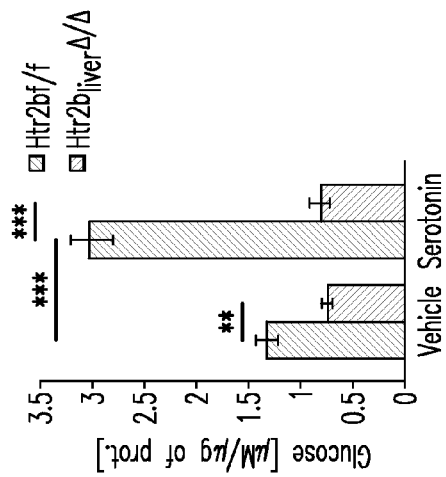
Figure 3I:
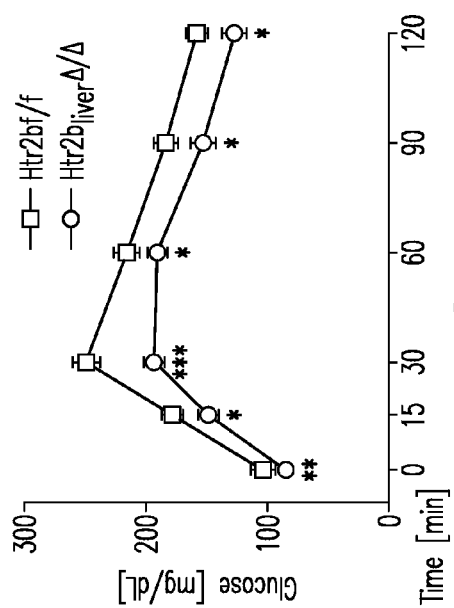
Figure 3J:
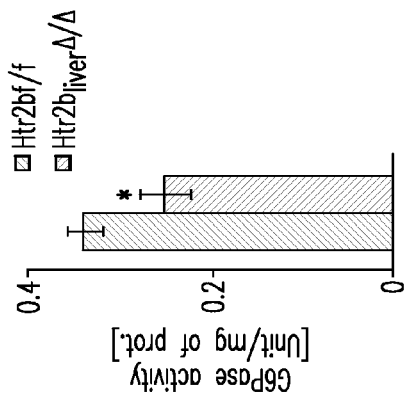
Figure 3K:
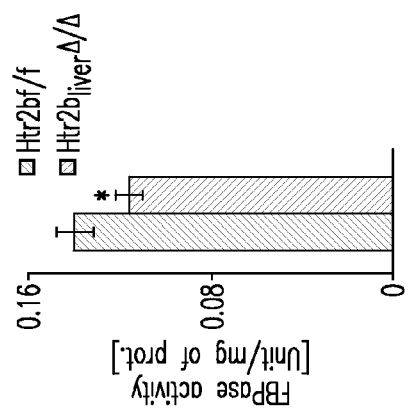

In cell culture, serotonin stimulated conversion of glycerol to glucose in hepatocytes to the same extent as glucagon, a positive control, did (FIG. 3E). Since Htr2b was the most abundant serotonin receptor in the liver and its expression in this organ also increased upon fasting (FIG. 3F and FIG. 7B), whether Htr2b was mediating serotonin regulation of hepatic gluconeogenesis was tested. Glycerol and pyruvate did not increase circulating glucose levels in Htr2bliver$\Delta/\Delta$ mice to the same extent as in Htr2bfl/fl littermate controls (FIG. 3G, H), and serotonin could not induce glucose production from glycerol when added to Htr2b$\Delta/\Delta$ hepatocytes (FIG. 3I). These data indicate that serotonin stimulates gluconeogenesis by signaling through Htr2b present in hepatocytes. That glycogen content was increased in livers of fasted Htr2bliver$\Delta/\Delta$ mice (FIG. 7C) indicated that the regulation of glycogen synthesis by serotonin previously noted (18) occurs through Htr2b. Generation of ketone bodies in Htr2bliver$\Delta/\Delta$ was normal, indicating that serotonin signaling does not affect this aspect of adaptation to fasting (FIG. 7D). Next, the expression of key genes involved in gluconeogenesis from glycerol (FBPase, G6Pase, glycerol kinase and aquaporin 9) (7) was analyzed, but no significant change in Htr2bliver$\Delta/\Delta$ mice (FIG. 7E) was observed. In contrast, when measured through classical bioassays (19, 20), the enzymatic activity of the two rate limiting enzymes for this process, FBPase and G6Pase, were decreased 20% and 25%, respectively, in Htr2bliver$\Delta/\Delta$ mice (FIGS. 3J and K). These results suggested that serotonin favors gluconeogenesis, in part, by enhancing activity of these enzymes.

Example 9

Blocking GDS Activity Increases Glucose Tolerance

FFAs promote insulin resistance (21, 22). Accordingly, insulin sensitivity, measured by insulin tolerance test and glucose infusion rates during hyperinsulinemic-euglycemic clamp, was significantly improved in Tph1gutΔ/Δ and in Htr2bfatΔ/Δ mice compared to controls (FIG. 4A, FIG. 8A, and FIG. 7A). The ability of serotonin to promote liver gluconeogenesis also influenced glucose homeostasis since both Tph1gutΔ/Δ and Htr2bliverΔ/Δ mice were significantly more tolerant to a glucose load than control littermates (FIG. 4B and FIG. 8B). On the other hand, GDS does not influence glucose stimulated insulin secretion at basal conditions (23) (FIG. 8C). These results implied that decreasing GDS synthesis should attenuate the severity of Type II diabetes.

Example 10

A TPH1 Inhibitor Increases Insulin Sensitivity and Increases Glucose Tolerance

Tph1gutΔ/Δ mice were fed a high fat diet, inducing obesity and Type II diabetes (FIG. 8D). Circulating glycerol and FFA levels were reduced in Tph1gutΔ/Δ mice compared to control animals (FIGS. 4C and D). Moreover, gluconeogenesis was partially normalized in Tph1gutΔ/Δ mice fed a high fat diet (FIG. 8E). These mice were also significantly more insulin sensitive and glucose tolerant than Tph1fl/fl mice fed the same diet (FIG. 4E, F).

A small molecule inhibitor of TPH1, and thus GDS synthesis, LP533401, that does not cross efficiently the blood-brain barrier (24), was tested for its effect on glucose intolerance. In WT mice fed a high fat diet, LP533401 (100 mg/kg/day) resulted in an 80% reduction of circulating serotonin levels, a decrease in glycerol and a normalization of FFAs circulating levels (FIG. 4G, H and FIG. 8F). Consequently, insulin sensitivity was normalized while gluconeogenesis and glucose tolerance were significantly improved in LP533401-treated mice fed a high fat diet (FIG. 4I, J and FIG. 8H). When given to WT mice fed a normal diet, LP533401 decreased glycerol and FFA levels, decreased gluconeogenesis rate, and improved glucose and insulin tolerance to the extent shown by Tph1gutΔ/Δ mice (FIG. 17A-C and FIG. 18A-B). LP533401 did not affect body weight gain (FIG. 8G).

REFERENCES FOR EXAMPLES 2-10

1. M. Berger, J. A. Gray, B. L. Roth, *Annu Rev Med* 60, 355 (2009).
2. V. K. Yadav et al., *Cell* 135, 825 (Nov. 28, 2008).
3. M. Frost et al., *J Bone Miner Res* 26, 1721 (August).
4. A. Saarinen et al., *Clin Endocrinol (Oxf)* 72, 481 (April, 2010).
5. A. Black et al., *J Gerontol A Biol Sci Med Sci* 56, B98 (March, 2001).
6. F. Elefteriou et al., *Cell Metab* 4, 441 (December, 2006).
7. H. V. Lin, D. Accili, *Cell Metab* 14, 9 (Jul. 6, 2011).
8. E. D. Rosen, B. M. Spiegelman, *Nature* 444, 847 (Dec. 14, 2006).
9. R. Zimmermann, A. Lass, G. Haemmerle, R. Zechner, *Biochim Biophys Acta* 1791, 494 (June, 2009).
10. F. M. Fisher et al., *Genes Dev* 26, (2012).
11. R. Zimmermann et al., *Science* 306, 1383 (Nov. 19, 2004).
12. G. Haemmerle et al., *Science* 312, 734 (May 5, 2006).
13. J. Martinez-Botas et al., *Nat Genet* 26, 474 (December, 2000).
14. J. Osuga et al., *Proc Natl Acad Sci USA* 97, 787 (Jan. 18, 2000).
15. A. S. Greenberg et al., *J Biol Chem* 276, 45456 (Nov. 30, 2001).
16. M. W. Anthonsen, L. Ronnstrand, C. Wernstedt, E. Degerman, C. Holm, *J Biol Chem* 273, 215 (Jan. 2, 1998).
17. N. Maeda et al., *Proc Natl Acad Sci USA* 101, 17801 (Dec. 21, 2004).
18. L. J. Hampson, P. Mackin, L. Agius, *Diabetologia* 50, 1743 (August, 2007).
19. A. Reyes, M. E. Burgos, E. Hubert, J. C. Slebe, *J Biol Chem* 262, 8451 (Jun. 25, 1987).
20. M. Alegre, C. J. Ciudad, C. Fillat, J. J. Guinovart, *Anal Biochem* 173, 185 (Aug. 15, 1988).
21. A. R. Saltiel, C. R. Kahn, *Nature* 414, 799 (Dec. 13, 2001).
22. G. I. Shulman, *J Clin Invest* 106, 171 (July, 2000).
23. H. Kim et al., *Nat Med* 16, 804 (July).
24. Q. Liu et al., *J Pharmacol Exp Ther* 325, 47 (April, 2008).

What is claimed is:

1. A method of treating or preventing Type II diabetes in a patient known or suspected to be in need of such treatment or prevention comprising administering to the patient a therapeutically effective amount of a tryptophan hydroxylase 1 (TPH1) inhibitor.

2. A method of lowering blood glucose levels in a patient known or suspected to be in need of such lowering of blood glucose levels comprising administering to the patient a therapeutically effective amount of a tryptophan hydroxylase 1 (TPH1) inhibitor.

3. The method of claim 1 or 2 wherein the TPH1 inhibitor is selected from the following or from pharmaceutically acceptable salts and/or solvates thereof:

(1)

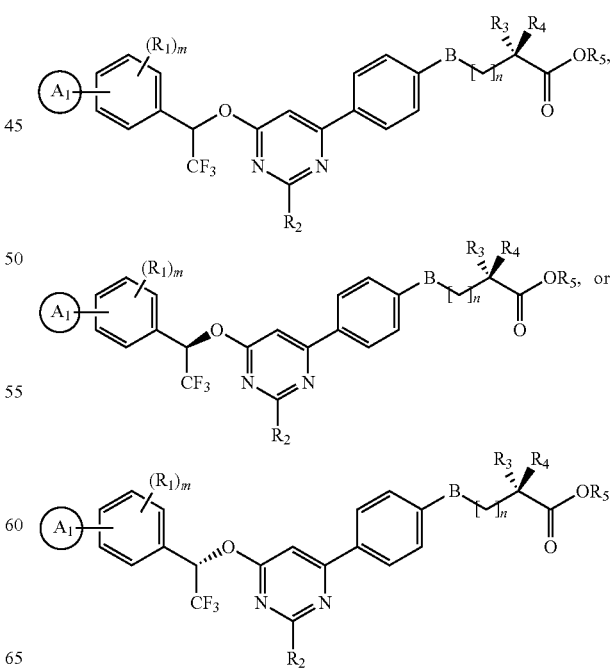

where $A_1$ is optionally substituted heterocycle or 3-fluorophenyl; B is O, N, or —$CH_2$—; each $R_1$ is independently halogen, hydrogen, $C(O)R_4$, $OR_4$, $NR_BR_C$, $S(O_2)R_4$, or optionally substituted alkyl, alkyl-aryl or alkyl-heterocycle; $R_2$ is halogen, hydrogen, $C(O)R_4$, $OR_4$, $NR_BR_C$, $S(O_2)R_4$, or optionally substituted alkyl, alkyl-aryl or alkyl-heterocycle; either $R_3$ is $NHR_6$ and $R_4$ is hydrogen or, alternatively, $R_3$ and $R_4$ together form =O; $R_5$ is hydrogen or optionally substituted alkyl, alkyl-aryl, alkyl-heterocycle, aryl, or heterocycle; $R_6$ is hydrogen, $C(O)R_4$, $C(O)OR_4$, or optionally substituted alkyl, alkyl-aryl, alkyl-heterocycle, aryl, or heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; m is 0-4; and n is 0 or 1.

4. The method of claim 1 or 2 wherein the TPH1 inhibitor is (121)

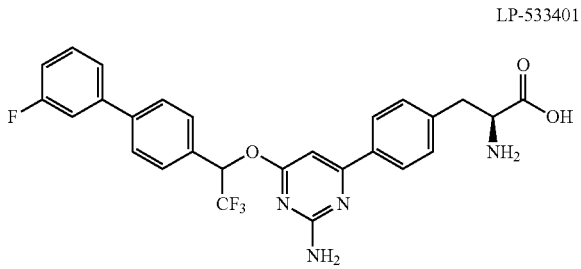 [SMILES: Nc1nc(OC(c2ccc(-c3cccc(F)c3)cc2)C(F)(F)F)cc(-c2ccc(C[C@H](N)C(=O)O)cc2)n1]

LP-533401 or (122)

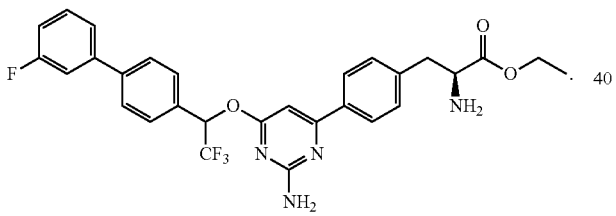

LP-615819

5. The method of claim 1 or 2 wherein the TPH1 inhibitor does not cross the blood brain barrier or the TPH1 inhibitor does not significantly inhibit tryptophan hydroxylase 2 (TPH2).

6. The method of claim 1 or 2 wherein the patient's level of serum or plasma serotonin is measured prior to administering the TPH1 inhibitor.

7. The method of claim 1 or 2 wherein the patient's level of serum or plasma serotonin is measured after administering the TPH1 inhibitor.

8. The method of claim 1 or 2 wherein the patient is a mammal.

9. The method of claim 1 or 2 wherein the patient is a human.

10. The method of claim 1 or 2 wherein the TPH1 inhibitor is administered with another compound that is known to prevent or treat Type II diabetes.

11. The method of claim 1 or 2 wherein the TPH1 inhibitor is administered with an inhibitor of hormone sensitive lipase.

12. A method of identifying and treating a patient in need of therapy for diabetes comprising:

(a) identifying a patient in need of therapy for diabetes;

(b) administering to the patient a therapeutically effective amount of a TPH1 inhibitor in order to treat diabetes in the patient identified in step (a).

13. A method for identifying a patient having diabetes or at risk of developing diabetes and treating the patient, comprising:

a) determining the level of serum or plasma serotonin in a biological sample from the patient and in a biological sample from a normal subject;

b) administering to the patient a therapeutically effective amount of a TPH1 inhibitor if the level of serum or plasma serotonin in the sample from the patient is elevated by at least about 25% above the serum or plasma serotonin level in the sample from the normal subject;

whereby the patient's serum or plasma serotonin level is lowered and diabetes is thereby treated.

* * * * *